US011633487B2

(12) United States Patent
Bisek et al.

(10) Patent No.: US 11,633,487 B2
(45) Date of Patent: Apr. 25, 2023

(54) PRODRUGS COMPRISING AN AMINOALKYL GLYCINE LINKER

(71) Applicant: Ascendis Pharma A/S, Hellerup (DK)

(72) Inventors: Nicola Bisek, Heidelberg (DE); Harald Rau, Dossenheim (DE); Felix Cleemann, Mainz (DE); Thomas Knappe, Heidelberg (DE); Romy Reimann, Hofheim (DE)

(73) Assignee: ASCENDIS PHARMA A/S, Hellerup (DK)

( * ) Notice: Subject to any disclaimer, the term of this patent is extended or adjusted under 35 U.S.C. 154(b) by 1100 days.

(21) Appl. No.: 15/502,084

(22) PCT Filed: Aug. 4, 2015

(86) PCT No.: PCT/EP2015/067929
§ 371 (c)(1),
(2) Date: Feb. 6, 2017

(87) PCT Pub. No.: WO2016/020373
PCT Pub. Date: Feb. 11, 2016

(65) Prior Publication Data
US 2017/0224829 A1 Aug. 10, 2017

(30) Foreign Application Priority Data
Aug. 6, 2014 (EP) .................... 14180004

(51) Int. Cl.
A61K 47/65 (2017.01)
A61K 47/60 (2017.01)
A61K 38/28 (2006.01)
A61K 47/54 (2017.01)
A61K 47/68 (2017.01)

(52) U.S. Cl.
CPC .............. A61K 47/60 (2017.08); A61K 38/28 (2013.01); A61K 47/542 (2017.08); A61K 47/65 (2017.08); A61K 47/6889 (2017.08)

(58) Field of Classification Search
CPC . A61K 47/65; A61K 47/6889; A61K 2800/57
See application file for complete search history.

(56) References Cited

U.S. PATENT DOCUMENTS

| 6,017,954 A * | 1/2000 | Folkman | C07D 231/12 |
| | | | 514/475 |
| 6,096,330 A * | 8/2000 | Chaudhry | A01N 57/20 |
| | | | 424/405 |
| 7,771,727 B2 * | 8/2010 | Fuselier | A61P 29/00 |
| | | | 424/185.1 |
| 8,450,469 B2 * | 5/2013 | Lee | C07H 7/00 |
| | | | 536/23.1 |
| 2002/0099057 A1 * | 7/2002 | Langer | A61K 31/704 |
| | | | 514/255.02 |
| 2004/0101941 A1 * | 5/2004 | Lavi | C12N 11/08 |
| | | | 435/196 |
| 2007/0021331 A1 * | 1/2007 | Fraser | C07K 5/0812 |
| | | | 514/90 |
| 2008/0248030 A1 * | 10/2008 | Folkman | A61P 9/00 |
| | | | 424/133.1 |
| 2013/0090326 A1 * | 4/2013 | Duffy | C07D 487/04 |
| | | | 514/210.18 |
| 2013/0101527 A1 * | 4/2013 | Llinas | A61K 47/26 |
| | | | 424/48 |
| 2013/0137831 A1 * | 5/2013 | Petersen | A61K 31/336 |
| | | | 525/329.4 |
| 2016/0081782 A1 * | 3/2016 | Weyer | A61K 8/585 |
| | | | 604/500 |

FOREIGN PATENT DOCUMENTS

| EP | 0120558 | 10/1984 |
| EP | 0252810 | 1/1988 |
| WO | WO 2005/099768 | 10/2005 |
| WO | WO 2006/003014 | 1/2006 |
| WO | WO 2006/136586 | 12/2006 |
| WO | WO 2009/095479 | 8/2009 |
| WO | WO 2011/012715 | 2/2011 |
| WO | WO 2011/012722 | 2/2011 |
| WO | WO 2011/089214 | 7/2011 |
| WO | WO 2011/089215 | 7/2011 |
| WO | WO 2011/089216 | 7/2011 |

(Continued)

OTHER PUBLICATIONS

Moody et al. Vasoactive intestinal peptide-camptothecin conjugates inhibit the proliferation of breast cancer cells. Peptides. 2007, vol. 28, pp. 1883-1890. (Year: 2007).*
Oblak et al. Antibacterial activity of gemini quaternary ammonium salts. FEMS Microbiology Letters. Published online Dec. 11, 2013, vol. 350, pp. 190-198. (Year: 2013).*
International Search Report issued in corresponding International Application No. PCT/EP2015/067929 dated Sep. 28, 2015.
Nancy E. Kohl et al., Selective Inhibition of ras-Dependent Transformation by a Farnesyltransferase Inhibitor, 260 Science 1934-1937 (Jun. 25, 1993).

(Continued)

Primary Examiner — Jeffrey E. Russel
(74) Attorney, Agent, or Firm — Dechert LLP

(57) ABSTRACT

The present invention relates to novel prodrugs of primary or secondary amine- or hydroxyl-comprising biologically active moieties and pharmaceutically acceptable salts thereof, prodrug reagents, pharmaceutical compositions comprising these prodrugs and the use of these prodrugs. A disclosed prodrug may include a biologically active moiety reversibly and covalently linked to a specialized protective group; the linker may be reversible (i.e., hydrolytically cleavable in the absence of enzymes under physiological conditions) and, upon cleavage, may release a drug in its unmodified, pharmacologically active form.

19 Claims, No Drawings

(56) References Cited

FOREIGN PATENT DOCUMENTS

| WO | WO 2013/024047 | 2/2013 |
| WO | WO 2013/024049 | 2/2013 |
| WO | WO 2014/056926 | 4/2014 |

OTHER PUBLICATIONS

Charles D. Conover et al., *Camptothecin Delivery Systems: The Utility of Amino Acid Spacers for the Conjugation of Camptothecin with Polyethylene Glycol to Create Produgs*, 14 Anti-Cancer Drug Design 499-506 (1999).
European Office Action dated Dec. 10, 2020 in corresponding European Application No. 15 745 217.8-1112.
Liu et al., "Magnetic nanoparticles modified with DTPA-AMC-rare earth for fluorescent and magnetic resonance dual mode imaging", Dalton Transactions, (2012), 8723-8728, 41.
Tandon et al., "Characterization of 7-amino-4-methylcoumarin as an effective antitubercular agent: structure-activity relationships", Journal of Antimicrobial Chemotherapy, Sep. 14, 2011, 2543-2555, 66.

\* cited by examiner

PRODRUGS COMPRISING AN AMINOALKYL GLYCINE LINKER

The present application claims priority from PCT Patent Application No. PCT/EP2015/067929 filed on Aug. 4, 2015, which claims priority from European Patent Application No. EP 14180004.5 filed on Aug. 6, 2014; the disclosure of PCT Patent Application No. PCT/EP2015/067929 is incorporated herein by reference in its entirety.

The present invention relates to novel prodrugs of primary or secondary amine- or hydroxyl-comprising biologically active moieties and pharmaceutically acceptable salts thereof, prodrug reagents, pharmaceutical compositions comprising said prodrugs and the use of said prodrugs.

To enhance the physicochemical or pharmacokinetic properties of a drug in vivo such drug can be conjugated with a carrier. Typically, carriers in drug delivery are either used in a non-covalent fashion, with the drug physicochemically formulated into a solvent-carrier mixture, or by covalent attachment of a carrier reagent to one of the drug's functional groups.

However the non-covalent approach requires a highly efficient drug encapsulation to prevent uncontrolled, burst-type release of the drug. Restraining the diffusion of an unbound, water soluble drug molecule requires strong van der Waals contacts, frequently mediated through hydrophobic moieties and charged moieties for electrostatic binding. Many conformationally sensitive drugs, such as proteins or peptides, are rendered dysfunctional during the encapsulation process and/or during subsequent storage of the encapsulated drug. Furthermore, dependence of the release mechanism of the drug upon biodegradation may cause interpatient variability.

Alternatively, a drug may be covalently conjugated to a carrier via a stable linker or via a reversible prodrug linker moiety from which the drug is released. If the drug is stably connected to the carrier, such conjugate needs to exhibit sufficient residual activity to have a pharmaceutical effect and the conjugate is constantly in an active form.

If the drug is conjugated to the carrier through a reversible prodrug linker, such conjugates are referred to as carrier-linked prodrugs. The advantage of such approach is that no residual activity of the conjugate is needed, because the drug exhibits its pharmacological effect upon release from the conjugate. A carrier-linked prodrug may exhibit no or little drug activity, i.e. carrier-linked prodrug is pharmacologically inactive. This approach is applied to various classes of molecules, from so-called small molecules, through natural products up to large proteins.

The biologically active moiety of such a carrier-linked prodrug can be released by enzymatic or non-enzymatic cleavage of the linkage between the carrier and the biologically active moiety, or by a sequential combination of both. However, enzyme-dependence is usually less preferred, because enzyme levels may vary significantly between patients which makes the correct dosing difficult.

Various non-enzymatically cleavable reversible prodrug linkers are known in the art, such as for example those disclosed in WO2005/099768 A2, WO2006/136586 A2, WO2009/095479 A2, WO2011/012722 A1, WO2011/089214 A1, WO2011/089216 A1 and WO2011/089215 A1.

In some cases the chain connecting the biologically active moiety with the spacer and/or carrier does not comprise the same type of linkage that is used to connect the biologically active moiety to the reversible prodrug linker. In other words, it may be advantageous to avoid the presence of, for example, ester linkages within the reversible prodrug moiety, if the biologically active moiety is connected to said reversible prodrug moiety through an ester linkage. Under certain circumstances the presence of such second ester linkage may potentially lead to a small amount of linker cleavage at the second ester linkage and not at the ester connecting the biologically active moiety to the reversible linker moiety. This is undesired, because in such case the drug would not be released in its native form, but with a small tag attached.

It is therefore an object of the present invention to at least partially overcome the above-mentioned disadvantage.

This object is achieved with a prodrug or a pharmaceutically acceptable salt thereof comprising a conjugate D-L, wherein -D is a primary or secondary amine- or hydroxyl-comprising biologically active moiety; and -L comprises, preferably consists of, a linker moiety -$L^1$ represented by formula (I)

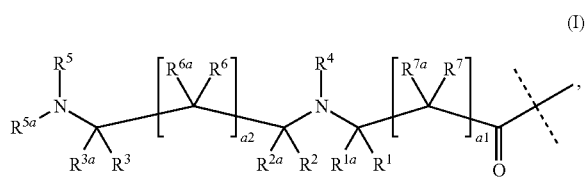

(I)

wherein the dashed line indicates attachment to the primary or secondary amine or hydroxyl of the biologically active moiety by forming an amide or ester linkage, respectively;

$R^1$, $R^{1a}$, $R^2$, $R^{2a}$, $R^3$ and $R^{3a}$ are independently of each other selected from the group consisting of —H, —C($R^8 R^{8a} R^{8b}$), —C(=O)$R^8$, —C≡N, —C(=N$R^8$)$R^{8a}$, —C$R^8$(=C$R^{8a}R^{8b}$), —C≡C$R^8$ and -T;

$R^4$, $R^5$ and $R^{5a}$ are independently of each other selected from the group consisting of —H, —C($R^9 R^{9a} R^{9b}$) and -T;

a1 and a2 are independently of each other 0 or 1;

each $R^6$, $R^{6a}$, $R^7$, $R^{7a}$, $R^8$, $R^{8a}$, $R^{8b}$, $R^9$, $R^{9a}$, $R^{9b}$ are independently of each other selected from the group consisting of —H, halogen, —CN, —COO$R^{10}$, —O$R^{10}$, —C(O)$R^{10}$, —C(O)N($R^{10}R^{10a}$), —S(O)$_2$N($R^{10}R^{10a}$), —S(O) N($R^{10}R^{10a}$), —S(O)$_2R^{10}$, —S(O)$R^{10}$, —N($R^{10}$)S (O)$_2$N($R^{10a}R^{10b}$), —S$R^{10}$, —N($R^{10}R^{10a}$), —NO$_2$, —OC(O) $R^{10}$, —N($R^{10}$)C(O)$R^{10a}$, —N($R^{10}$)S(O)$_2R^{10a}$, —N($R^{10}$)S (O)$R^{10a}$, —N($R^{10}$)C(O)O$R^{10a}$, —N($R^{10}$)C(O)N($R^{10a}R^{10b}$), —OC(O)N($R^{10}R^{10a}$), -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more $R^{11}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{12}$)—, —S(O)$_2$N($R^{12}$)—, —S(O)N($R^{12}$)—, —S(O)$_2$—, —S(O)—, —N($R^{12}$)S(O)$_2$N($R^{12a}$)—, —S—, —N($R^{12}$)—, —OC (O$R^{12}$)($R^{12a}$)—, —N($R^{12}$)C(O)N($R^{12a}$)—, and —OC(O)N ($R^{12}$)—;

each $R^{10}$, $R^{10a}$, $R^{10b}$ is independently selected from the group consisting of —H, -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more $R^{11}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{12}$)—, —S(O)$_2$N($R^{12}$)—, —S(O)N($R^{12}$)—, —S(O)$_2$—, —S(O)—, —N(R$^{12}$)S(O)$_2$N(R$^{12a}$)—, —S—, —N(R$^{12}$)—, —OC(OR$^{12}$)(R$^{12a}$)—, —N(R$^{12}$)C(O)N(R$^{12a}$)—, and —OC(O)N(R$^2$)—;

each T is independently of each other selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T is independently optionally substituted with one or more R$^{11}$, which are the same or different;

each R$^{11}$ is independently of each other selected from halogen, —CN, oxo (=O), —COOR$^{13}$, —OR$^{13}$, —C(O)R$^{13}$, —C(O)N(R$^{13}$R$^{13a}$), —S(O)$_2$N(R$^{13}$R$^{13a}$), —S(O)N(R$^{13}$R$^{13a}$), —S(O)$_2$R$^{13}$, —S(O)R$^{13}$, —N(R$^{13}$)S(O)$_2$N(R$^{13a}$R$^{13b}$), —SR$^{13}$, —N(R$^{13}$R$^{13a}$), —NO$_2$, —OC(O)R$^{13}$, —N(R$^{13}$)C(O)R$^{13a}$, —N(R$^{13}$)S(O)$_2$R$^{13a}$, —N(R$^{13}$)S(O)R$^{13a}$, —N(R$^{13}$)C(O) OR$^{13a}$, —N(R$^{13}$)C(O)N(R$^{13a}$R$^{13b}$), —OC(O)N(R$^{13}$R$^{13a}$), and C$_{1-6}$ alkyl; wherein C$_{1-6}$ alkyl is optionally substituted with one or more halogen, which are the same or different;

each R$^{12}$, R$^{12a}$, R$^{13}$, R$^{13a}$, R$^{13b}$ is independently selected from the group consisting of —H, and C$_{1-6}$ alkyl; wherein C$_{1-6}$ alkyl is optionally substituted with one or more halogen, which are the same or different;

Optionally, one or more of the pairs R$^1$/R$^{1a}$, R$^2$/R$^{2a}$, R$^3$/R$^{3a}$, R$^6$/R$^{6a}$, R$^7$/R$^{7a}$ are joined together with the atom to which they are attached to form a C$_{3-10}$ cycloalkyl or a 3- to 10-membered heterocyclyl;

Optionally, one or more of the pairs R$^1$/R$^2$, R$^1$/R$^3$, R$^1$/R$^4$, R$^1$/R$^5$, R$^1$/R$^6$, R$^1$/R$^7$, R$^2$/R$^3$, R$^2$/R$^4$, R$^2$/R$^5$, R$^2$/R$^6$, R$^2$/R$^7$, R$^3$/R$^4$, R$^3$/R$^5$, R$^3$/R$^6$, R$^3$/R$^7$, R$^4$/R$^5$, R$^4$/R$^6$, R$^4$/R$^7$, R$^5$/R$^6$, R$^5$/R$^7$, R$^6$/R$^7$ are joint together with the atoms to which they are attached to form a ring A;

A is selected from the group consisting of phenyl; naphthyl; indenyl; indanyl; tetralinyl; C$_{3-10}$ cycloalkyl; 3- to 10-membered heterocyclyl; and 8- to 11-membered heterobicyclyl;

wherein -L$^1$ is substituted with one to five moieties -L$^2$-Z, preferably -L$^1$ is substituted with one moiety -L$^2$-Z, and is optionally further substituted; wherein -L$^2$- is a single chemical bond or a spacer moiety; and —Z is a carrier moiety.

If one or both of R$^5$ and R$^{5a}$ are other than —H, it is preferred that they are connected to the nitrogen of moiety

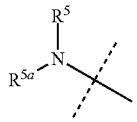

through an SP$^3$-hybridized carbon atom.

It was surprisingly found that prodrugs comprising the reversible prodrug linker moiety L$^1$ of formula (I) or their pharmaceutically acceptable salts release their biologically active moiety with advantageous properties, such as without releasing undesired side products and with a favourable pH dependency of the release.

Within the present invention the terms are used with the meaning as follows:

The term "drug" as used herein refers to a substance used in the treatment, cure, prevention, or diagnosis of a disease or used to otherwise enhance physical or mental well-being. If a drug is conjugated to another moiety, the part of the resulting product that originated from the drug is referred to as "biologically active moiety".

It is understood that the term "primary or secondary amine-comprising drug" refers to a drug having at least one primary or secondary amine functional group, which primary or secondary amine-comprising drug may optionally have one or more further functional group(s) including one or more additional primary and/or secondary amine functional group(s). If such primary or secondary amine-comprising drug is conjugated to, for example, a moiety -L$^1$, it is referred to as "primary or amine-comprising biologically active moiety", even though it is understood that said primary or secondary amine functional group became part of the amide bond connecting both moieties. The term "hydroxyl-comprising drug" and "hydroxyl-comprising biologically active moiety" are used accordingly: It is understood that the term "hydroxyl-comprising drug" refers to a drug having at least one hydroxyl functional group, which hydroxyl-comprising drug may optionally have one or more further functional group(s) including one or more additional hydroxyl group(s). If such hydroxyl-comprising drug is conjugated to, for example, a moiety -L$^1$, it is referred to as "hydroxyl-comprising biologically active moiety", even though it is understood that said hydroxyl functional group became part of the ester bond connecting both moieties. An alternative term for "primary or secondary amine-comprising biologically active moiety" is "primary or secondary amine-comprising drug moiety". Analogously, an alternative term for "hydroxyl-comprising biologically active moiety" is "hydroxyl-comprising drug moiety".

As used herein the term "prodrug" or "carrier-linked prodrug" refers to a biologically active moiety reversibly and covalently connected to a specialized protective group through a reversible prodrug linker moiety comprising a reversible linkage with the biologically active moiety to alter or to eliminate undesirable properties in the parent molecule. This also includes the enhancement of desirable properties in the drug and the suppression of undesirable properties. The specialized non-toxic protective group is referred to as "carrier". A prodrug releases it reversibly and covalently bound biologically active moiety in the form of its corresponding drug.

A "biodegradable linkage" or a "reversible linkage" is a linkage that is hydrolytically degradable, i.e. cleavable, in the absence of enzymes under physiological conditions (aqueous buffer at pH 7.4, 37° C.) with a half-life ranging from one hour to twelve months.

In contrast, a "permanent linkage" is not hydrolytically degradable, i.e. cleavable, in the absence of enzymes under physiological conditions (aqueous buffer at pH 7.4, 37° C.) with a half-life of less than twelve months.

As used herein, the term "traceless prodrug linker" means a reversible prodrug linker which upon cleavage releases the drug in its free form. As used herein, the term "free form" of a drug means the drug in its unmodified, pharmacologically active form. The reversible prodrug linker of the present invention, L$^1$, is a traceless prodrug linker.

As used herein, the term "excipient" refers to a diluent, adjuvant, or vehicle with which the therapeutic is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, mannitol, trehalose, gelatin, malt, rice, flour, chalk, silica gel, sodium stearate, glycerol monostearate, talc, sodium chloride, dried skim milk, glycerol, propylene, glycol, water, ethanol and the like. The pharmaceutical composition, if desired, can also contain minor amounts of wetting or emulsifying agents, pH buffering agents, like, for example, acetate, succinate, tris, carbonate, phosphate, HEPES (4-(2-hydroxyethyl)-1-piperazineethanesulfonic acid), MES (2-(N-morpholino)ethanesulfonic acid), or can contain detergents, like Tween, poloxamers, poloxamines, CHAPS, Igepal, or amino acids like, for example, glycine, lysine, or histidine. These pharmaceutical compositions can take the form of solutions, suspensions, emulsions, tablets, pills, capsules, powders, sustained-release formulations and the like. The pharmaceutical composition can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Such compositions will contain a therapeutically effective amount of the drug or biologically active moiety, together with a suitable amount of excipient so as to provide the form for proper administration to the patient. The formulation should suit the mode of administration.

As used herein, the term "hydrogel" means a hydrophilic or amphiphilic polymeric network composed of homopolymers or copolymers, which is insoluble due to the presence of covalent chemical crosslinks. The crosslinks provide the network structure and physical integrity. Hydrogels exhibit a thermodynamic compatibility with water which allows them to swell in aqueous media.

As used herein, the term "reagent" means a chemical compound which comprises at least one functional group for reaction with the functional group of another chemical compound or drug. It is understood that a drug comprising a functional group (such as a primary or secondary amine or hydroxyl functional group) is also a reagent.

As used herein, the term "backbone reagent" means a reagent, which is suitable as a starting material for forming hydrogels. As used herein, a backbone reagent preferably does not comprise biodegradable linkages. A backbone reagent may comprise a "branching core" which term refers to an atom or moiety to which more than one other moiety is attached.

As used herein, the term "crosslinker reagent" means a linear or branched reagent, which is suitable as a starting material for crosslinking backbone reagents. Preferably, the crosslinker reagent is a linear chemical compound. A crosslinker reagent preferably comprises at least one biodegradable linkage.

As used herein, the term "moiety" means a part of a molecule, which lacks one or more atom(s) compared to the corresponding reagent. If, for example, a reagent of the formula "H—X—H" reacts with another reagent and becomes part of the reaction product, the corresponding moiety of the reaction product has the structure "H—X—" or "—X—", whereas each "—" indicates attachment to another moiety. Accordingly, a biologically active moiety is released from a prodrug as a drug.

Accordingly, the phrase "in bound form" is used to refer to the corresponding moiety of a reagent, i.e. "lysine in bound form" refers to a lysine moiety which lacks one or more atom(s) of the lysine reagent and is part of a molecule.

It is understood that if the sequence or chemical structure of a group of atoms is provided which group of atoms is attached to two moieties or is interrupting a moiety, said sequence or chemical structure can be attached to the two moieties in either orientation, unless explicitly stated otherwise. For example, a moiety "—C(O)N(R$^{12}$)—" can be attached to two moieties or interrupting a moiety either as "—C(O)N(R$^{12}$)—" or as "—N(R$^{12}$)C(O)—". Similarly, a moiety

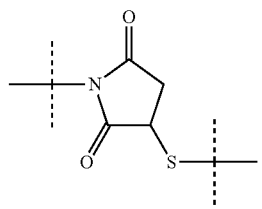

can be attached to two moieties or can interrupt a moiety either as

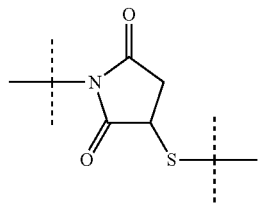

or as

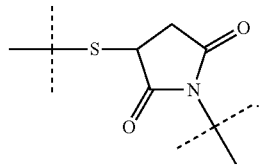

As used herein, the term "functional group" means a group of atoms which can react with other groups of atoms. Functional groups include but are not limited to the following groups: carboxylic acid (—(C═O)OH), primary or secondary amine (—NH$_2$, —NH—), maleimide, thiol (—SH), sulfonic acid (—(O═S═O)OH), carbonate, carbamate (—O(C═O)N<), hydroxyl (—OH), aldehyde (—(C═O)H), ketone (—(C═O)—), hydrazine (>N—N<), isocyanate, isothiocyanate, phosphoric acid (—O(P═O)OHOH), phosphonic acid (—O(P═O)OHH), haloacetyl, alkyl halide, acryloyl, aryl fluoride, hydroxylamine, disulfide, vinyl sulfone, vinyl ketone, diazoalkane, oxirane, and aziridine.

As used herein, the term "activated functional group" means a functional group, which is connected to an activating group, i.e. a functional group was reacted with an activating reagent. Preferred activated functional groups include but are not limited to activated ester groups, activated carbamate groups, activated carbonate groups and activated thiocarbonate groups. Preferred activating groups are selected from formulas (f-i) to (f-vii):

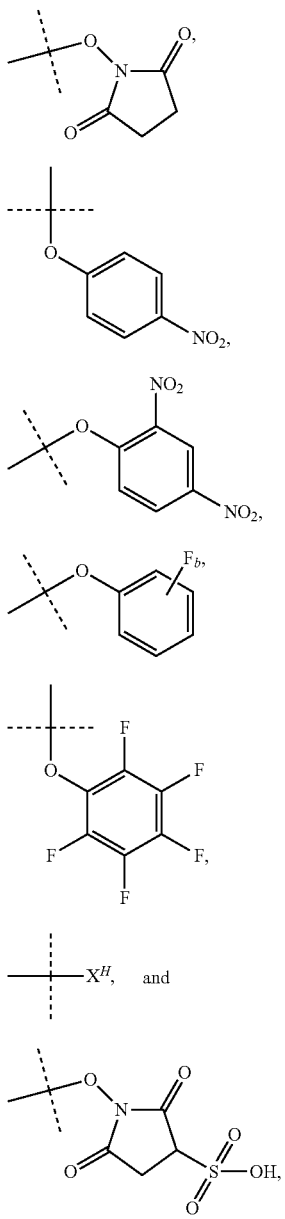

wherein
the dashed lines indicate attachment to the rest of the molecule;
b is 1, 2, 3 or 4; and
$X^H$ is Cl, Br, I, or F.

Accordingly, a preferred activated ester has the formula

—(C=O)—$X^F$, wherein
$X^F$ is selected from formula (f-i), (f-ii), (f-iii), (f-iv), (f-v), (f-vi) and (f-vii).

Accordingly, a preferred activated carbamate has the formula

—N—(C=O)—$X^F$, wherein
$X^F$ is selected from formula (f-i), (f-ii), (f-iii), (f-iv), (f-v), (f-vi) and (f-vii).

Accordingly, a preferred activated carbonate has the formula

—O—(C=O)—$X^F$, wherein
$X^F$ is selected from formula (f-i), (f-ii), (f-iii), (f-iv), (f-v), (f-vi) and (f-vii).

Accordingly, a preferred activated thioester has the formula

—S—(C=O)—$X^F$, wherein
$X^F$ is selected from formula (f-i), (f-ii), (f-iii), (f-iv), (f-v), (f-vi) and (f-vii).

Accordingly, an "activated end functional group" is an activated functional group which is localized at the end of a moiety or molecule, i.e. is a terminal activated functional group.

As used herein, the term "capping group" means a moiety which is irreversibly, i.e. permanently, connected to a functional group to render it incapable of reacting with functional groups of other reagents or moieties.

As used herein, the term "protecting group" means a moiety which is reversibly connected to a functional group to render it incapable of reacting with, for example, another functional group. Suitable alcohol (—OH) protecting groups are, for example, acetyl, benzoyl, benzyl, β-methoxyethoxymethyl ether, dimethoxytrityl, methoxymethyl ether, methoxytrityl, p-methoxybenzyl ether, methylthiomethyl ether, pivaloyl, tetrahydropyranyl, trityl, trimethylsilyl, tert-butyldimethylsilyl, tri-iso-propylsilyloxymethyl, triisopropylsilyl ether, methyl ether, and ethoxyethyl ether. Suitable amine protecting groups are, for example, ortho nitrobenzosulfonyl, carbobenzyloxy, p-methoxybenzyl carbonyl, tert-butyloxycarbonyl, 9-fluorenylmethyloxyarbonyl, acetyl, benzoyl, benzyl, carbamate, p-methoxybenzyl, 3,4-dimethoxybenzyl, p-methoxyphenyl, and tosyl. Suitable carbonyl protecting groups are, for example, acetals and ketals, acylals and dithianes. Suitable carboxylic acid protecting groups are, for example, methyl esters, benzyl esters, tert-butyl esters, 2,6-dimethylphenol, 2,6-diisopropylphenol, 2,6.-di-tert-butylphenol, silyl esters, orthoesters, and oxazoline. Suitable phosphate protecting groups are, for example, 2-cyanoethyl and methyl.

In case the compounds according to formula (I) contain one or more acidic or basic groups, the invention also comprises their corresponding pharmaceutically or toxicologically acceptable salts, in particular their pharmaceutically utilizable salts. Thus, the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. For the person skilled in the art further methods are known for converting the basic group into a cation like the alkylation of an amine group resulting in a positively-charge ammonium group and an appropriate counterion of the salt. If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (I) which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means approved by a regulatory agency such as the EMEA (Europe) and/or the FDA (US) and/or any other national regulatory agency for use in animals, preferably in humans.

As used herein the term "small molecule biologically active moiety" refers to an organic biologically active moiety having a molecular weight of less than 1000 Da, such as less than 900 Da or less than 800 Da.

As used herein, the term "oligonucleotide" refers to double- or single-stranded RNA and DNA with preferably 2 to 1000 nucleotides and any modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited, to 2'-position sugar modifications, 5-position pyrimidine modifications, 8-position purine modifications, modifications at exocyclic amines, substitution of 4-thiouridines, substitution of 5-bromo or 5-iodo-uracil; backbone modifications, methylations, unusual base-pairing combinations such as the isobases isocytidine and isoguanidine and the like. Modifications can also include 3' and 5' modifications such as capping and change of stereochemistry. The term also includes aptamers.

The term "peptide nucleic acids" refers to organic polymers having a peptidic backbone, i.e. a backbone in which the monomers are connected to each other through peptide linkages, to which nucleobases, preferably adenine, cytosine, guanine, thymine and uracil, are attached. A preferred backbone comprises N-(2-aminoethyl)-glycine.

The term "peptide" as used herein refers to a chain of at least 2 and up to and including 50 amino acid monomer moieties linked by peptide (amide) linkages. The term "peptide" also includes peptidomimetics, such as D-peptides, peptoids or beta-peptides, and covers such peptidomimetic chains with up to and including 50 monomer moieties.

As used herein, the term "protein" refers to a chain of more than 50 amino acid monomer moieties linked by peptide linkages, in which preferably no more than 12000 amino acid monomers are linked by peptide linkages, such as no more than 10000 amino acid monomer moieties, no more than 8000 amino acid monomer moieties, no more than 5000 amino acid monomer moieties or no more than 2000 amino acid monomer moieties.

As used herein, the term "polymer" means a molecule comprising repeating structural units, i.e. the monomers, connected by chemical bonds in a linear, circular, branched, crosslinked or dendrimeric way or a combination thereof, which may be of synthetic or biological origin or a combination of both. It is understood that a polymer may also comprise one or more other chemical group(s) and/or moiety/moieties, such as, for example, one or more functional group(s). Preferably, a soluble polymer has a molecular weight of at least 0.5 kDa, e.g. a molecular weight of at least 1 kDa, a molecular weight of at least 2 kDa, a molecular weight of at least 3 kDa or a molecular weight of at least 5 kDa. If the polymer is soluble, it preferable has a molecular weight of at most 1000 kDa, such as at most 750 kDa, such as at most 500 kDa, such as at most 300 kDa, such as at most 200 kDa, such as at most 100 kDa. It is understood that for insoluble polymers, such as hydrogels, no meaningful molecular weight ranges can be provided.

As used herein, the term "polymeric" means a reagent or a moiety comprising one or more polymer(s).

The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers. As used herein, the term "number average molecular weight" means the ordinary arithmetic means of the molecular weights of the individual polymers.

As used herein, the term "polymerization" or "polymerizing" means the process of reacting monomer or macromonomer reagents in a chemical reaction to form polymer chains or networks, including but not limited to hydrogels.

As used herein, the term "macromonomer" means a molecule that was obtained from the polymerization of monomer reagents.

As used herein, the term "condensation polymerization" or "condensation reaction" means a chemical reaction, in which the functional groups of two reagents react to form one single molecule, i.e. the reaction product, and a low molecular weight molecule, for example water, is released.

As used herein, the term "suspension polymerization" means a heterogeneous and/or biphasic polymerization reaction, wherein the monomer reagents are dissolved in a first solvent, forming the disperse phase which is emulsified in a second solvent, forming the continuous phase. In the present invention, the monomer reagents are the at least one backbone reagent and the at least one crosslinker reagent. Both the first solvent and the monomer reagents are not soluble in the second solvent. Such emulsion is formed by stirring, shaking, exposure to ultrasound or Microsieve™ emulsification, more preferably by stirring or Microsieve™ emulsification and more preferably by stirring. This emulsion is stabilized by an appropriate emulsifier. The polymerization is initiated by addition of a base as initiator which is soluble in the first solvent. A suitable commonly known base suitable as initiator may be a tertiary base, such as tetramethylethylenediamine (TMEDA).

As used herein, the term "immiscible" means the property where two substances are not capable of combining to form a homogeneous mixture.

As used herein, the term "polyamine" means a reagent or moiety comprising more than one amine (—NH— and/or —NH$_2$), e.g. from 2 to 64 amines, from 4 to 48 amines, from 6 to 32 amines, from 8 to 24 amines, or from 10 to 16 amines. Particularly preferred polyamines comprise from 2 to 32 amines.

As used herein, the term "hydrogel" means a hydrophilic or amphiphilic polymeric network composed of homopolymers or copolymers, which is insoluble due to the presence of covalent chemical crosslinks. The crosslinks provide the network structure and physical integrity.

As used herein, the term "PEG-based comprising at least X % PEG" in relation to a moiety or reagent means that said moiety or reagent comprises at least X % (w/w) ethylene glycol units (—$CH_2CH_2O$—), wherein the ethylene glycol units may be arranged blockwise, alternating or may be randomly distributed within the moiety or reagent and preferably all ethylene glycol units of said moiety or reagent are present in one block; the remaining weight percentage of the PEG-based moiety or reagent are other moieties preferably selected from the following moieties and linkages:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

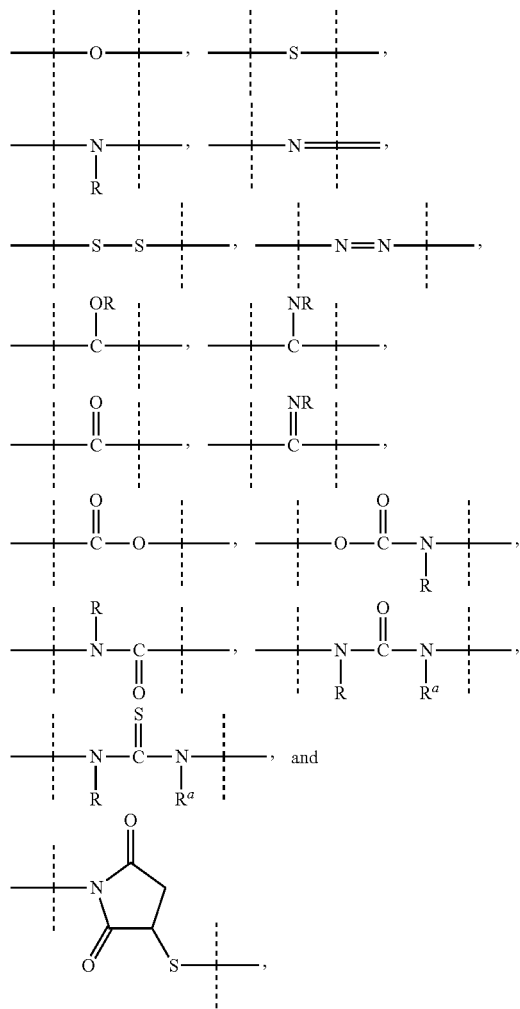

wherein dashed lines indicate attachment to the remainder of the moiety or reagent, and R and $R^a$ are independently of each other selected from the group consisting of H, methyl, ethyl, propyl, butyl, pentyl and hexyl.

The term "hyaluronic acid-based comprising at least X % hyaluronic acid" is used accordingly.

The term "substituted" as used herein means that one or more —H atom(s) of a molecule or moiety are replaced by a different atom or a group of atoms, which are referred to as "substituent".

Preferably, the one or more further optional substituents are independently of each other selected from the group consisting of halogen, —CN, —COOR$^{x1}$, —OR$^{x1}$, —C(O) R$^{x1}$, —C(O)N(R$^{x1}$R$^{x1a}$), —S(O)$_2$N(R$^{x1}$R$^{x1a}$), —S(O)N (R$^{x1}$R$^{x1a}$), —S(O)$_2$R$^{x1}$, —S(O)R$^{x1}$, —N(R$^{x1}$)S(O)$_2$N (R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O) R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, $C_{1-50}$ alkyl, $C_{2-50}$ alkenyl, and $C_{2-50}$ alkynyl; wherein -T$^0$, $C_{1-50}$ alkyl, $C_{2-50}$ alkenyl, and $C_{2-50}$ alkynyl are optionally substituted with one or more R$^{x2}$, which are the same or different and wherein $C_{1-50}$ alkyl, $C_{2-50}$ alkenyl, and $C_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC (OR$^{x3}$)(R$^{x3a}$)—, —N(R$^{x3}$)C(O)N(R$^{x3a}$)—, and —OC(O)N (R$^{x3}$)—;

R$^{x1}$, R$^{x1a}$, R$^{x1b}$ are independently of each other selected from the group consisting of —H, -T$^0$, $C_{1-50}$ alkyl, $C_{2-50}$ alkenyl, and $C_{2-50}$ alkynyl; wherein -T$^0$, $C_{1-50}$ alkyl, $C_{2-50}$ alkenyl, and $C_{2-50}$ alkynyl are optionally substituted with one or more R$^{x2}$, which are the same or different and wherein $C_{1-50}$ alkyl, $C_{2-50}$ alkenyl, and $C_{2-50}$ alkynyl are optionally interrupted by one or more groups selected from the group consisting of -T$^0$-, —C(O)O—, —O—, —C(O)—, —C(O) N(R$^{x3}$)—, —S(O)$_2$N(R$^{x3}$)—, —S(O)N(R$^{x3}$)—; —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC (O)N(R$^{x3}$)—;

each T$^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T$^0$ is independently optionally substituted with one or more R$^{x2}$, which are the same or different;

each R$^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$) S(O)$_2$N(R$^{x4a}$R$^{x4b}$), —SR$^{x4}$, —N(R$^{x4}$R$^{x4a}$), —NO$_2$, —OC (O)R$^{x4}$, —N(R$^{x4}$) C(O)R$^{x4a}$, —N(R$^{x4}$)S(O)$_2$R$^{x4a}$, —N(R$^{x4}$) S(O)R$^{x4a}$, —N(R$^{x4}$)C(O)OR$^{x4a}$, —N(R$^{x4}$)C(O)N (R$^{x4a}$R$^{x4b}$), —OC(O)N(R$^{x4}$R$^{x4a}$), and $C_{1-6}$ alkyl; wherein $C_{1-6}$ alkyl is optionally substituted with one or more halogen, which are the same or different;

each R$^{x3}$, R$^{x3a}$, R$^{x4}$, R$^{x4a}$, R$^{x4b}$ is independently selected from the group consisting of —H and $C_{1-6}$ alkyl; wherein $C_{1-6}$ alkyl is optionally substituted with one or more halogen, which are the same or different.

More preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$) S(O)$_2$N(R$^{x1a}$R$^{x1b}$), —SR$^{x1}$, —N(R$^{x1}$R$^{x1a}$), —NO$_2$, —OC (O)R$^{x1}$, —N(R$^{x1}$)C(O)R$^{x1a}$, —N(R$^{x1}$)S(O)$_2$R$^{x1a}$, —N(R$^{x1}$)

S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, C$_{1-10}$ alkyl, C$_{2-10}$ alkenyl, and C$_{2-10}$ alkynyl; wherein -T$^0$, C$_{1-10}$ alkyl, C$_{2-10}$ alkenyl, and C$_{2-10}$ alkynyl are optionally substituted with one or more R$^{x2}$, which are the same or different and wherein C$_{1-10}$ alkyl, C$_{2-10}$ alkenyl, and C$_{2-10}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each R$^{x1}$, R$^{x1a}$, R$^{x1b}$, R$^{x3}$, R$^{x3a}$ is independently selected from the group consisting of —H, halogen, C$_{1-6}$ alkyl, C$_{2-6}$ alkenyl, and C$_{2-6}$ alkynyl;

each T$^0$ is independently selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T$^0$ is independently optionally substituted with one or more R$^{x2}$, which are the same or different;

each R$^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and C$_{1-6}$ alkyl; wherein C$_{1-6}$ alkyl is optionally substituted with one or more halogen, which are the same or different;

each R$^{x4}$, R$^{x4a}$, R$^{x4b}$ is independently selected from the group consisting of —H, halogen, C$_{1-6}$ alkyl, C$_{2-6}$ alkenyl, and C$_{2-6}$ alkynyl;

Even more preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, C$_{1-6}$ alkyl, C$_{2-6}$ alkenyl, and C$_{2-6}$ alkynyl; wherein -T$^0$, C$_{1-6}$ alkyl, C$_{2-6}$ alkenyl, and C$_{2-6}$ alkynyl are optionally substituted with one or more R$^{x2}$, which are the same or different and wherein C$_{1-6}$ alkyl, C$_{2-6}$ alkenyl, and C$_{2-6}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each R$^{x1}$, R$^{x1a}$, R$^{x1b}$, R$^{x2}$, R$^{x3}$, R$^{x3a}$ is independently selected from the group consisting of —H, halogen, C$_{1-6}$ alkyl, C$_{2-6}$ alkenyl, and C$_{2-6}$ alkynyl;

each T$^0$ is independently selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T$^0$ is independently optionally substituted with one or more R$^{x2}$, which are the same or different.

Preferably, a maximum of 6 —H atoms of an optionally substituted molecule are independently replaced by a substituent, e.g. 5 —H atoms are independently replaced by a substituent, 4 —H atoms are independently replaced by a substituent, 3 —H atoms are independently replaced by a substituent, 2 —H atoms are independently replaced by a substituent, or 1 —H atom is replaced by a substituent.

The term "interrupted" means that a moiety is inserted between two carbon atoms or—if the insertion is at one of the moiety's ends—between a carbon and a hydrogen atom.

As used herein, the term "C$_{1-4}$ alkyl" alone or in combination means a straight-chain or branched alkyl moiety having 1 to 4 carbon atoms. If present at the end of a molecule, examples of straight-chain or branched C$_{1-4}$ alkyl are methyl, ethyl, n-propyl, isopropyl, n-butyl, isobutyl, sec-butyl and tert-butyl. When two moieties of a molecule are linked by the C$_{1-4}$ alkyl, then examples for such C$_{1-4}$ alkyl groups are —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—. Each hydrogen of a C$_{1-4}$ alkyl carbon may optionally be replaced by a substituent as defined above. Optionally, a C$_{1-4}$ alkyl may be interrupted by one or more moieties as defined below.

As used herein, the term "C$_{1-6}$ alkyl" alone or in combination means a straight-chain or branched alkyl moiety having 1 to 6 carbon atoms. If present at the end of a molecule, examples of straight-chain and branched C$_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the C$_{1-6}$ alkyl group, then examples for such C$_{1-6}$ alkyl groups are —CH$_2$—, —CH$_2$—CH$_2$—, —CH(CH$_3$)—, —CH$_2$—CH$_2$—CH$_2$—, —CH(C$_2$H$_5$)— and —C(CH$_3$)$_2$—. Each hydrogen atom of a C$_{1-6}$ carbon may optionally be replaced by a substituent as defined above. Optionally, a C$_{1-6}$ alkyl may be interrupted by one or more moieties as defined below.

Accordingly, "C$_{1-10}$ alkyl", "C$_{1-20}$ alkyl" or "C$_{1-50}$ alkyl" means an alkyl chain having 1 to 10, 1 to 20 or 1 to 50 carbon atoms, respectively, wherein each hydrogen atom of the C$_{1-10}$, C$_{1-20}$ or C$_{1-50}$ carbon may optionally be replaced by a substituent as defined above. Optionally, a C$_{1-10}$ or C$_{1-50}$ alkyl may be interrupted by one or more moieties as defined below.

As used herein, the term "C$_{2-6}$ alkenyl" alone or in combination means a straight-chain or branched hydrocarbon moiety comprising at least one carbon-carbon double bond having 2 to 6 carbon atoms. If present at the end of a molecule, examples are —CH=CH$_2$, —CH=CH—CH$_3$, —CH$_2$—CH=CH$_2$, —CH=CHCH$_2$—CH$_3$ and —CH=CH—CH=CH$_2$. When two moieties of a molecule are linked by the C$_{2-6}$ alkenyl group, then an example for such C$_{2-6}$ alkenyl is —CH=CH—. Each hydrogen atom of a C$_{2-6}$ alkenyl moiety may optionally be replaced by a substituent as defined above. Optionally, a C$_{2-6}$ alkenyl may be interrupted by one or more moieties as defined below.

Accordingly, the term "C$_{2-10}$ alkenyl", "C$_{2-20}$ alkenyl" or "C$_{2-50}$ alkenyl" alone or in combination means a straight-chain or branched hydrocarbon moiety comprising at least one carbon-carbon double bond having 2 to 10, 2 to 20 or 2 to 50 carbon atoms. Each hydrogen atom of a C$_{2-10}$ alkenyl, C$_{2-20}$ alkenyl or C$_{2-50}$ alkenyl group may optionally be replaced by a substituent as defined above. Optionally, a C$_{2-10}$ alkenyl, C$_{2-20}$ alkenyl or C$_{2-50}$ alkenyl may be interrupted by one or more moieties as defined below.

As used herein, the term "C$_{2-6}$ alkynyl" alone or in combination means straight-chain or branched hydrocarbon moiety comprising at least one carbon-carbon triple bond having 2 to 6 carbon atoms. If present at the end of a molecule, examples are —C≡CH, —CH$_2$—C≡CH, CH$_2$—

$CH_2$—C≡CH and $CH_2$—C≡C—$CH_3$. When two moieties of a molecule are linked by the alkynyl group, then an example is —C≡C—. Each hydrogen atom of a $C_{2-6}$ alkynyl group may optionally be replaced by a substituent as defined above. Optionally, one or more double bond(s) may occur. Optionally, a $C_{2-6}$ alkynyl may be interrupted by one or more moieties as defined below.

Accordingly, as used herein, the term "$C_{2-10}$ alkynyl", "$C_{2-20}$ alkynyl" and "$C_{2-50}$ alkynyl" alone or in combination means a straight-chain or branched hydrocarbon moiety comprising at least one carbon-carbon triple bond having 2 to 10, 2 to 20 or 2 to 50 carbon atoms, respectively. Each hydrogen atom of a $C_{2-10}$ alkynyl, $C_{2-20}$ alkynyl or $C_{2-50}$ alkynyl group may optionally be replaced by a substituent as defined above. Optionally, one or more double bond(s) may occur. Optionally, a $C_{2-10}$ alkynyl, $C_{2-20}$ alkynyl or $C_{2-50}$ alkynyl may be interrupted by one or more moieties as defined below.

As mentioned above, a $C_{1-4}$ alkyl, $C_{1-6}$ alkyl, $C_{1-10}$ alkyl, $C_{1-20}$ alkyl, $C_{1-50}$ alkyl, $C_{2-6}$ alkenyl, $C_{2-10}$ alkenyl, $C_{2-20}$ alkenyl, $C_{2-50}$ alkenyl, $C_{2-6}$ alkynyl, $C_{2-10}$ alkynyl, $C_{2-20}$ alkynyl or $C_{2-50}$ alkynyl may optionally be interrupted by one or more of the following moieties:

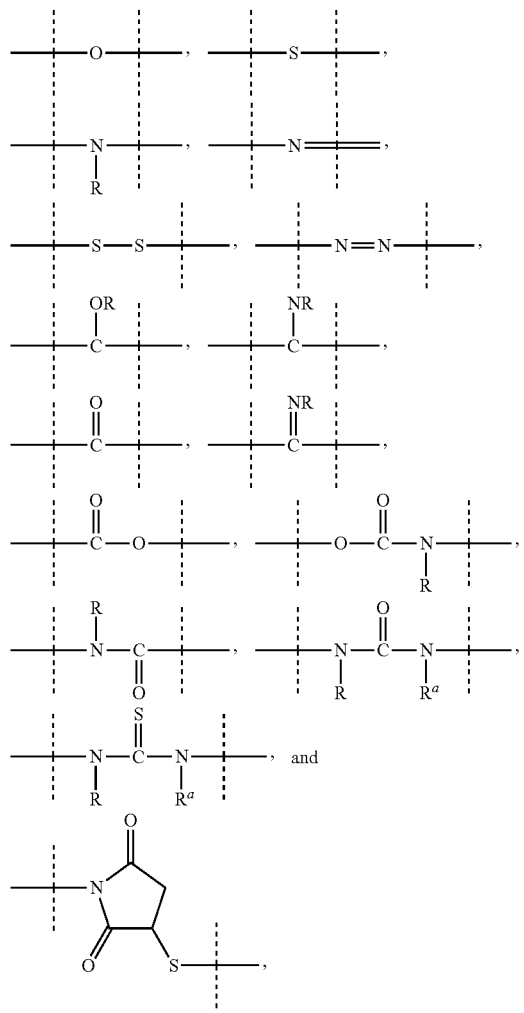

wherein
dashed lines indicate attachment to the remainder of the moiety or reagent; and R and $R^a$ are independently of each other selected from the group consisting of H, methyl, ethyl, propyl, butyl, pentyl and hexyl.

As used herein, the term "$C_{3-10}$ cycloalkyl" means a cyclic alkyl chain having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl or cyclodecyl. Each hydrogen atom of a $C_{3-10}$ cycloalkyl carbon may be replaced by a substituent as defined above. The term "$C_{3-10}$ cycloalkyl" also includes bridged bicycles like norbornane or norbornene.

The term "8- to 30-membered carbopolycyclyl" or "8- to 30-membered carbopolycycle" means a cyclic moiety of two or more rings with 8 to 30 ring atoms, where two neighboring rings share at least one ring atom and that may contain up to the maximum number of double bonds (aromatic or non-aromatic ring which is fully, partially or un-saturated). Preferably a 8- to 30-membered carbopolycyclyl means a cyclic moiety of two, three, four or five rings, more preferably of two, three or four rings.

As used herein, the term "3- to 10-membered heterocyclyl" or "3- to 10-membered heterocycle" means a ring with 3, 4, 5, 6, 7, 8, 9 or 10 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for 3- to 10-membered heterocycles include but are not limited to aziridine, oxirane, thiirane, azirine, oxirene, thiirene, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 3- to 10-membered heterocyclyl or 3- to 10-membered heterocyclic group may be replaced by a substituent as defined below.

As used herein, the term "8- to 11-membered heterobicyclyl" or "8- to 11-membered heterobicycle" means a heterocyclic moiety of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for an 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent as defined below.

Similarly, the term "8- to 30-membered heteropolycyclyl" or "8- to 30-membered heteropolycycle" means a heterocyclic moiety of more than two rings with 8 to 30 ring atoms, preferably of three, four or five rings, where two neighboring rings share at least one ring atom and that may contain up to the maximum number of double bonds (aromatic or non-aromatic ring which is fully, partially or unsaturated), wherein at least one ring atom up to 10 ring atoms are replaced by a heteroatom selected from the group of sulfur (including —S(O)—, —S(O)$_2$—), oxygen and nitrogen (including =N(O)—) and wherein the ring is linked to the rest of a molecule via a carbon or nitrogen atom.

It is understood that that phrase "the pair $R^1/R^{1a}$ is joined together with the atom to which they are attached to form a $C_{3-10}$ cycloalkyl or a 3- to 10-membered heterocyclyl" refers to a moiety having the following structure:

wherein R is the $C_{3-10}$ cycloalkyl or a 3- to 10-membered heterocyclyl. This applies analogously to the pairs $R^2/R^{2a}$, $R^3/R^{3a}$, $R^6/R^{6a}$ and $R^7/R^{7a}$.

It is understood that the phrase "the pair $R^1/R^7$ is joint together with the atoms to which they are attached to form a ring A" refers to a moiety having the following structure:

This applies analogously to the pairs $R^1/R^2$, $R^1/R^3$, $R^1/R^4$, $R^1/R^5$, $R^1/R^6$, $R^2/R^3$, $R^2/R^4$, $R^2/R^5$, $R^2/R^6$, $R^2/R^7$, $R^3/R^4$, $R^3/R^5$, $R^3/R^6$, $R^3/R^7$, $R^4/R^5$, $R^4/R^6$, $R^4/R^7$, $R^5/R^6$, $R^5/R^7$ and $R^6/R^7$.

As used herein, the term "terminal alkyne" means a moiety

As used herein, "halogen" means fluoro, chloro, bromo or iodo. It is generally preferred that halogen is fluoro or chloro.

In general, the term "comprise" or "comprising" also encompasses "consist of" or "consisting of".

In one embodiment -D of formula (I) is a primary or secondary amine-comprising biologically active moiety which is connected to -L$^1$ through an amide linkage.

In another embodiment -D of formula (I) is a hydroxyl-comprising biologically active moiety which is connected to -L$^1$ through an ester linkage.

-D of formula (I) is preferably a small molecule biologically active moiety, oligonucleotide moiety, peptide nucleic acid moiety, peptide moiety or protein moiety.

In one preferred embodiment -D of formula (I) is a small molecule biologically active moiety.

In another preferred embodiment -D of formula (I) is a peptide moiety.

In another preferred embodiment -D of formula (I) is a protein moiety, even more preferably a monoclonal or polyclonal antibody or fragment or fusion thereof.

Another aspect of the present invention is a prodrug reagent comprising a conjugate L'-Q, wherein
-Q is —OH or a leaving group; and
-L' comprises, preferably consists of, a linker moiety -L$^1$ represented by formula (I')

(I')

wherein
the dashed line indicates attachment to -Q;
$R^1$, $R^{1a}$, $R^2$, $R^{2a}$, $R^3$ and $R^{3a}$ are independently of each other selected from the group consisting of —H, —C($R^{8a}R^{8b}$), —C(=O)$R^8$, —C≡N, —C(=N$R^8$)$R^{8a}$, —CR$^8$(=CR$^{8a}R^{8b}$), —C≡CR$^8$ and -T;
$R^4$, $R^5$ and $R^{5a}$ are independently of each other selected from the group consisting of —H, —C($R^9R^{9a}R^{9b}$) and -T;
a1 and a2 are independently of each other 0 or 1;
each $R^6$, $R^{6a}$, $R^7$, $R^{7a}$, $R^8$, $R^{8a}$, $R^{8b}$, $R^9$, $R^{9a}$, $R^{9b}$ are independently of each other selected from the group consisting of —H, halogen, —CN, —COOR$^{10}$, —OR$^{10}$, —C(O)R$^{10}$, —C(O)N(R$^{10}$R$^{10a}$), —S(O)$_2$N(R$^{10}$R$^{10a}$), —S(O) N(R$^{10}$R$^{10a}$), —S(O)$_2$R$^{10}$, —S(O)R$^{10}$, —N(R$^{10}$)S(O)$_2$N(R$^{10a}$R$^{10b}$), —SR$^{10}$, —N(R$^{10}$R$^{10a}$), —NO$_2$, —OC(O)R$^{10}$, —N(R$^{10}$)C(O)R$^{10a}$, —N(R$^{10}$)S(O)$_2$R$^{10a}$, —N(R$^{10}$)S(O)R$^{10a}$, —N(R$^{10}$)C(O)OR$^{10a}$, —N(R$^{10}$)C(O)N(R$^{10a}$R$^{10b}$), —OC(O)N(R$^{10}$R$^{10a}$), -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more R$^{11}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N(R$^{12}$)—, —S(O)$_2$N(R$^{12}$)—, —S(O)N(R$^{12}$)—, —S(O)$_2$—, —S(O)—, —N(R$^{12}$)S(O)$_2$N(R$^{12a}$)—, —S—, —N(R$^{12}$)—, —OC(OR$^{12}$)(R$^{12a}$)—, —N(R$^{12}$)C(O)N(R$^{12a}$)—, and —OC(O)N(R$^{12}$)—;
each R$^{10}$, R$^{10a}$, R$^{10b}$ is independently selected from the group consisting of —H, -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more R$^{11}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N(R$^{12}$)—, —S(O)$_2$N(R$^{12}$)—, —S(O)N(R$^{12}$)—, —S(O)$_2$—, —S(O)—, —N(R$^{12}$)S(O)$_2$N(R$^{12a}$)—, —S—, —N(R$^{12}$)—, —OC(OR$^{12}$)(R$^{12a}$)—, —N(R$^{12}$)C(O)N(R$^{12a}$)—, and —OC(O)N(R$^{12}$)—;

each T is independently of each other selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T is independently optionally substituted with one or more R$^{11}$, which are the same or different;

each R$^{11}$ is independently of each other selected from halogen, —CN, oxo (=O), —COOR$^{13}$, —OR$^{13}$, —C(O)R$^{13}$, —C(O)N(R$^{13}$R$^{13a}$), —S(O)$_2$N(R$^{13}$R$^{13a}$), —S(O)N(R$^{13}$R$^{13a}$), —S(O)$_2$R$^{13}$, —S(O)R$^{13}$, —N(R$^{13}$)S(O)$_2$N(R$^{13a}$R$^{13b}$), —SR$^{13}$, —N(R$^{13}$R$^{13a}$), —NO$_2$, —OC(O)R$^{13}$, —N(R$^{13}$)C(O)R$^{13a}$, —N(R$^{13}$)S(O)$_2$R$^{13a}$, —N(R$^{13}$)S(O)R$^{13a}$, —N(R$^{13}$)C(O) OR$^{13a}$, —N(R$^{13}$)C(O)N(R$^{13a}$R$^{13b}$), —OC(O)N(R$^{13}$R$^{13a}$), and C$_{1-6}$ alkyl; wherein C$_{1-6}$ alkyl is optionally substituted with one or more halogen, which are the same or different;

each R$^{12}$, R$^{12a}$, R$^{13}$, R$^{13a}$, R$^{13b}$ is independently selected from the group consisting of —H, and C$_{1-6}$ alkyl; wherein C$_{1-6}$ alkyl is optionally substituted with one or more halogen, which are the same or different;

Optionally, one or more of the pairs R$^1$/R$^{1a}$, R$^2$/R$^{2a}$, R$^3$/R$^{3a}$, R$^6$/R$^{6a}$, R$^7$/R$^{7a}$ are joined together with the atom to which they are attached to form a C$_{3-10}$ cycloalkyl or a 3- to 10-membered heterocyclyl;

Optionally, one or more of the pairs R$^1$/R$^2$, R$^1$/R$^3$, R$^1$/R$^4$, R$^1$/R$^5$, R$^1$/R$^6$, R$^1$/R$^7$, R$^2$/R$^3$, R$^2$/R$^4$, R$^2$/R$^5$, R$^2$/R$^6$, R$^2$/R$^7$, R$^3$/R$^4$, R$^3$/R$^5$, R$^3$/R$^6$, R$^3$/R$^7$, R$^4$/R$^5$, R$^4$/R$^6$, R$^4$/R$^7$, R$^5$/R$^6$, R$^5$/R$^7$, R$^6$/R$^7$ are joint together with the atoms to which they are attached to form a ring A;

A is selected from the group consisting of phenyl; naphthyl; indenyl; indanyl; tetralinyl; C$_{3-10}$ cycloalkyl; 3- to 10-membered heterocyclyl; and 8- to 11-membered heterobicyclyl;

wherein -L$^1$ is substituted with one to five moieties -L$^2$-Z and/or -L$^{2'}$-Y, preferably -L$^1$ is substituted with one moiety -L$^2$-Z or -L$^{2'}$-Y, and is optionally further substituted;

wherein -L$^2$- and -L$^{2'}$- are independently of each other a single chemical bond or a spacer moiety;

—Z is a carrier moiety; and

—Y is a functional group which may optionally be present in its protected form.

Preferably, -Q of formula (I') is selected from the group consisting of chloride, bromide, fluoride, nitrophenoxy, imidazolyl, N-hydroxysuccinimidyl, N-hydroxybenzotriazolyl, N-hydroxyazobenzotriazolyl, pentafluorphenoxy, N-hydroxysulfosuccinimidyl, diphenylphosphinomethanethiyl, 2-diphenylphosphinophenoxy, norbornene-N-hydroxysuccinimidyl, N-hydroxyphthalimide, pyridinoxy, nonafluoro tert.-butyloxy and hexafluoro isopropyloxy.

Preferably, —Y of formula (I') is selected from the group consisting of thiol, maleimide, amine, hydroxyl, carboxylic acid and derivatives, carbonate and derivatives, carbamate and derivatives, isothiocyanate, disulfide, pyridyl disulfide, methylthiosulfonyl, vinylsulfone, aldehyde, ketone, haloacetyl, selenide, azide, —NH—NH$_2$, —O—NH$_2$, a terminal alkyne, a compound of formula (z'i)

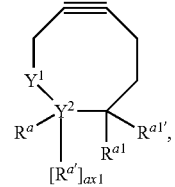

wherein

Y$^1$, Y$^2$ are independently of each other C or N,

R$^a$, R$^{a'}$, R$^{a1}$, R$^{a1'}$ are independently of each other —H or C$_{1-6}$ alkyl, ax1 is 0, if Y$^2$ is N; ax1 is 1, if Y$^2$ is C, optionally the pair R$^a$/R$^{a1}$ forms a chemical bond, if Y$^2$ is C, optionally, the pair R$^{a'}$/R$^{a1'}$ are joined together with the atom to which they are attached to form a ring A', if Y$^2$ is C, A' is cyclopropyl or phenyl;

a compound of formula (z'ii)

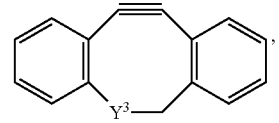

wherein

Y$^3$ is CH$_2$ or NH;

a compound of formula (z'iii)

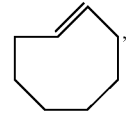

a compound of formula (z'iv),

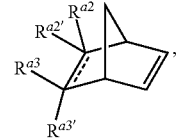

wherein

R$^{a2}$, R$^{a2'}$, R$^{a3}$, R$^{a3'}$ are —H,

----- indicates a single or double bond, optionally, the pair R$^{a2'}$/R$^{a3'}$ are joint together with the atoms to which they are attached to form a ring A$^{1'}$;

$A^{1'}$ is 5-membered heterocyclyl;

a compound of formula (z'v)

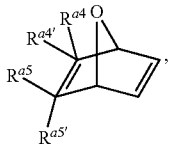 (z'v)

wherein $R^{a4}, R^{a4'}, R^{a5}, R^{a5'}$ are —H, optionally the pair $R^{a4}/R^{a5}$ forms a chemical bond, optionally, the pair $R^{a4'}/R^{a5'}$ are joint together with the atoms to which they are attached to form a ring $A^{2'}$, $A^{2'}$ is 5-membered heterocyclyl;

a compound of formula (z'vi)

 (z'vi)

wherein $R^{a6}, R^{a6'}$ are either both $C_{1-6}$ alkyl or one of $R^{a6}, R^{a6'}$ is —H and the other one is selected from $C_{1-6}$ alkyl, —COOR$^{a7}$; —CONHR$^{a7'}$, and CH$_2$OR$^{a7''}$, $R^{a7}, R^{a7'}, R^{a7''}$ are independently of each other —H or $C_{1-4}$ alkyl;

a compound of formula (z'vii)

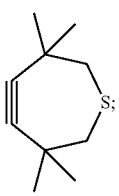 (z'vii)

a compound of formula (z'viii)

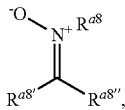 (z'viii)

wherein $R^{a8}, R^{a8'}, R^{a8''}$ are independently of each other selected from the group consisting of —H and $C_{1-4}$ alkyl;

a compound of formula (z'ix)

 (z'ix)

wherein $R^{a9}$ is —H or $C_{1-4}$ alkyl;

a compound of formula (z'x)

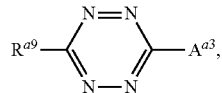 (z'x)

wherein $R^{a9}$ is selected from —COOR$^{a11}$, —CONHR$^{a11}$, and

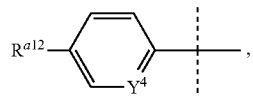

wherein $Y^4$ is C or N, $R^{a12}$ is selected from the group consisting of —H, —COOR$^{a13}$, —CONR$^{a13}$R$^{a13'}$, —CH$_2$NR$^{a13}$R$^{a13'}$, and —NR$^{a13}$COR$^{a13'}$, $R^{a13}, R^{a13'}$ are independently of each other selected from the group consisting of —H and $C_{1-4}$ alkyl, $A^{a3}$ is selected from —H, methyl, tert-butyl, —CF$_3$, —COOR,

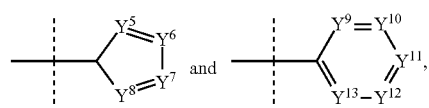

wherein each $Y^5, Y^6, Y^7, Y^8$ is independently of each other C or N, provided that no more than 3 of $Y^5, Y^6, Y^7, Y^8$ are N, each of $Y^9, Y^{10}, Y^{11}, Y^{12}, Y^{13}$ is either C, N, S or O, provided that no more than 4 of $Y^9, Y^{10}, Y^{11}, Y^{12}, Y^{13}$ are N, S, or O;

a compound of formula (z'xi)

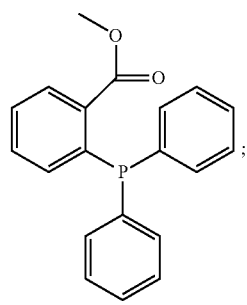 (z'xi)

a compound of formula (z'xii)

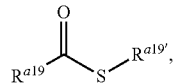 (z'xii)

wherein
$R^{a19}$, $R^{a19'}$ are independently of each other selected from the group consisting of —H, $C_{1-6}$ alkyl, $C_{2-6}$ alkenyl, $C_{2-6}$ alkynyl, $C_{3-8}$ cycloalkyl, 3- to 10-membered heterocyclyl, 8- to 11-membered heterobicyclyl, phenyl, naphthyl, indenyl, indanyl, and tetralinyl;

a compound of formula (z'xiii)

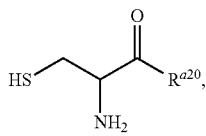

(z'xiiii)

wherein
$R^{a20}$ is selected from the group consisting of —H, $C_{1-6}$ alkyl, $C_{2-6}$ alkenyl, $C_{2-6}$ alkynyl, $C_{3-8}$ cycloalkyl, 3- to 10-membered heterocyclyl, 8- to 11-membered heterobicyclyl, phenyl, naphthyl, indenyl, indanyl, and tetralinyl;

a compound of formula (z'xiv)

$$R^{a22}\text{—Ar—}Y^{14} \quad \text{(z'xiv)},$$

wherein
Ar is selected from phenyl, naphthyl, indenyl, indanyl, and tetralinyl,
$Y^{14}$ is selected from halogen,
$R^{a22}$, $R^{a23}$, $R^{a23'}$ are independently of each other selected from the group consisting of —H, $C_{1-6}$ alkyl, $C_{2-6}$ alkenyl, $C_{2-6}$ alkynyl, $C_{3-8}$ cycloalkyl, 3- to 10-membered heterocyclyl, 8- to 11-membered heterobicyclyl, phenyl, naphthyl, indenyl, indanyl, and tetralinyl;

a compound of formula (z'xv)

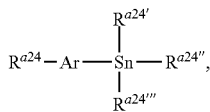

(z'xv)

Ar is selected from phenyl, naphthyl, indenyl, indanyl, and tetralinyl,
$R^{a24}$, $R^{a24'}$, $R^{a24''}$, $R^{a24'''}$ are independently of each other selected from the group consisting of —H, $C_{1-6}$ alkyl, $C_{2-6}$ alkenyl, $C_{2-6}$ alkynyl, $C_{3-8}$ cycloalkyl, 3- to 10-membered heterocyclyl, 8- to 11-membered heterobicyclyl, phenyl, naphthyl, indenyl, indanyl, and tetralinyl;

a compound of formula (z'xvi)

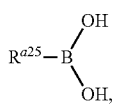

(z'xvi)

wherein
$R^{a25}$ is selected from the group consisting of —H, $C_{1-6}$ alkyl, $C_{2-6}$ alkenyl, $C_{2-6}$ alkynyl, $C_{3-8}$ cycloalkyl, 3- to 10-membered heterocyclyl, 8- to 11-membered heterobicyclyl, phenyl, naphthyl, indenyl, indanyl, and tetralinyl;

a compound of formula (z'xvii)

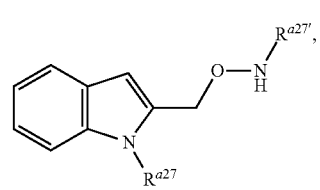

(z'xvii)

wherein
$R^{a27}$, $R^{a27'}$ are independently of each other —H or $C_{1-6}$ alkyl;

a compound of formula (z'xviii)

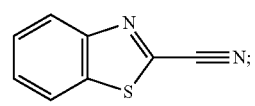

(z'xviii)

a compound of formula (z'xix)

$$R^{a12}\text{—PPh}_2 \quad \text{(z'xix)},$$

wherein
$PPh_2$ represents a group having the following formula

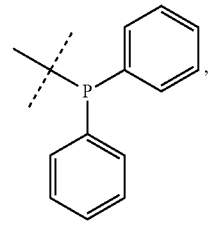

wherein the dashed line indicates attachment to the rest of the moiety of formula (z'xix),
$R^{a12}$ is selected from

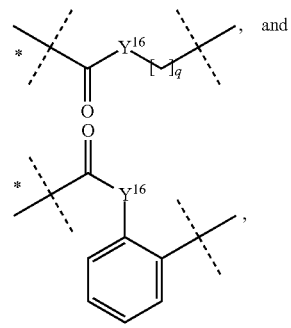

and wherein
the unmarked dashed line indicates attachment to the rest of the moiety of formula (z'xix),
the dashed line with the asterisk indicates attachment to -$L^{2'}$-,
q is 1 or 2, and
$Y^{16}$ is O or S;

and a compound of formula (z'xx)

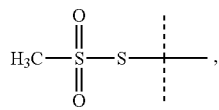
(z'xx)

wherein the dashed line indicates attachment to -L²-;

wherein the moieties of formula (z'i), (z'ii), (z'iii), (z'iv), (z'v), (z'vi), (z'vii), (z'viii), (z'ix), (z'x), (z'xi), (z'xii), (z'xiii), (z'xiv), (z'xv), (z'xvi), (z'xvii) and (z'xviii) are substituted with a moiety -L²- and are optionally further substituted.

Preferably, $Y^1$ of formula (z'i) is C.

Preferably, $R^a$, $R^{a'}$, $R^{a1}$, $R^{a1'}$ of formula (z'i) are —H.

Preferred embodiments of formula (z'i) are selected from the group consisting of

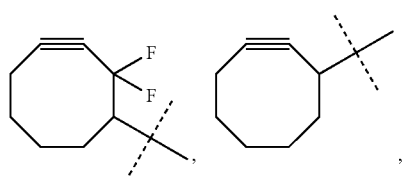

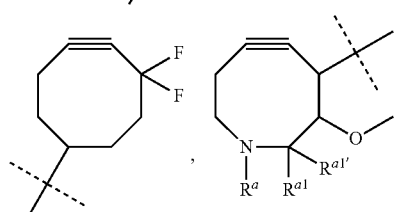

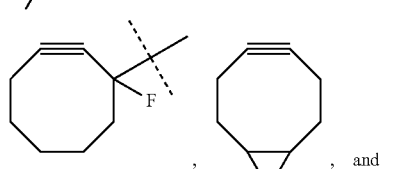

, and

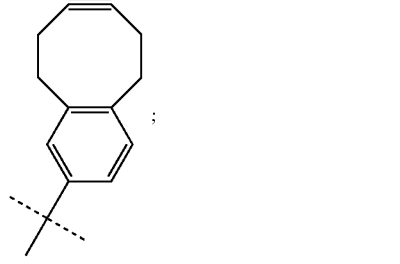
;

wherein the dashed line indicates attachment to -L²-, and $R^a$, $R^{a1}$, $R^{a1'}$ are used as defined in formula (z'i).

Preferred embodiments of formula (z'ii) are

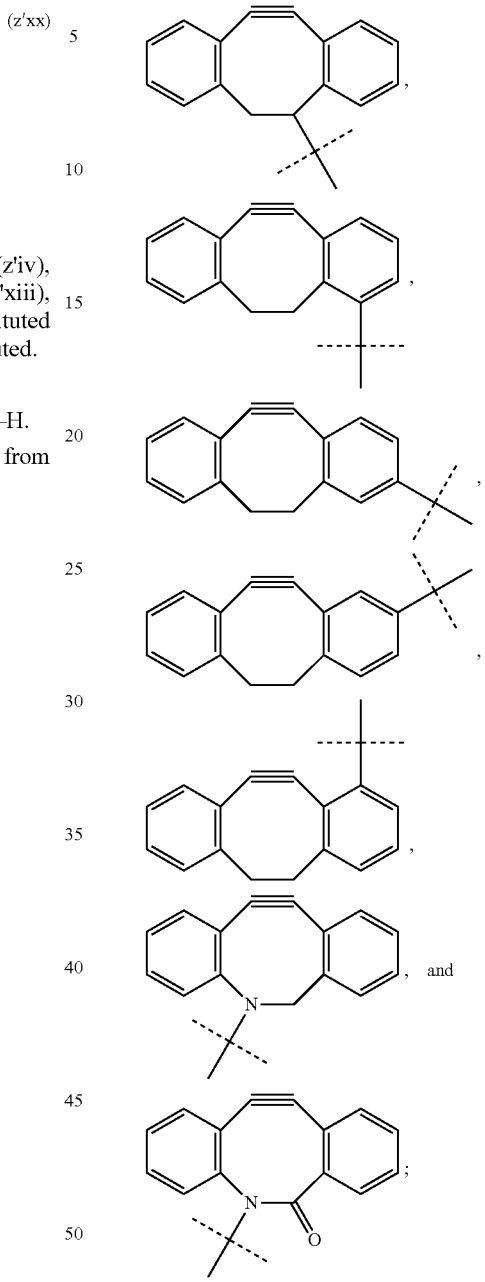

wherein the dashed line indicates attachment to -L²-.

Preferred embodiments of formula (z'iii) are

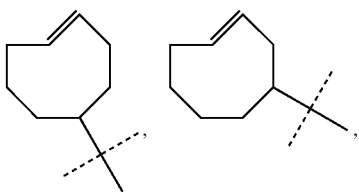

-continued

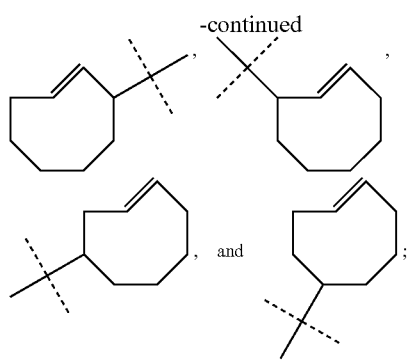

wherein
the dashed line indicates attachment to -L²-.
Preferred embodiments of formula (z'iv) are

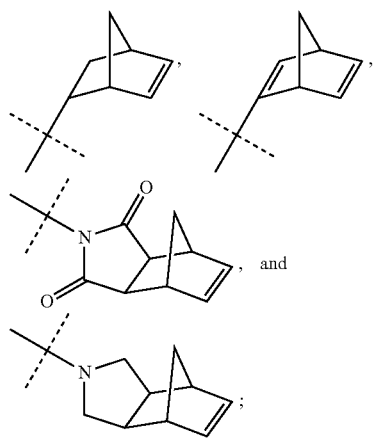

wherein
the dashed line indicates attachment to -L²-.
A preferred embodiment of formula (z'v) is

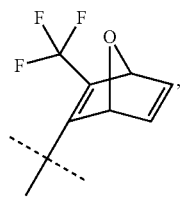

wherein
the dashed line indicates attachment to -L²-.
Preferred embodiments of formula (z'vi) are

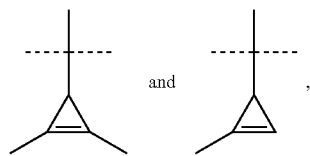

wherein
the dashed line indicates attachment to -L²-.

A preferred embodiments of formula (z'vii) is

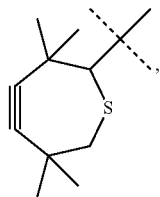

wherein
the dashed line indicates attachment to -L²-.
Preferred embodiments of formula (z'viii) are

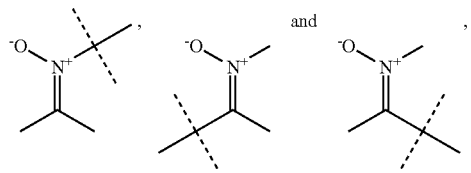

wherein
the dashed line indicates attachment to -L²-.
A preferred embodiment of formula (z'ix) is

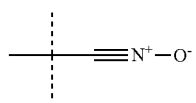

wherein
the dashed line indicates attachment to -L²-.
Preferred embodiments of $A^{a3}$ of formula (z'x) are

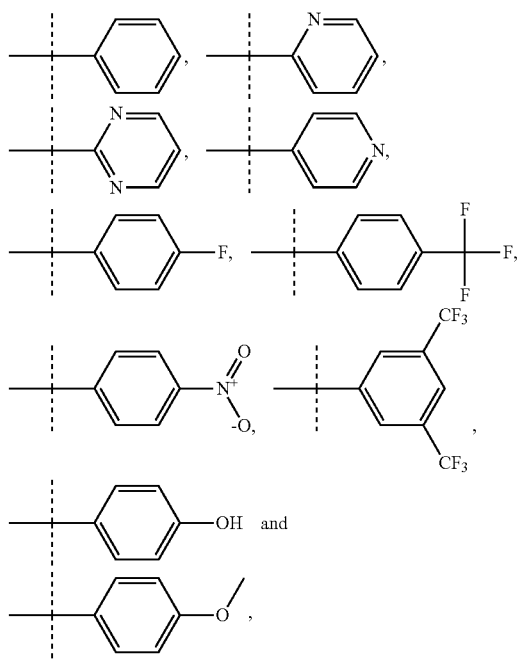

wherein
the dashed line indicates attachment to the remainder of (z'x).

Preferred embodiments of the moiety

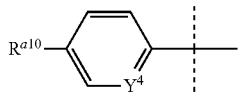

of formula (z'x) are

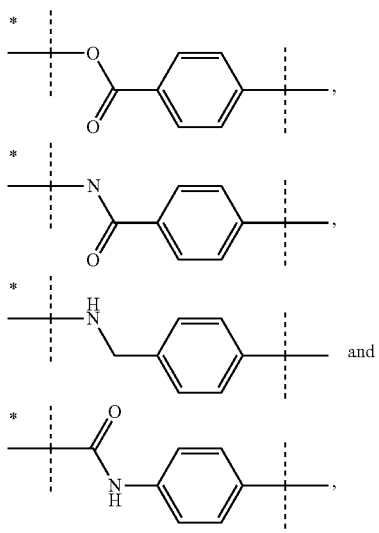

wherein
the unmarked dashed line indicates attachment to the remainder of (z'x) and
the dashed line marked with the asterisk indicates attachment to -L$^{2'}$-.

A preferred embodiment of formula (z'xii) is

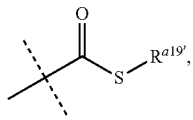

wherein
the dashed line indicates attachment to -L$^{2'}$-, and
R$^{a19}$ is H, methyl, ethyl, propyl or butyl.

A preferred embodiment of formula (z'xiii) is

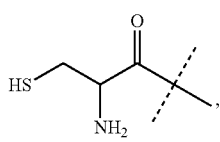

wherein
the dashed line indicates attachment to -L$^{2'}$-.

A preferred embodiment of formula (z'xiv) is

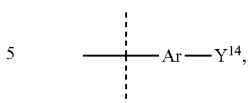

wherein
the dashed line indicates attachment to -L$^{2'}$-,
Ar is selected from phenyl, naphthyl, indenyl, indanyl, and tetralinyl, and
Y$^{14}$ is halogen.

A preferred embodiment of formula (z'xv) is

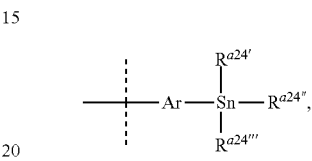

wherein
the dashed line indicates attachment to -L$^{2'}$-,
Ar is selected from the group consisting of phenyl, naphthyl, indenyl, indanyl, and tetralinyl; and
R$^{a24'}$, R$^{a24''}$, R$^{a24'''}$ are independently of each other selected from the group consisting of H, methyl, ethyl, propyl and butyl.

A preferred embodiment of formula (z'xvi) is

wherein
the dashed line indicates attachment to -L$^{2'}$-.

A preferred embodiment of formula (z'xvii) is

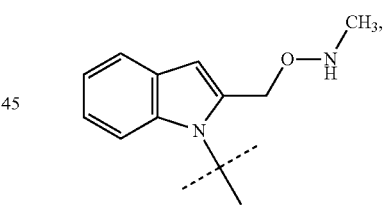

wherein
the dashed line indicates attachment to -L$^{2'}$-.

In one embodiment a1 of formula (I) and (I') is 0. In another embodiment a1 of formula (I) and (I') is 1. Preferably, a1 of formula (I) and (I') is 0.

In one embodiment a2 of formula (I) and (I') is 0. In another embodiment a2 of formula (I) and (I') is 1. Preferably, a2 of formula (I) and (I') is 0.

In one embodiment a1 and a2 of formula (I) and (I') are both 0. In another embodiment a1 and a2 of formula (I) and (I') are both 1. In an even further embodiment a1 of formula (I) and (I') is 0 and a2 of formula (I) and (I') is 1. In an even further embodiment a1 of formula (I) and (I') is 1 and a2 of formula (I) and (I') is 0. Preferably, a1 and a2 of formula (I) and (I') are both 0.

In a preferred embodiment R$^1$, R$^{1a}$, R$^7$ and R$^{7a}$ of formula (I) and (I') are independently of each other selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methybutyl, 1-methylbutyl, 1-ethylpropyl,

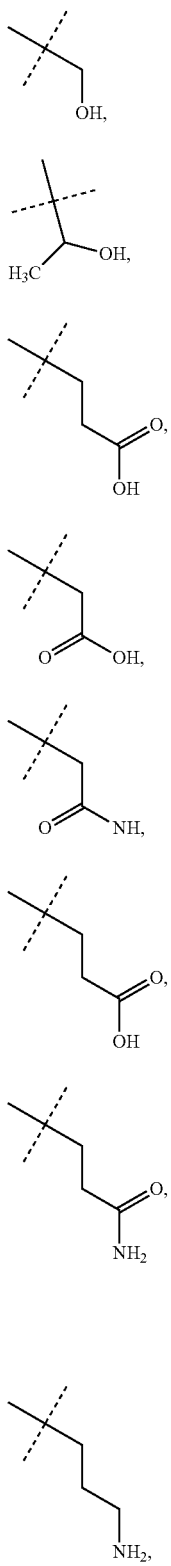
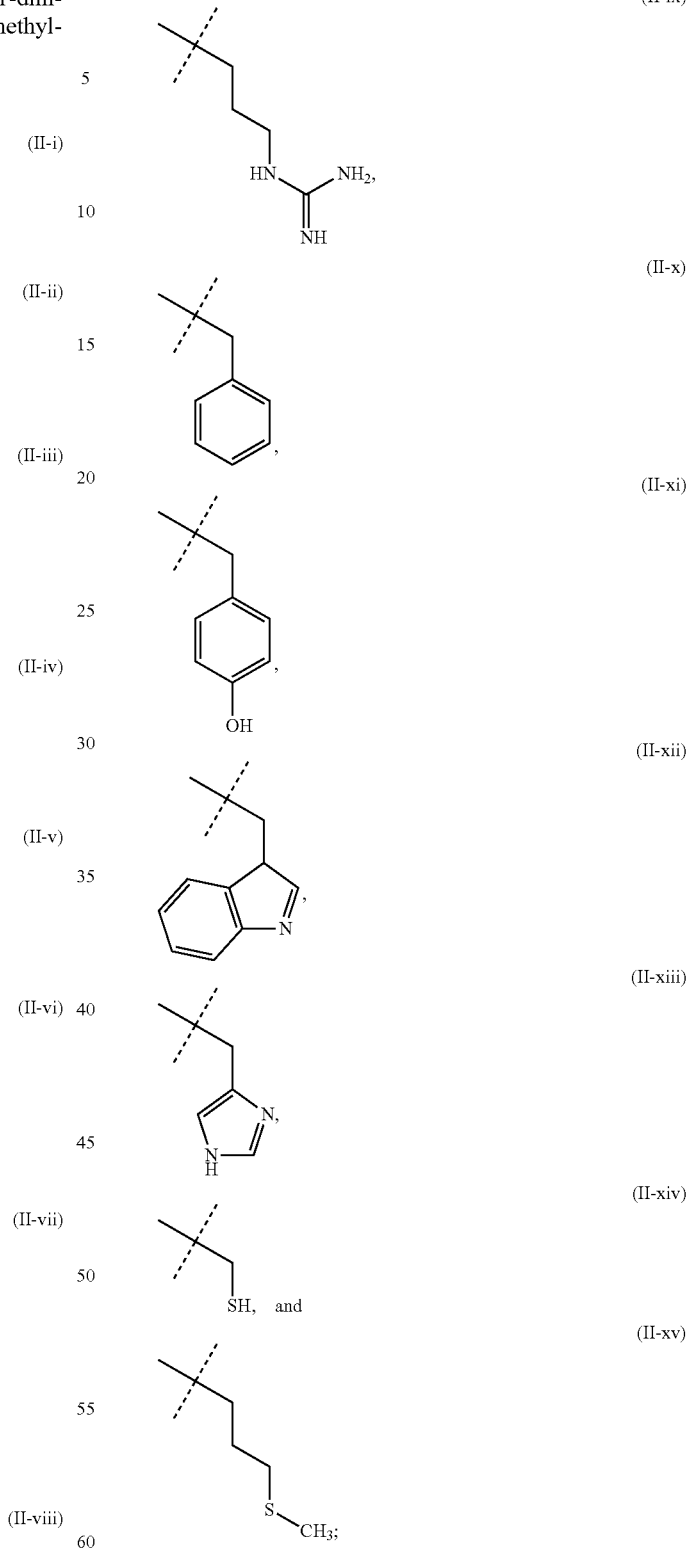

wherein
dashed lines indicate attachment to the remainder of -L$^1$.

More preferably, R$^1$, R$^{1a}$, R$^7$ and R$^{7a}$ of formula (I) and (I') are independently of each other selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methylbutyl, 1-methylbutyl and 1-ethylpropyl.

Even more preferably, $R^1$, $R^{1a}$, $R^7$ and $R^{7a}$ of formula (I) and (I') are independently of each other selected from the group consisting of —H, methyl, ethyl, n-propyl, and iso-propyl. Even more preferably, $R^1$, $R^{1a}$, $R^7$ and $R^{7a}$ of formula (I) and (I') are independently of each other —H or methyl. Most preferably, $R^1$, $R^{1a}$, $R^7$ and $R^{7a}$ of formula (I) and (I') are —H.

Preferably, a1 of formula (I) and (I') is 0 and $R^1$ and $R^{1a}$ of formula (I) and (I') are independently of each other selected from —H and methyl. Preferably, one of $R^1$ and $R^{1a}$ of formula (I) and (I') is —H.

Preferably, $R^2$, $R^{2a}$, $R^6$ and $R^{6a}$ of formula (I) and (I') are independently of each other selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methylbutyl, 1-methylbutyl, and 1-ethylpropyl.

More preferably, $R^2$, $R^{2a}$, $R^6$ and $R^{6a}$ of formula (I) and (I') are independently of each other selected from the group consisting of —H, methyl, ethyl, n-propyl, and iso-propyl. Even more preferably, $R^2$, $R^{2a}$, $R^6$ and $R^{6a}$ of formula (I) and (I') are independently of each other —H or methyl. Most preferably, $R^2$, $R^{2a}$, $R^6$ and $R^{6a}$ of formula (I) and (I') are —H.

In a preferred embodiment a2 is 0 and $R^2$ and $R^{2a}$ of formula (I) and (I') are both —H.

Preferably, $R^3$ and $R^{3a}$ of formula (I) and (I') are independently of each other selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methylbutyl, 1-methylbutyl, and 1-ethylpropyl.

More preferably, $R^3$ and $R^{3a}$ of formula (I) and (I') are selected from —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methylbutyl, 1-methylbutyl and 1-ethylpropyl. Even more preferably, $R^3$ and $R^{3a}$ of formula (I) and (I') are selected from —H, methyl and ethyl.

In a preferred embodiment $R^3$ and $R^{3a}$ of formula (I) and (I') are both methyl.

In an even more preferred embodiment $R^3$ and $R^{3a}$ of formula (I) and (I') are both —H.

Preferably, $R^4$ of formula (I) and (I') is selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methylbutyl, 1-methylbutyl, and 1-ethylpropyl. More preferably, $R^4$ of formula (I) and (I') is —H or methyl.

Preferably, $R^5$ of formula (I) and (I') is selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methylbutyl, 1-methylbutyl, and 1-ethylpropyl. More preferably, $R^5$ of formula (I) and (I') is selected from —H and methyl.

Preferably, $R^{5a}$ of formula (I) and (I') is selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methylbutyl, 1-methylbutyl and 1-ethylpropyl. Even more preferably, $R^{5a}$ of formula (I) and (I') is selected from —H, methyl and ethyl. Most preferably, $R^{5a}$ is —H.

In a preferred embodiment -D is a primary or secondary amine-containing biologically active moiety and $R^{5a}$ is —H.

Preferably, each $R^6$, $R^{6a}$, $R^7$, $R^{7a}$, $R^8$, $R^{8a}$, $R^{8b}$, $R^9$, $R^{9a}$, $R^{9b}$ of formula (I) and (I') is independently of each other selected from the group consisting of —H, halogen, —CN, —COOR$^{10}$, —OR$^{10}$, —C(O)R$^{10}$, —C(O)N(R$^{10}$R$^{10a}$), —S(O)$_2$N(R$^{10}$R$^{10a}$), —S(O)N(R$^{10}$R$^{10a}$), —S(O)$_2$R$^{10}$, —S(O)R$^{10}$, —N(R$^{10}$)S(O)$_2$N(R$^{10a}$R$^{10b}$), —SR$^{10}$, —N(R$^{10}$R$^{10a}$), —NO$_2$, —OC(O)R$^{10}$, —N(R$^{10}$)C(O)R$^{10a}$, —N(R$^{10}$)S(O)$_2$R$^{10a}$, —N(R$^{10}$)S(O)R$^{10a}$, —N(R$^{10}$)C(O)OR$^{10a}$, —N(R$^{10}$)C(O)N(R$^{10a}$R$^{10b}$), —OC(O)N(R$^{10}$R$^{10a}$), -T, $C_{1-10}$ alkyl, $C_{2-10}$ alkenyl, and $C_{2-10}$ alkynyl; wherein -T, $C_{1-10}$ alkyl, $C_{2-10}$ alkenyl, and $C_{2-10}$ alkynyl are optionally substituted with one or more R$^{11}$, which are the same or different and wherein $C_{1-10}$ alkyl, $C_{2-10}$ alkenyl, and $C_{2-10}$ alkynyl are optionally interrupted by one or more groups selected from the group consisting of -T-, —C(O)O—, —O—, —C(O)—, —C(O)N(R$^{12}$)—, —S(O)$_2$N(R$^{12}$)—, —S(O)N(R$^{12}$)—, —S(O)$_2$—, —S(O)—, —N(R$^{12}$)S(O)$_2$N(R$^{12a}$)—, —S—, —N(R$^{12}$)—, —OC(OR$^{12}$)(R$^{12a}$)—, —N(R$^{12}$)C(O)N(R$^{12a}$)—, and —OC(O)N(R$^{12}$)—;

each R$^{10}$, R$^{10a}$, R$^{10b}$ is independently selected from the group consisting of —H, -T, $C_{1-6}$ alkyl, $C_{2-6}$ alkenyl, and $C_{2-6}$ alkynyl; wherein -T, $C_{1-6}$ alkyl, $C_{2-6}$ alkenyl, and $C_{2-6}$ alkynyl are optionally substituted with one or more R$^{11}$, which are the same or different and wherein $C_{1-6}$ alkyl, $C_{2-6}$ alkenyl, and $C_{2-6}$ alkynyl are optionally interrupted by one or more groups selected from the group consisting of -T-, —C(O)O—, —O—, —C(O)—, —C(O)N(R$^{12}$)—, —S(O)$_2$N(R$^{12}$)—, —S(O)N(R$^{12}$)—, —S(O)$_2$—, —S(O)—, —N(R$^{12}$)S(O)$_2$N(R$^{12a}$)—, —S—, —N(R$^{12}$)—, —OC(OR$^{12}$)(R$^{12a}$)—, —N(R$^{12}$)C(O)N(R$^{12a}$)—, and —OC(O)N(R$^{12}$)—;

each T is independently of each other selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T is independently optionally substituted with one or more R$^{11}$, which are the same or different;

each R$^{11}$ is independently of each other selected from the group consisting of halogen, —CN, oxo (=O), —COOR$^{13}$, —OR$^{13}$, —C(O)R$^{13}$, —C(O)N(R$^{13}$R$^{13a}$), —S(O)$_2$N(R$^{13}$R$^{13a}$), —S(O)N(R$^{13}$R$^{13a}$), —S(O)$_2$R$^{13}$, —S(O)R$^{13}$, —N(R$^{13}$)S(O)$_2$N(R$^{13a}$R$^{13b}$), —SR$^{13}$, —N(R$^{13}$R$^{13a}$), —NO$_2$, —OC(O)R$^{13}$, —N(R$^{13}$)C(O)R$^{13a}$, —N(R$^{13}$)S(O)$_2$R$^{13a}$, —N(R$^{13}$)S(O)R$^{13a}$, —N(R$^{13}$)C(O)OR$^{13a}$, —N(R$^{13}$)C(O)N(R$^{13a}$R$^{13b}$), —OC(O)N(R$^{13}$R$^{13a}$), and $C_{1-6}$ alkyl, wherein $C_{1-6}$ alkyl is optionally substituted with one or more halogen, which are the same or different;

each R$^{12}$, R$^{12a}$, R$^{13}$, R$^{13a}$, R$^{13b}$ is independently selected from the group consisting of —H, and $C_{1-6}$ alkyl; wherein $C_{1-6}$ alkyl is optionally substituted with one or more halogen, which are the same or different.

Even more preferably, each R$^6$, R$^{6a}$, R$^7$, R$^{7a}$, R$^8$, R$^{8a}$, R$^{8b}$, R$^9$, R$^{9a}$, R$^{9b}$ of formula (I) and (I') is independently of each other selected from the group consisting of —H, halogen, —CN, —COOR$^{10}$, —OR$^{10}$, —C(O)R$^{10}$, —C(O)N(R$^{10}$R$^{10a}$), —S(O)$_2$N(R$^{10}$R$^{10a}$), —S(O)N(R$^{10}$R$^{10a}$), —S(O)$_2$R$^{10}$, —S(O)R$^{10}$, —N(R$^{10}$)S(O)$_2$N(R$^{10a}$R$^{10b}$), —SR$^{10}$, —N(R$^{10}$R$^{10a}$), —NO$_2$, —OC(O)R$^{10}$, —N(R$^{10}$)C(O)R$^{10a}$, —N(R$^{10}$)S(O)$_2$R$^{10a}$, —N(R$^{10}$)S(O)R$^{10a}$, —N(R$^{10}$)C(O)OR$^{10a}$, —N(R$^{10}$)C(O)N(R$^{10a}$R$^{10b}$), —OC(O)N(R$^{10}$R$^{10a}$), -T, $C_{1-6}$ alkyl, $C_{2-6}$ alkenyl, and $C_{2-6}$ alkynyl; wherein -T, $C_{1-6}$ alkyl, $C_{2-6}$ alkenyl, and $C_{2-6}$ alkynyl are optionally substituted with one or more R$^{11}$, which are the same or different and wherein $C_{1-6}$ alkyl, $C_{2-6}$ alkenyl, and $C_{2-6}$ alkynyl are optionally interrupted by one or more groups selected from the group consisting of -T-, —C(O)O—, —O—, —C(O)—, —C(O)N(R$^{12}$)—, —S(O)$_2$N $(R^{12})$—, —S(O)N($R^{12}$)—, —S(O)$_2$—, —S(O)—, —N($R^{12}$)S(O)$_2$N($R^{12a}$)—, —S—, —N($R^{12}$)—, —OC(O$R^{12}$)($R^{12a}$)—, —N($R^{12}$)C(O)N($R^{12a}$)—, and —OC(O)N($R^{12}$)—;

each $R^{10}$, $R^{10a}$, $R^{10b}$ is independently selected from the group consisting of —H, -T, $C_{1-6}$ alkyl, $C_{2-6}$ alkenyl, and $C_{2-6}$ alkynyl;

each T is independently of each other selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl;

each $R^{11}$ is independently of each other $C_{1-6}$ alkyl;

each $R^{12}$, $R^{12a}$ is independently of each other selected from the group consisting of —H, and $C_{1-4}$ alkyl, wherein $C_{1-6}$ alkyl is optionally substituted with one or more halogen, which are the same or different.

Optionally, one or more of the pairs $R^1/R^2$, $R^1/R^3$, $R^1/R^4$, $R^1/R^5$, $R^1/R^6$, $R^1/R^7$, $R^2/R^3$, $R^2/R^4$, $R^2/R^5$, $R^2/R^6$, $R^2/R^7$, $R^3/R^4$, $R^3/R^5$, $R^3/R^6$, $R^3/R^7$, $R^4/R^5$, $R^4/R^6$, $R^4/R^7$, $R^5/R^6$, $R^5/R^7$, $R^6/R^7$ of formula (I) and (I') are joint together with the atoms to which they are attached to form a ring A. More preferably, one or more of the pairs $R^1/R^2$, $R^1/R^4$, $R^1/R^6$, $R^1/R^7$, $R^2/R^3$, $R^2/R^4$, $R^2/R^6$, $R^2/R^7$, $R^3/R^5$, $R^3/R^6$, $R^4/R^7$, $R^5/R^6$, $R^6/R^7$ are optionally joint together with the atoms to which they are attached to form a ring A. Even more preferably, one or more of the pairs $R^1/R^4$, $R^1/R^7$, $R^2/R^4$, $R^2/R^6$, $R^3/R^5$, $R^3/R^6$, are optionally joint together with the atoms to which they are attached to form a ring A.

Preferably, A of formula (I) and (I') is selected from phenyl, $C_{3-10}$ cycloalkyl and 3- to 10-membered heterocyclyl.

In a preferred embodiment the prodrug of the present invention is of formula (Ia) or (Ib)

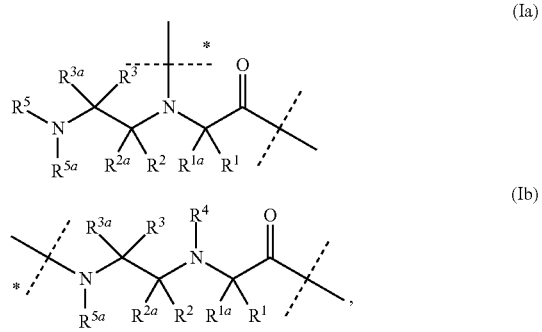

(Ia)

(Ib)

wherein the unmarked dashed line indicates attachment to -D, the dashed line marked with the asterisk indicates attachment to -L$^2$-Z, and -D, $R^1$, $R^{1a}$, $R^2$, $R^{2a}$, $R^3$, $R^{3a}$, $R^4$, $R^5$, $R^{5a}$, -L$^2$- and —Z are used as defined for formula (I).

It is understood that in formula (Ia) $R^4$ is selected as being —H which is replaced by -L$^2$-Z and that in formula (Ib) $R^5$ is selected as being —H which is replaced by -L$^2$-Z.

In one preferred embodiment the prodrug of the present invention is of formula (Ia). In an equally preferred embodiment the prodrug of the present invention is of formula (Ib).

Preferred embodiment for $R^1$, $R^{1a}$, $R^2$, $R^{2a}$, $R^3$, $R^{3a}$, $R^4$, $R^5$ and $R^{5a}$ of formula (Ia) and (Ib) are as described for formula (I).

In preferred embodiment the prodrug reagent of the present invention is of formula (I'a) or (I'b)

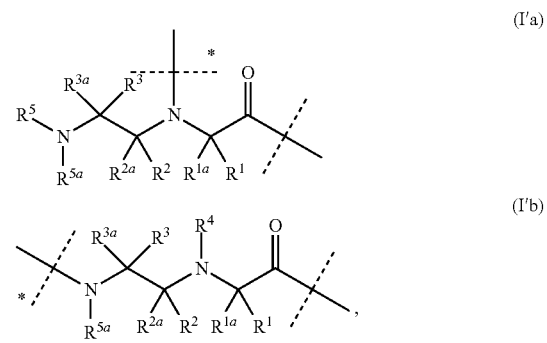

(I'a)

(I'b)

wherein the unmarked dashed line indicates attachment to -Q, the dashed line marked with the asterisk indicates attachment to -L$^2$-Z or -L$^{2'}$-Y, and -Q, $R^1$, $R^{1a}$, $R^2$, $R^{2a}$, $R^3$, $R^{3a}$, $R^4$, $R^5$, $R^{5a}$, -L$^2$-, -L$^{2'}$-, Z and Y are used as defined for formula (I').

It is understood that in formula (I'a) $R^4$ is selected as being —H which is replaced by -L$^2$-Z or -L$^{2'}$-Y and that in formula (I'b) $R^5$ is selected as being —H which is replaced by -L$^2$-Z or -L$^{2'}$-Y.

In one preferred embodiment the prodrug reagent of the present invention is of formula (I'a).

In an equally preferred embodiment the prodrug reagent of the present invention is of formula (I'b).

Preferred embodiment for $R^1$, $R^{1a}$, $R^2$, $R^{2a}$, $R^3$, $R^{3a}$, $R^4$, $R^5$ and $R^{5a}$ of formula (I'a) and (I'b) are as described for formula (I').

In a preferred embodiment -L$^1$- of the prodrug of the present invention is of formula (IIa)

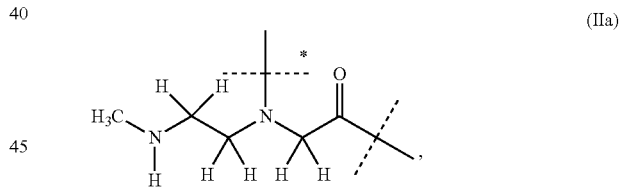

(IIa)

wherein the unmarked dashed line indicates attachment to -D; and the dashed line marked with the asterisk indicates attachment to -L$^2$-Z.

It is understood that in formula (IIa) $R^4$ is selected as being —H which is replaced by -L$^2$-Z.

In a preferred embodiment -L$^1$- of the prodrug reagent of the present invention is of formula (IIa')

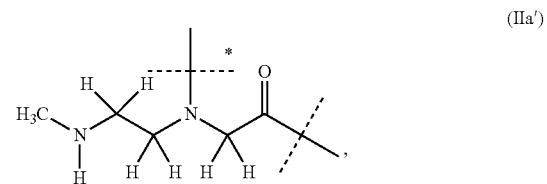

(IIa')

wherein the unmarked dashed line indicates attachment -Q; and
the dashed line marked with the asterisk indicates attachment to -L²-Z or -L²'-Y.

It is understood that in formula (IIa') R⁴ is selected as being —H which is replaced by -L²-Z or -L²'-Y.

Z is a carrier. Preferably, Z comprises a $C_{8-18}$ alkyl group or a polymer with a molecular weight of at least 0.5 kDa.

In one embodiment Z comprises a $C_{8-18}$ alkyl group.

In another embodiment Z comprises a polymer with a molecular weight of at least 0.5 kDa, preferably of at least 1 kDa, more preferably of at least 2 kDa, even more preferably at least 4 kDa, even more preferably 5 kDa, even more preferably of at least 7.5 kDa, even more preferably of at least 10 kDa. If the polymer is a soluble polymer, it is preferred that it has at most a molecular weight of 2000 kDa, more preferably of at most 1000 kDa, even more preferably of at most 750 kDa, even more preferably of at most 500 kDa, even more preferably of at most 250 kDa and most preferably of at most 150 kDa.

Preferably, a polymeric carrier Z comprises at least one of the polymers selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In a preferred embodiment Z comprises a protein. Even more preferably, Z comprises a protein selected from the group consisting of albumin, transferrin, and immunoglobulin.

In another preferred embodiment Z comprises a protein carrier as disclosed in WO2013/024049A1, which is hereby incorporated by reference.

In another preferred embodiment Z comprises a PEG-based polymer comprising at last 10% PEG, such as at least 20% PEG, at least 30% PEG, at least 40% PEG or at least 50% PEG; or a hyaluronic acid-based polymer comprising at least 10% hyaluronic acid, such as at least 20% hyaluronic acid, at least 30% hyaluronic acid, at least 40% hyaluronic acid or at least 50% hyaluronic acid.

In one embodiment Z comprises a water-soluble polymer with a molecular weight of at least 0.5 kDa, preferably of at least 1 kDa, more preferably of at least 2 kDa, even more preferably at least 4 kDa, even more preferably 5 kDa, even more preferably of at least 7.5 kDa, even more preferably of at least 10 kDa. Preferably, such water-soluble polymer has at most a molecular weight of 2000 kDa, more preferably of at most 1000 kDa, even more preferably of at most 750 kDa, even more preferably of at most 500 kDa, even more preferably of at most 250 kDa and most preferably of at most 150 kDa.

Preferably, Z comprises a linear, branched or dendritic PEG-based polymer comprising at least 10% PEG (such as at least 20% PEG, at least 30% PEG, at least 40% PEG or at least 50% PEG) with a molecular weight from 2,000 Da to 150,000 Da. Even more preferably Z comprises a PEG-based carrier as disclosed in WO2103/024047 A1 and WO2013/024047 A1, which are hereby incorporated by reference.

In another embodiment Z comprises a water-insoluble polymer.

Preferably, Z comprises a water-insoluble hydrogel, more preferably a PEG-based hydrogel comprising at least 10% PEG (such as at least 20% PEG, at least 30% PEG, at least 40% PEG or at least 50% PEG) or a hyaluronic acid-based hydrogel comprising at least 10% hyaluronic acid (such as at least 20% hyaluronic acid, at least 30% hyaluronic acid, at least 40% hyaluronic acid or at least 50% hyaluronic acid) and most preferably Z comprises a hydrogel as disclosed in WO2006/003014 A2, WO2011/012715 A1 or WO2014/056926 A1, which are hereby incorporated by reference.

In an even more preferred embodiment Z comprises a hydrogel obtained from a process for the preparation of a hydrogel comprising the steps of:

(a) providing a mixture comprising (a-i) at least one backbone reagent, wherein the at least one backbone reagent has a molecular weight ranging from 1 to 100 kDa, and comprises at least three functional groups $A^{x0}$, wherein each $A^{x0}$ is a maleimide, amine (—NH₂ or —NH—), hydroxyl (—OH), thiol (—SH), carboxyl (—COOH) or activated carboxyl (—COY¹, wherein Y¹ is selected from formulas (f-i) to (f-vii):

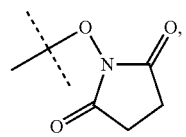
(f-i)

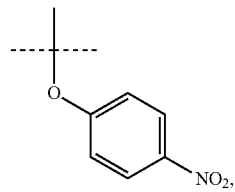
(f-ii)

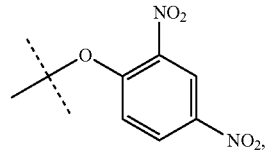
(f-iii)

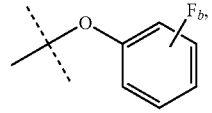
(f-iv)

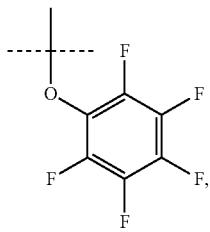
(f-v)

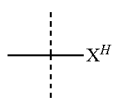
(f-vi)

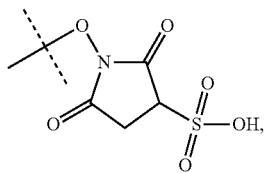
(f-vii)

wherein the dashed lines indicate attachment to the rest of the molecule, b is 1, 2, 3 or 4, $X^H$ is Cl, Br, I, or F);

(a-ii) at least one crosslinker reagent, wherein the at least one crosslinker reagent has a molecular weight ranging from 0.2 to 40 kDa and comprises at least two functional end groups selected from the group consisting of activated ester groups, activated carbamate groups, activated carbonate groups, activated thiocarbonate groups, amine groups and thiol groups;

in a weight ratio of the at least one backbone reagent to the at least one crosslinker reagent ranging from 1:99 to 99:1 and wherein the molar ratio of $A^{x0}$ to functional end groups is >1;

(b) polymerizing the mixture of step (a) in a suspension polymerization to a hydrogel.

Preferably, the crosslinker reagent of step (a-ii) comprises at least one reversible linkage. Even more preferably, such at least one reversible linkage is an ester and/or carbonate.

The mixture of step (a) comprises a first solvent and at least a second solvent. Said first solvent is preferably selected from the group comprising dichloromethane, chloroform, tetrahydrofuran, ethyl acetate, dimethylformamide, acetonitrile, dimethyl sulfoxide, propylene carbonate, N-methylpyrrolidone, methanol, ethanol, isopropanol and water and mixtures thereof.

The at least one backbone reagent and at least one crosslinker reagent are dissolved in the first solvent, i.e. the disperse phase of the suspension polymerization. In one embodiment the backbone reagent and the crosslinker reagent are dissolved separately, i.e. in different containers, using either the same or different solvent and preferably using the same solvent for both reagents. In another embodiment, the backbone reagent and the crosslinker reagent are dissolved together, i.e. in the same container and using the same solvent.

A suitable solvent for the backbone reagent is an organic solvent. Preferably, the solvent is selected from the group consisting of dichloromethane, chloroform, tetrahydrofuran, ethyl acetate, dimethylformamide, acetonitrile, dimethyl sulfoxide, propylene carbonate, N-methylpyrrolidone, methanol, ethanol, isopropanol and water and mixtures thereof. More preferably, the backbone reagent is dissolved in a solvent selected from the group comprising acetonitrile, dimethyl sulfoxide, methanol or mixtures thereof. Most preferably, the backbone reagent is dissolved in dimethylsulfoxide.

In one embodiment the backbone reagent is dissolved in the solvent in a concentration ranging from 1 to 300 mg/ml, more preferably from 5 to 60 mg/ml and most preferably from 10 to 40 mg/ml.

A suitable solvent for the crosslinker reagent is an organic solvent. Preferably, the solvent is selected from the group comprising dichloromethane, chloroform, tetrahydrofuran, ethyl acetate, dimethylformamide, acetonitrile, dimethyl sulfoxide, propylene carbonate, N-methylpyrrolidone, methanol, ethanol, isopropanol, water or mixtures thereof. More preferably, the crosslinker reagent is dissolved in a solvent selected from the group comprising dimethylformamide, acetonitrile, dimethyl sulfoxide, methanol or mixtures thereof. Most preferably, the crosslinker reagent is dissolved in dimethylsulfoxide.

In one embodiment the crosslinker reagent is dissolved in the solvent in a concentration ranging from 5 to 500 mg/ml, more preferably from 25 to 300 mg/ml and most preferably from 50 to 200 mg/ml.

The at least one backbone reagent and the at least one crosslinker reagent are mixed in a weight ratio ranging from 1:99 to 99:1, e.g. in a ratio ranging from 2:98 to 90:10, in a weight ratio ranging from 3:97 to 88:12, in a weight ratio ranging from 3:96 to 85:15, in a weight ratio ranging from 2:98 to 90:10 and in a weight ratio ranging from 5:95 to 80:20; particularly preferred in a weight ratio from 5:95 to 80:20, wherein the first number refers to the backbone reagent and the second number to the crosslinker reagent.

Preferably, the ratios are selected such that the mixture of step (a) comprises a molar excess of functional groups $A^{x0}$ from the backbone reagent compared to the activated functional end groups of the crosslinker reagent. Consequently, the hydrogel resulting from the process has free functional groups $A^{x0}$ which can be used to couple other moieties to the hydrogel, such as spacers, and/or reversible prodrug linker moieties $L^1$.

The at least one second solvent, i.e. the continuous phase of the suspension polymerization, is preferably an organic solvent, more preferably an organic solvent selected from the group comprising linear, branched or cyclic $C_{5-30}$ alkanes; linear, branched or cyclic $C_{5-30}$ alkenes; linear, branched or cyclic $C_{5-30}$ alkynes; linear or cyclic poly (dimethylsiloxanes); aromatic $C_{6-20}$ hydrocarbons; and mixtures thereof. Even more preferably, the at least second solvent is selected from the group comprising linear, branched or cyclic $C_{5-16}$ alkanes; toluene; xylene; mesitylene; hexamethyldisiloxane; or mixtures thereof. Most preferably, the at least second solvent selected from the group comprising linear $C_{7-11}$ alkanes, such as heptane, octane, nonane, decane and undecane.

Preferably, the mixture of step (a) further comprises a detergent. Preferred detergents are Cithrol DPHS, Hypermer 70A, Hypermer B246, Hypermer 1599A, Hypermer 2296, and Hypermer 1083.

Preferably, the detergent has a concentration of 0.1 g to 100 g per 1 L total mixture, i.e. disperse phase and continuous phase together. More preferably, the detergent has a concentration of 0.5 g to 10 g per 1 L total mixture, and most preferably, the detergent has a concentration of 0.5 g to 5 g per 1 L total mixture.

Preferably, the mixture of step (a) is an emulsion.

The polymerization in step (b) is initiated by adding a base. Preferably, the base is a non-nucleophilic base soluble in alkanes, more preferably the base is selected from N,N,N',N'-tetramethylethylene diamine (TMEDA), 1,4-dimethylpiperazine, 4-methylmorpholine, 4-ethylmorpholine, 1,4-diazabicyclo[2.2.2]octane, 1,1,4,7,10,10-hexamethyltriethylenetetramine, 1,4,7-trimethyl-1,4,7-triazacyclononane, tris[2-(dimethylamino)ethyl]amine, triethylamine, DIPEA, trimethylamine, N,N-dimethylethylamine, N,N,N',N'-tetramethyl-1,6-hexanediamine, N,N,N',N'',N''-pentamethyldiethylenetriamine, 1,8-diazabicyclo[5.4.0]undec-7-ene, 1,5-diazabicyclo[4.3.0]non-5-ene, and hexamethylenetetramine. Even more preferably, the base is selected from TMEDA, 1,4-dimethylpiperazine, 4-methylmorpholine, 4-ethylmorpholine, 1,4-diazabicyclo[2.2.2]octane, 1,1,4,7,10,10-hexamethyltriethylenetetramine, 1,4,7-trimethyl-1,4,7-triazacyclononane, tris[2-(dimethylamino)ethyl]amine, 1,8-diazabicyclo[5.4.0]undec-7-ene, 1,5-diazabicyclo[4.3.0]non-5-ene, and hexamethylenetetramine. Most preferably, the base is TMEDA.

The base is added to the mixture of step (a) in an amount of 1 to 500 equivalents per activated functional end group in the mixture, preferably in an amount of 5 to 50 equivalents, more preferably in an amount of 5 to 25 equivalents and most preferably in an amount of 10 equivalents.

In process step (b), the polymerization of the hydrogel is a condensation reaction, which preferably occurs under continuous stirring of the mixture of step (a). Preferably, the tip speed (tip speed=π×stirrer rotational speed×stirrer diameter) ranges from 0.2 to 10 meter per second (m/s), more preferably from 0.5 to 4 m/s and most preferably from 1 to 2 m/s.

In a preferred embodiment of step (b), the polymerization reaction is carried out in a cylindrical vessel equipped with baffles. The diameter to height ratio of the vessel may range from 4:1 to 1:2, more preferably the diameter to height ratio of the vessel ranges from 2:1 to 1:1.

Preferably, the reaction vessel is equipped with an axial flow stirrer selected from the group comprising pitched blade stirrer, marine type propeller, or Lightnin A-310. More preferably, the stirrer is a pitched blade stirrer.

Step (b) can be performed in a broad temperature range, preferably at a temperature from −10° C. to 100° C., more preferably at a temperature of 0° C. to 80° C., even more preferably at a temperature of 10° C. to 50° C. and most preferably at ambient temperature. "Ambient temperature" refers to the temperature present in a typical laboratory environment and preferably means a temperature ranging from 17 to 25° C.

Preferably, the hydrogel obtained from the polymerization is a shaped article, such as a coating, mesh, stent, nanoparticle or a microparticle. More preferably, the hydrogel is in the form of microparticular beads having a diameter from 1 to 500 micrometer, more preferably with a diameter from 10 to 300 micrometer, even more preferably with a diameter from 20 and 150 micrometer and most preferably with a diameter from 30 to 130 micrometer. The afore-mentioned diameters are measured when the hydrogel microparticles are fully hydrated in water.

In one embodiment the process for the preparation of a hydrogel further comprises the step of:
(c) working-up the hydrogel.
Step (c) comprises one or more of the following step(s):
(c1) removing excess liquid from the polymerization reaction,
(c2) washing the hydrogel to remove solvents used during polymerization,
(c3) transferring the hydrogel into a buffer solution,
(c4) size fractionating/sieving of the hydrogel,
(c5) transferring the hydrogel into a container,
(c6) drying the hydrogel,
(c7) transferring the hydrogel into a specific solvent suitable for sterilization, and
(c8) sterilizing the hydrogel, preferably by gamma radiation Preferably, step (c) comprises all of the following steps
(c1) removing excess liquid from the polymerization reaction,
(c2) washing the hydrogel to remove solvents used during polymerization,
(c3) transferring the hydrogel into a buffer solution,
(c4) size fractionating/sieving of the hydrogel,
(c5) transferring the hydrogel into a container,
(c7) transferring the hydrogel into a specific solvent suitable for sterilization, and
(c8) sterilizing the hydrogel, preferably by gamma radiation.

The at least one backbone reagent has a molecular weight ranging from 1 to 100 kDa, preferably from 2 to 50 kDa, more preferably from 5 and 30 kDa, even more preferably from 5 to 25 kDa and most preferably from 5 to 15 kDa.

Preferably, the backbone reagent is PEG-based comprising at least 10% PEG, more preferably comprising at least 20% PEG, even more preferably comprising at least 30% PEG and most preferably comprising at least 40% PEG.

In one embodiment the backbone reagent of step (a-i) is present in the form of its acidic salt, preferably in the form of an acid addition salt. Suitable acid addition salts are formed from acids which form non-toxic salts. Examples include but are not limited to the acetate, aspartate, benzoate, besylate, bicarbonate, carbonate, bisulphate, sulphate, borate, camsylate, citrate, edisylate, esylate, formate, fumarate, gluceptate, gluconate, glucuronate, hexafluorophosphate, hibenzate, hydrochloride, hydrobromide, hydroiodide, isethionate, lactate, malate, maleate, malonate, mesylate, methylsulphate, naphthylate, nicotinate, nitrate, orotate, oxalate, palmitate, pamoate, phosphate, hydrogen phosphate, dihydrogen phosphate, sacharate, stearate, succinate, tartrate and tosylate. Particularly preferred, the backbone reagent is present in the form of its hydrochloride salt.

In one embodiment, the at least one backbone reagent is selected from the group consisting of
a compound of formula (aI)

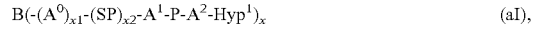

wherein
B is a branching core,
SP is a spacer moiety selected from the group consisting of $C_{1-6}$ alkyl, $C_{2-6}$ alkenyl and $C_{2-6}$ alkynyl,
P is a PEG-based polymeric chain comprising at least 80% PEG, preferably at least 85% PEG, more preferably at least 90% PEG and most preferably at least 95% PEG,
$Hyp^1$ is a moiety comprising an amine ($-NH_2$ and/or $-NH-$) or a polyamine comprising at least two amines ($-NH_2$ and/or $-NH-$), x is an integer from 3 to 16, x1, x2 are independently of each other 0 or 1, provided that x1 is 0, if x2 is 0, $A^0$, $A^1$, $A^2$ are independently of each other selected from the group consisting of

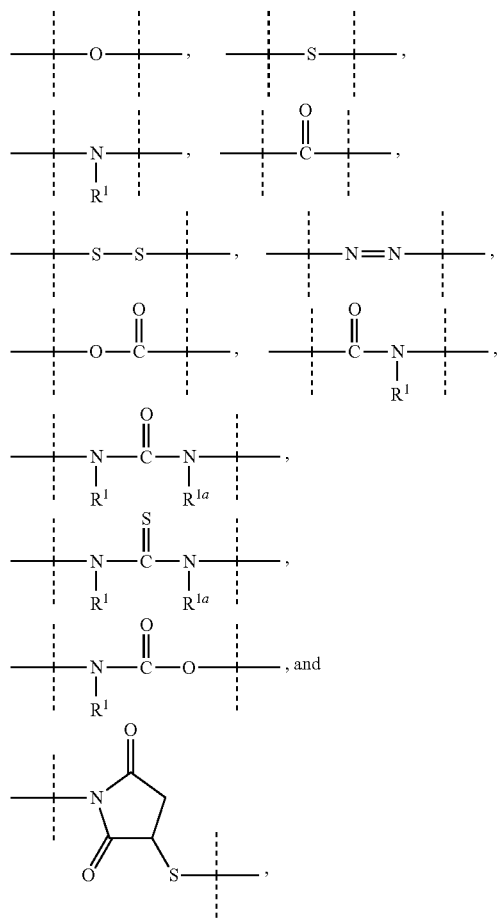

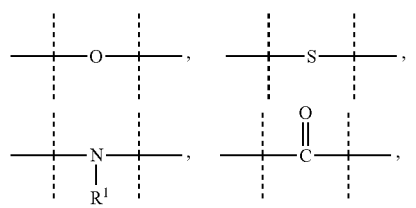

wherein $R^1$ and $R^{1a}$ are independently of each other selected from H and $C_{1-6}$ alkyl;

a compound of formula (aII)

 (aII), wherein

P is defined as above in the compound of formula (aI), $Hyp^2$, $Hyp^3$ are independently of each other a polyamine comprising at least two amines (—$NH_2$ and/or —NH—), and $A^3$ and $A^4$ are independently selected from the group consisting of

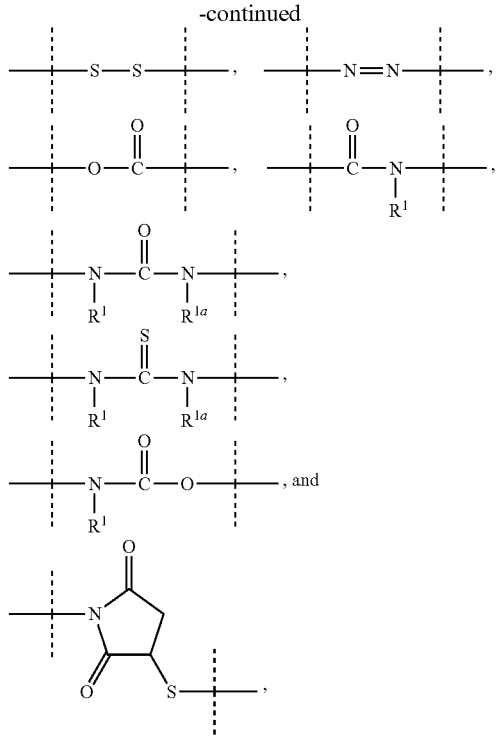

wherein $R^1$ and $R^{1a}$ are independently of each other selected from H and $C_{1-6}$ alkyl;

a compound of formula (aIII)

$P^1$-$A^5$-$Hyp^4$ (aIII), wherein $P^1$ is a PEG-based polymeric chain comprising at least 80% PEG, preferably at least 85% PEG, more preferably at least 90% PEG and most preferably at least 95% PEG, $Hyp^4$ is a polyamine comprising at least three amines (—$NH_2$ and/or —NH), and $A^5$ is selected from the group consisting of

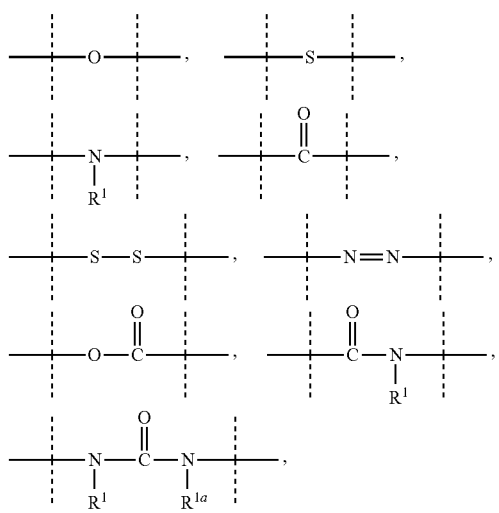

-continued

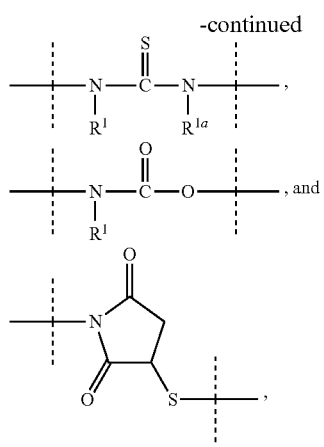

wherein $R^1$ and $R^{1a}$ are independently of each other selected from H and $C_{1-6}$ alkyl;
and
a compound of formula (aIV), $$T^1\text{-}A^6\text{-Hyp}^5 \qquad \text{(aIV)},$$

wherein
Hyp$^5$ is a polyamine comprising at least three amines (—NH$_2$ and/or —NH), and
$A^6$ is selected from the group consisting of

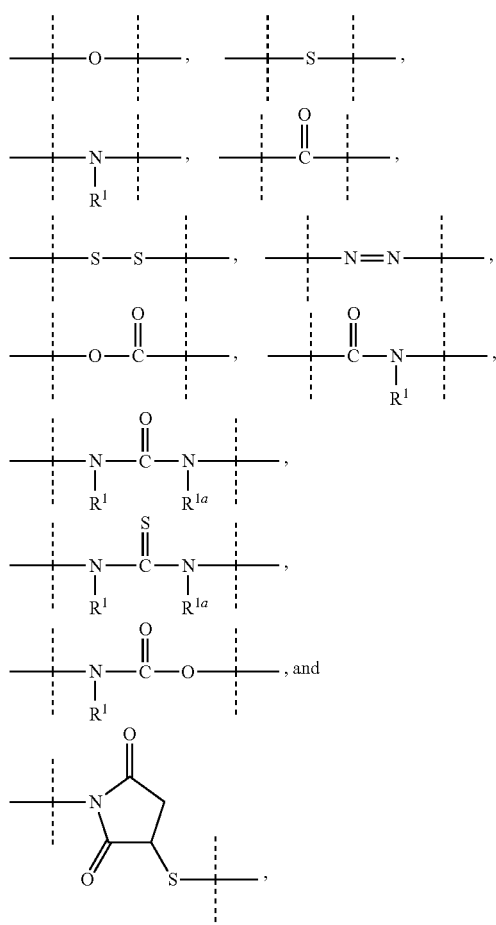

wherein $R^1$ and $R^{1a}$ are independently of each other selected from H and $C_{1-6}$ alkyl; and $T^1$ is selected from the group consisting of $C_{1-50}$ alkyl, $C_{2-50}$ alkenyl and $C_{2-50}$ alkynyl, which fragment is optionally interrupted by one or more group(s) selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 3- to 10-membered heterocyclyl, phenyl and naphthyl.

In the following sections the term "Hyp$^x$" refers to Hyp$^1$, Hyp$^2$, Hyp$^3$, Hyp$^4$ and Hyp$^5$ collectively.

Preferably, the backbone reagent is a compound of formula (aI), (aII) or (aIII), more preferably the backbone reagent is a compound of formula (aI) or (aIII), and most preferably the backbone reagent is a compound of formula (aI).

In a preferred embodiment, in a compound of formula (aI), x is 4, 6 or 8. Preferably, in a compound of formula (aI) x is 4 or 8, most preferably, x is 4.

In a preferred embodiment in the compounds of the formulas (aI) to (aIV), $A^0$, $A^1$, $A^2$, $A^3$, $A^4$, $A^5$ and $A^6$ are selected from the group comprising

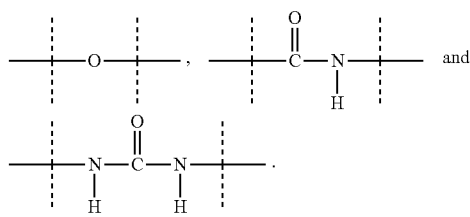

Preferably, in a compound of formula (aI) $A^0$ is

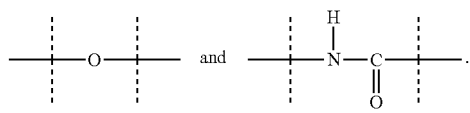

Preferably, in a compound of formula (aI) $A^1$ is

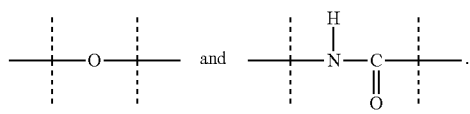

Preferably, in a compound of formula (aI) $A^2$ is

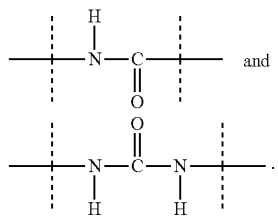

Preferably, in a compound of formula (aII) $A^3$ is

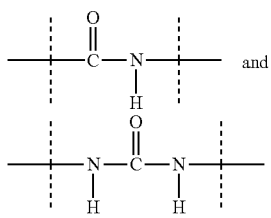 and and $A^4$ is

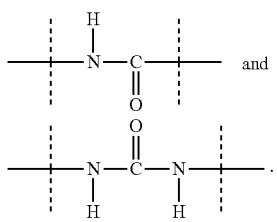

Preferably, in a compound of formula (aIII) $A^5$ is

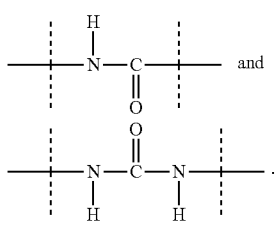

Preferably, in a compound of formula (aIV) $A^6$ is

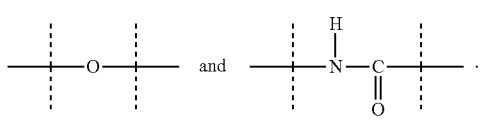

Preferably, in a compound of formula (aIV), $T^1$ is selected from H and $C_{1-6}$ alkyl.

In one embodiment, in a compound of formula (aI), the branching core B is selected from the following structures:

(a-i)

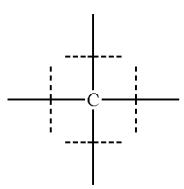

(a-ii)

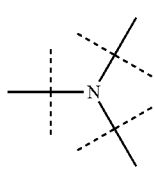

(a-iii)

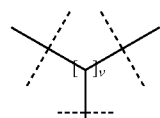

(a-iv)

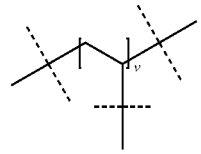

(a-v)

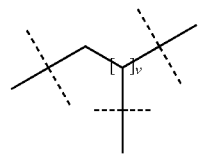

(a-vi)

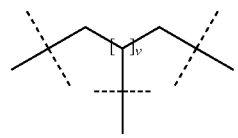

(a-vii)

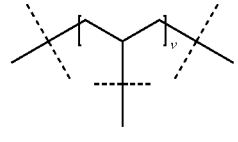

(a-viii)

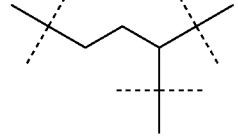

(a-ix)

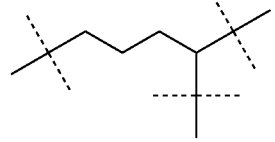

(a-x)

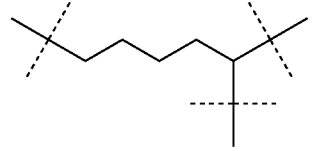

(a-xi)

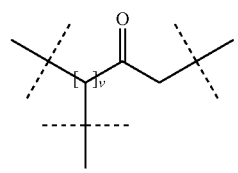

(a-xii)

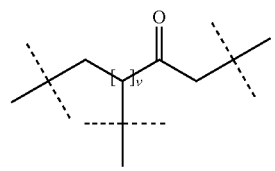

-continued (a-xiii)
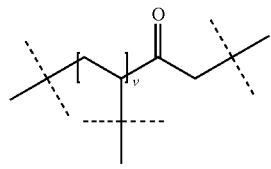

(a-xiv)
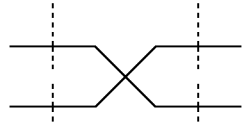

(a-xv)
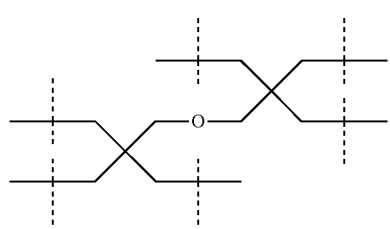

(a-xvi)
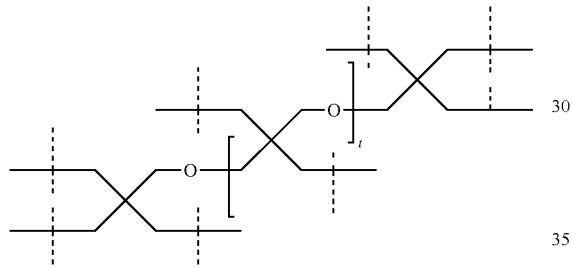

(a-xvii)
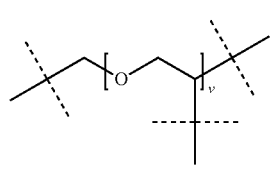

(a-xviii)
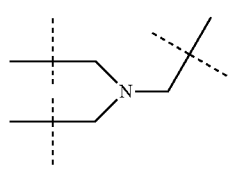

(a-xix)
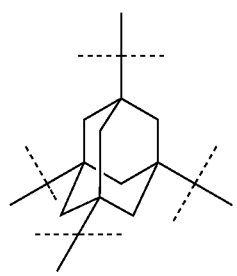

-continued (a-xx)
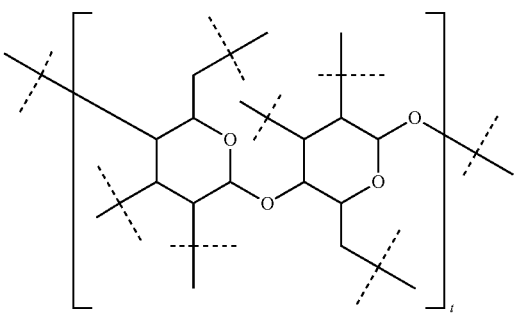

(a-xxi)
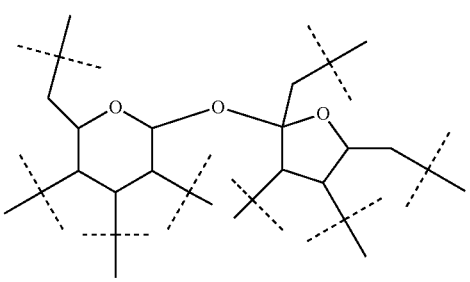

(a-xxii)
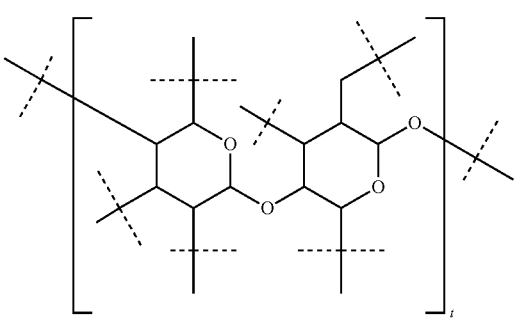

(a-xxiii)
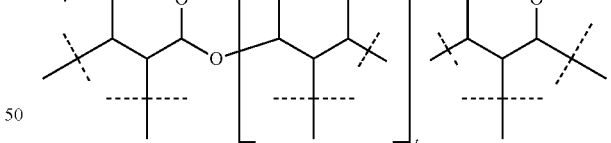

wherein dashed lines indicate attachment to $A^0$ or, if x1 and x2 are both 0, to $A^1$, t is 1 or 2; preferably t is 1, v is 1, 2, 3, 4, 5, 6, 7, 8, 9, 10, 11, 12, 13 or 14; preferably, v is 2, 3, 4, 5, 6; more preferably, v is 2, 4 or 6; most preferably, v is 2.

In a preferred embodiment, B has a structure of formula (a-i), (a-ii), (a-iii), (a-iv), (a-v), (a-vi), (a-vii), (a-viii), (a-ix), (a-x), (a-xiv), (a-xv) or (a-xvi). More preferably, B has a structure of formula (a-iii), (a-iv), (a-v), (a-vi), (a-vii), (a-viii), (a-ix), (a-x) or (a-iv). Most preferably, B has a structure of formula (a-xiv).

A preferred embodiment is a combination of B and $A^0$, or, if x1 and x2 are both 0 a preferred combination of B and $A^1$, which is selected from the following structures:

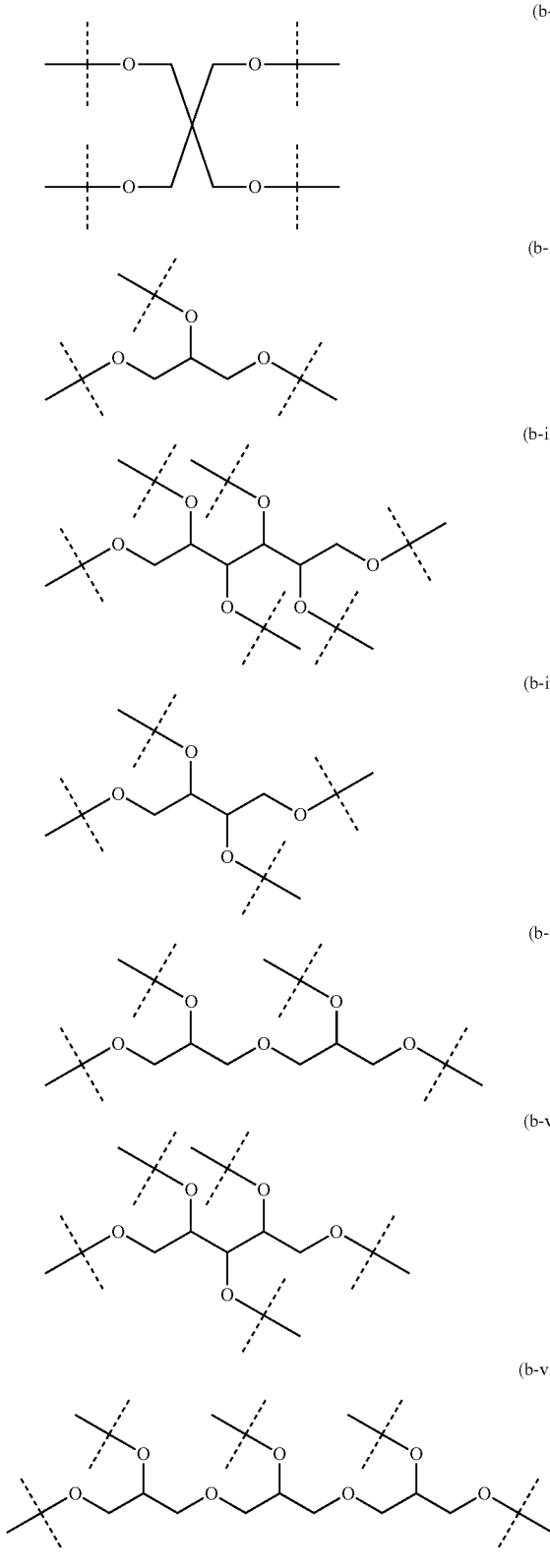

wherein
dashed lines indicate attachment to SP or, if x1 and x2 are both 0, to P.

More preferably, the combination of B and $A^0$ or, if x1 and x2 are both 0, the combination of B and $A^1$, has a structure of formula of formula (b-i), (b-iv), (b-vi) or (b-viii) and most preferably has a structure of formula of formula (b-i).

In one embodiment, x1 and x2 of formula (aI) are 0.

In one embodiment, the PEG-based polymeric chain P has a molecular weight from 0.3 kDa to 40 kDa; e.g. from 0.4 to 35 kDa, from 0.6 to 38 kDA, from 0.8 to 30 kDa, from 1 to 25 kDa, from 1 to 15 kDa or from 1 to 10 kDa. Most preferably P has a molecular weight from 1 to 10 kDa.

In one embodiment, the PEG-based polymeric chain $P^1$ has a molecular weight from 0.3 kDa to 40 kDa; e.g. from 0.4 to 35 kDa, from 0.6 to 38 kDA, from 0.8 to 30 kDa, from 1 to 25 kDa, from 1 to 15 kDa or from 1 to 10 kDa. Most preferably $P^1$ has a molecular weight from 1 to 10 kDa.

In one embodiment, in the compounds of formulas (aI) or (aII), P has the structure of formula (c-i):

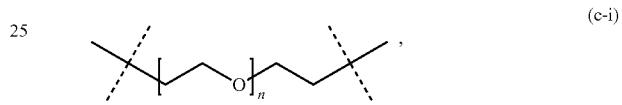

(c-i)

wherein n ranges from 6 to 900, more preferably n ranges from 20 to 700 and most preferably n ranges from 20 to 250.

In one embodiment, in the compounds of formulas (aIII), $P^1$ has the structure of formula (c-ii):

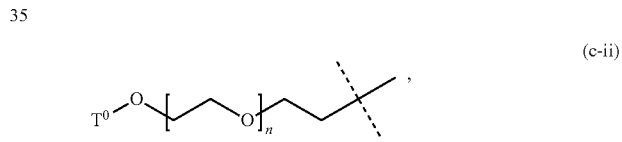

(c-ii)

wherein
n ranges from 6 to 900, more preferably n ranges from 20 to 700 and most preferably n ranges from 20 to 250;
$T^0$ is selected from the group comprising $C_{1-6}$ alkyl, $C_{2-6}$ alkenyl and $C_{2-6}$ alkynyl, which is optionally interrupted by one or more group(s) selected from —NH—, —N($C_{1-4}$ alkyl)-, —O—, —S—, —C(O)—, —C(O)NH—, —C(O)N($C_{1-4}$ alkyl)-, —O—C(O)—, —S(O)— and —S(O)$_2$—.

In one embodiment, in the compounds of formulas (aI) to (aIV), the moiety $Hyp^x$ is a polyamine and preferably comprises in bound form and, where applicable, in R- and/or S-configuration a moiety of the formulas (d-i), (d-ii), (d-iii) and/or (d-vi):

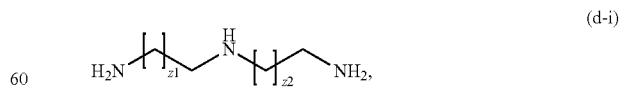

(d-i)

(d-ii)

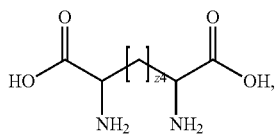
(d-iii)

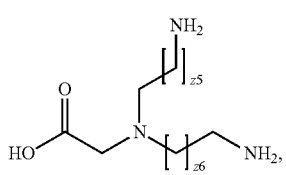
(d-iv)

wherein
z1, z2, z3, z4, z5, z6 are independently of each other 1, 2, 3, 4, 5, 6, 7 or 8.

More preferably, $Hyp^x$ comprises in bound form and in R- and/or S-configuration lysine, omithine, diaminoproprionic acid and/or diaminobutyric acid. Most preferably, $Hyp^x$ comprises in bound form and in R- and/or S-configuration lysine.

$Hyp^x$ has a molecular weight from 40 Da to 30 kDa, preferably from 0.3 kDa to 25 kDa, more preferably from 0.5 kDa to 20 kDa, even more preferably from 1 kDa to 20 kDa and most preferably from 2 kDa to 15 kDa.

$Hyp^x$ is preferably selected from the group consisting of a moiety of formula (e-i)

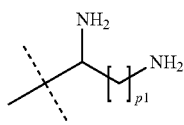
(e-i)

wherein
p1 is an integer from 1 to 5, preferably p1 is 4, and
the dashed line indicates attachment to $A^2$ if the backbone reagent has a structure of formula (aI) and to $A^3$ or $A^4$ if the backbone reagent has the structure of formula (aII);
a moiety of formula (e-ii)

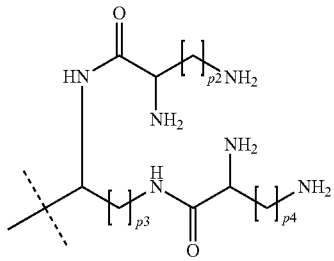
(e-ii)

wherein
p2, p3 and p4 are identical or different and each is independently of the others an integer from 1 to 5, preferably p2, p3 and p4 are 4, and
the dashed line indicates attachment to $A^2$ if the backbone reagent has a structure of formula (aI), to $A^3$ or $A^4$ if the backbone reagent has a structure of formula (aII), to $A^5$ if the backbone reagent has a structure of formula (aIII) and to $A^6$ if the backbone reagent has a structure of formula (aIV);
a moiety of formula (e-iii)

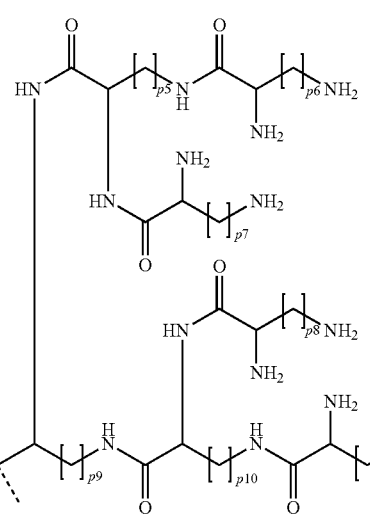
(e-iii)

wherein
p5 to p11 are identical or different and each is independently of the others an integer from 1 to 5, preferably p5 to p11 are 4, and
the dashed line indicates attachment to $A^2$ if the backbone reagent is of formula (aI), to $A^3$ or $A^4$ if the backbone reagent is of formula (aII), to $A^5$ if the backbone reagent is of formula (aIII) and to $A^6$ if the backbone reagent is of formula (aIV);
a moiety of formula (e-iv)

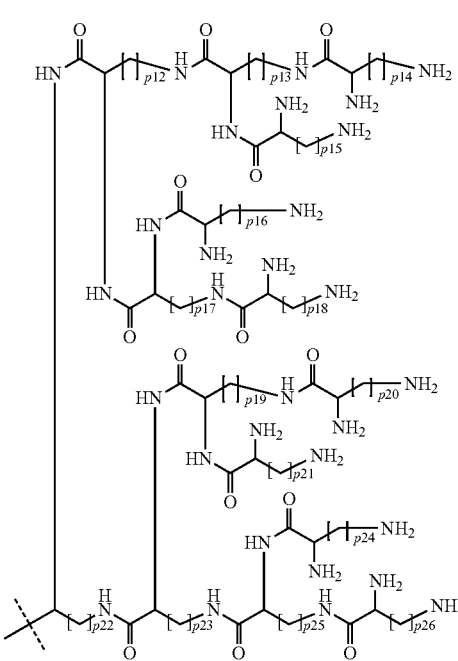
(e-iv)

wherein p12 to p26 are identical or different and each is independently of the others an integer from 1 to 5, preferably p12 to p26 are 4, and the dashed line indicates attachment to $A^2$ if the backbone reagent has a structure of formula (aI), to $A^3$ or $A^4$ if the backbone reagent has a structure of formula (aII), to $A^5$ if the backbone reagent has a structure of formula (aIII) and to $A^6$ if the backbone reagent has a structure of formula (aIV);

a moiety of formula (e-v)

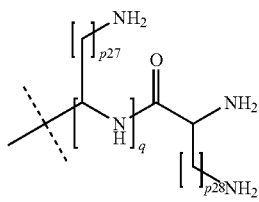

(e-v)

wherein p27 and p28 are identical or different and each is independently of the other an integer from 1 to 5, preferably p27 and p28 are 4, q is an integer from 1 to 8, preferably q is 2 or 6 and most preferably 1 is 6, and the dashed line indicates attachment to $A^2$ if the backbone reagent has a structure of formula (aI), to $A^3$ or $A^4$ if the backbone reagent has a structure of formula (aII), to $A^5$ if the backbone reagent has a structure of formula (aIII) and to $A^6$ if the backbone reagent has a structure of formula (aIV);

a moiety of formula (e-vi)

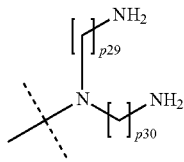

(e-vi)

wherein p29 and p30 are identical or different and each is independently of the other an integer from 2 to 5, preferably p29 and p30 are 3, and the dashed line indicates attachment to $A^2$ if the backbone reagent has the structure of formula (aI), to $A^3$ or $A^4$ if the backbone reagent has the structure of formula (aII), to $A^5$ if the backbone reagent has the structure of formula (aIII) and to $A^6$ if the backbone reagent has the structure of formula (aIV);

a moiety of formula (e-vii)

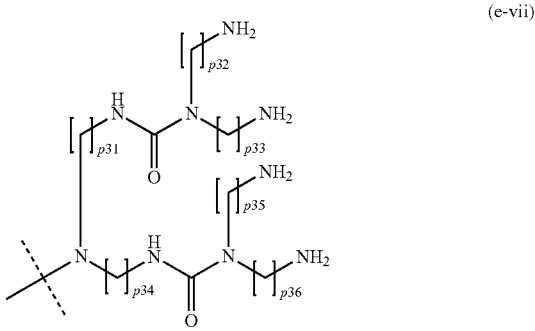

(e-vii)

wherein p31 to p36 are identical or different and each is independently of the others an integer from 2 to 5, preferably p31 to p36 are 3, and the dashed line indicates attachment to $A^2$ if the backbone reagent has a structure of formula (aI), to $A^3$ or $A^4$ if the backbone reagent has a structure of formula (aII), to $A^5$ if the backbone reagent has a structure of formula (aIII) and to $A^6$ if the backbone reagent has a structure of formula (aIV);

a moiety of formula (e-viii)

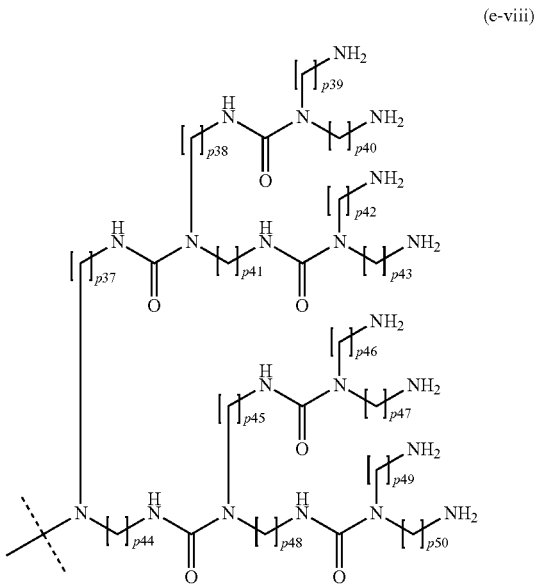

(e-viii)

wherein p37 to p50 are identical or different and each is independently of the others an integer from 2 to 5, preferably p37 to p50 are 3, and the dashed line indicates attachment to $A^2$ if the backbone reagent has a structure of formula (aI), to $A^3$ or $A^4$ if the backbone reagent has a structure of formula (aII), to $A^5$ if the backbone reagent has a structure of formula (aIII) and to $A^6$ if the backbone reagent has a structure of formula (aIV); and a moiety of formula (e-ix):

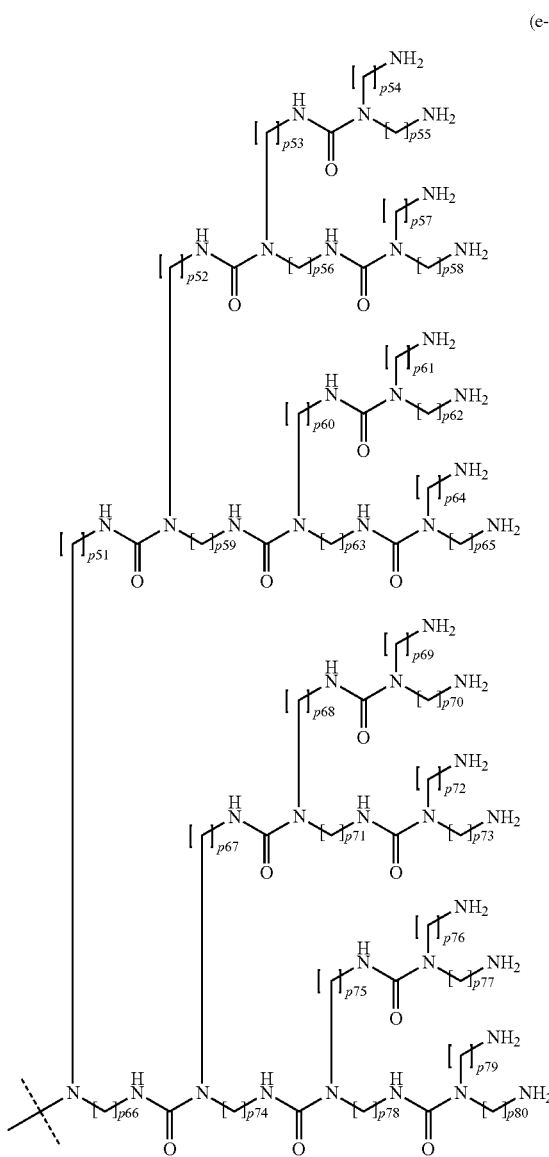

wherein
p51 to p80 are identical or different and each is independently of the others an integer from 2 to 5, preferably p51 to p80 are 3, and
the dashed line indicates attachment to $A^2$ if the backbone reagent has a structure of formula (aI), to $A^3$ or $A^4$ if the backbone reagent has a structure of formula (aII), to $A^5$ if the backbone reagent has a structure of formula (aIII) and to $A^6$ if the backbone reagent has a structure of formula (aIV); and
wherein the moieties (e-i) to (e-v) may at each chiral center be in either R- or S-configuration, preferably, all chiral centers of a moiety (e-i) to (e-v) are in the same configuration.

Preferably, $Hyp^x$ is has a structure of formulas (e-i), (e-ii), (e-iii), (e-iv), (e-vi), (e-vii), (e-viii) or (e-ix). More preferably, $Hyp^x$ has a structure of formulas (e-ii), (e-iii), (e-iv), (e-vii), (e-viii) or (e-ix), even more preferably $Hyp^x$ has a structure of formulas (e-ii), (e-iii), (e-vii) or (e-viii) and most preferably $Hyp^x$ has the structure of formula (e-iii).

If the backbone reagent has a structure of formula (aI), a preferred moiety $-A^2-Hyp^1$ is a moiety of the formula

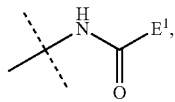

wherein
the dashed line indicates attachment to P; and
$E^1$ is selected from formulas (e-i) to (e-ix).

If the backbone reagent has a structure of formula (aII) a preferred moiety $Hyp^2-A^3-$ is a moiety of the formula

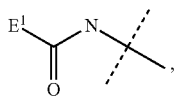

wherein
the dashed line indicates attachment to P; and
$E^1$ is selected from formulas (e-i) to (e-ix);
and a preferred moiety $-A^4-Hyp^3$ is a moiety of the formula

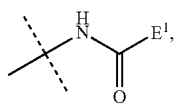

wherein
the dashed line indicates attachment to P; and
$E^1$ is selected from formulas (e-i) to (e-ix).

If the backbone reagent has a structure of formula (aII), a preferred moiety $-A^5-Hyp^4$ is a moiety of the formula

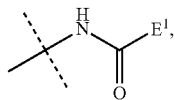

wherein
the dashed line indicates attachment to $P^1$; and
$E^1$ is selected from formulas (e-i) to (e-ix).

More preferably, the backbone reagent has a structure of formula (aI) and B has a structure of formula (a-xiv).

Even more preferably, the backbone reagent has the structure of formula (aI), B has the structure of formula (a-xiv), x1 and x2 are 0, and $A^1$ is —O—.

Even more preferably, the backbone reagent has the structure of formula (aI), B has the structure of formula (a-xiv), $A^1$ is —O—, and P has a structure of formula (c-i).

Even more preferably, the backbone reagent is formula (aI), B is of formula (a-xiv), x1 and x2 are 0, $A^1$ is —O—, P is of formula (c-i), $A^2$ is —NH—(C=O)— and $Hyp^1$ is of formula (e-iii).

Most preferably, the backbone reagent has the following formula:

prises at least two activated functional end groups which during the polymerization of step (b) react with the functional groups $A^{x0}$ of the at least one backbone reagent.

The crosslinker reagent has a molecular weight ranging from 0.5 to 40 kDa, more preferably ranging from 0.75 to 30 kDa, even more preferably ranging from 1 to 20 kDa, even more preferably ranging from 1 to 10 kDa, even more preferably ranging from 1 to 7.5 kDa and most preferably ranging from 2 kDa to 4 kDa.

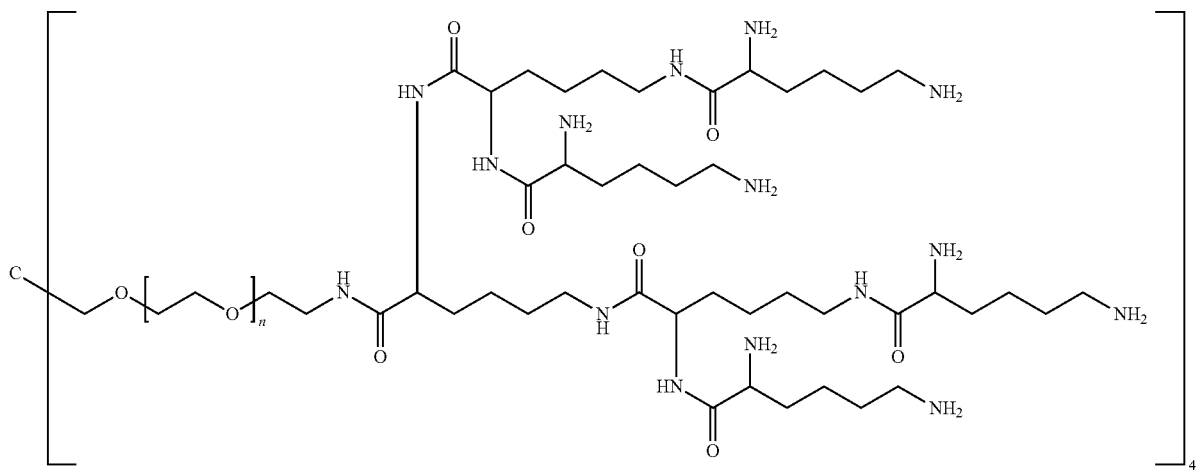

wherein n ranges from 10 to 40, preferably from 10 to 30, more preferably from 20 to 30 and most preferably n is 28.

SP is a spacer moiety selected from the group comprising $C_{1-6}$ alkyl, $C_{2-6}$ alkenyl and $C_{2-6}$ alkynyl, preferably SP is —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, —CH=CH— and —CH=CH—, most preferably SP is —$CH_2$—, —$CH_2$—$CH_2$— or —CH=CH—.

The at least one crosslinker reagent of step (a-ii) comprises at least one carbonyloxy group (—(C=O)—O— or —O—(C=O)—), which is/are (a) biodegradable linkage(s). Such biodegradable linkage renders the hydrogel biodegradable. Additionally, the at least one crosslinker reagent com- The crosslinker reagent comprises at least two activated functional end groups selected from the group comprising activated ester groups, activated carbamate groups, activated carbonate groups and activated thiocarbonate groups, which during polymerization react with the amine groups of the backbone reagents, forming amide linkages.

In one preferred embodiment, the crosslinker reagent is a compound of formula (V-I):

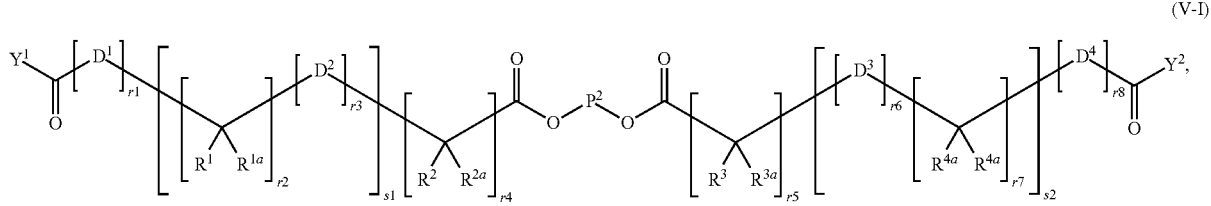
(V-I)

wherein each $D^1$, $D^2$, $D^3$ and $D^4$ are identical or different and each is independently of the others selected from the group comprising —O—, —$NR^5$—, —S— and —$CR^6R^{6a}$—;

each $R^1$, $R^{1a}$, $R^2$, $R^{2a}$, $R^3$, $R^{3a}$, $R^4$, $R^{4a}$, $R^6$ and $R^{6a}$ are identical or different and each is independently of the others selected from the group comprising —H, —$OR^7$, —$NR^7R^{7a}$, —$SR^7$ and $C_{1-6}$ alkyl; optionally, each of the pair(s) $R^1/R^2$, $R^3/R^4$, $R^{1a}/R^{2a}$, and $R^{3a}/R^{4a}$ may independently form a chemical bond and/or each of the pairs $R^1/R^{1a}R^2/R^{2a}$, $R^3/R^{3a}$, $R^4/R^{4a}$, $R^6/R^{6a}$, $R^1/R^2$, $R^3/R^4$, $R^{1a}/R^{2a}$, and $R^{3a}/R^{4a}$ are independently of each other joined together with the atoms to which they are attached to form a $C_{3-8}$ cycloalkyl or to form a ring A or are joined together with the atoms to which they are attached to form a 3- to 10-membered heterocyclyl or 8- to 11-membered heterobicyclyl or adamantyl;

each $R^5$ is independently selected from —H and $C_{1-6}$ alkyl; optionally, each of the pair(s) $R^1/R^5$, $R^2/R^5$, $R^3/R^5$, $R^4/R^5$ and $R^5/R^6$ may independently form a chemical bond and/or are joined together with the atoms to which they are attached to form a 3- to 10-membered heterocyclyl or 8- to 11-membered heterobicyclyl;

each $R^7$, $R^{7a}$ is independently selected from H and $C_{1-6}$ alkyl;

A is selected from the group consisting of indenyl, indanyl and tetralinyl;

$P^2$ is

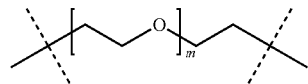

m ranges from 120 to 920, preferably from 120 to 460 and more preferably from 120 to 230;

r1, r2, r7, r8 are independently 0 or 1;
r3, r6 are independently 0, 1, 2, 3, or 4;
r4, r5 are independently 1, 2, 3, 4, 5, 6, 7, 8, 9 or 10;
s1, s2 are independently 1, 2, 3, 4, 5 or 6;
$Y^1$, $Y^2$ are identical or different and each is independently of the other selected from formulas (f-i) to (f-vii):

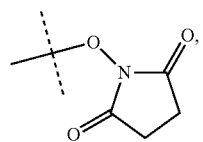

(f-i)

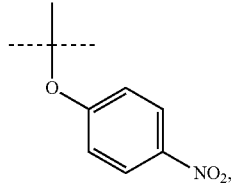

(f-ii)

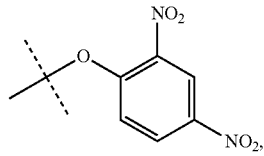

(f-iii)

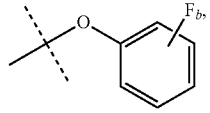

(f-iv)

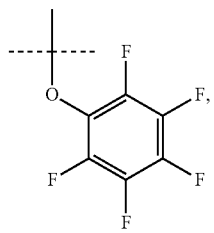

(f-v)

(f-vi)

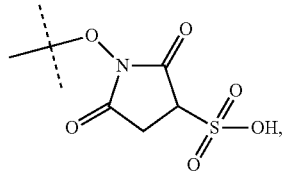

(f-vii)

wherein the dashed lines indicate attachment to the rest of the molecule, b is 1, 2, 3 or 4

$X^H$ is Cl, Br, I, or F.

Preferably, the crosslinker reagent is a compound of formula (V-II):

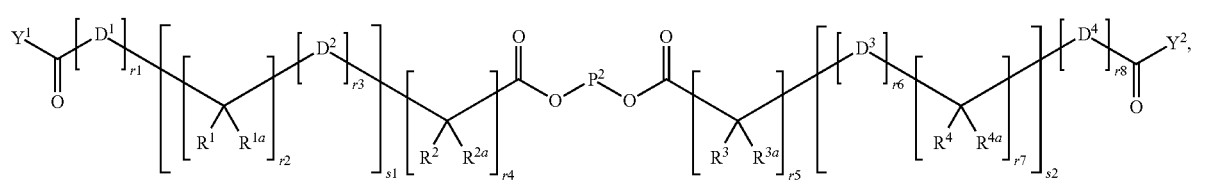

(V-II)

wherein

D$^1$, D$^2$, D$^3$ and D$^4$ are identical or different and each is independently of the others selected from the group comprising O, NR$^5$, S and CR$^5$R$^{5a}$;

R$^1$, R$^{1a}$, R$^2$, R$^{2a}$, R$^3$, R$^{3a}$, R$^4$, R$^{4a}$, R$^5$ and R$^{5a}$ are identical or different and each is independently of the others selected from the group comprising H and C$_{1-6}$ alkyl; optionally, one or more of the pair(s) R$^1$/R$^{1a}$, R$^2$/R$^{2a}$, R$^3$/R$^{3a}$, R$^4$/R$^{4a}$, R$^1$/R$^2$, R$^3$/R$^4$, R$^{1a}$/R$^{2a}$, and R$^{3a}$/R$^{4a}$ form a chemical bond or are joined together with the atom to which they are attached to form a C$_{3-8}$ cycloalkyl or to form a ring A or are joined together with the atom to which they are attached to form a 3- to 10-membered heterocyclyl or 8- to 11-membered heterobicyclyl or adamantyl;

A is selected from the group consisting of phenyl, naphthyl, indenyl, indanyl and tetralinyl;

P$^2$ is

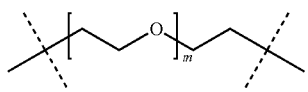

m ranges from 11 to 908, preferably from 17 to 680, even more preferably from 22 to 454, even more preferably from 22 to 227, even more preferably from 22 to 170 and more preferably from 45 to 90;

r1, r2, r7, r8 are independently 0 or 1;

r3, r6 are independently 0, 1, 2, 3, or 4;

r4, r5 are independently 1, 2, 3, 4, 5, 6, 7, 8, 9 or 10;

s1, s2 are independently 1, 2, 3, 4, 5 or 6;

Y$^1$, Y$^2$ are identical or different and each is independently of the other selected from formulas (f-i) to (f-vii):

(f-i)
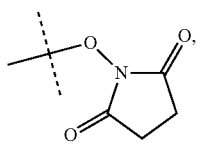

(f-ii)
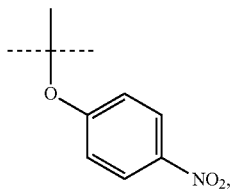

(f-iii)
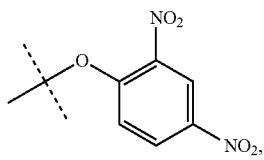

(f-iv)
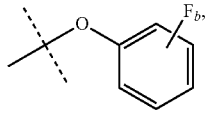

(f-v)
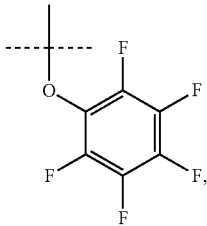

(f-vi)
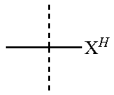

(f-vii)
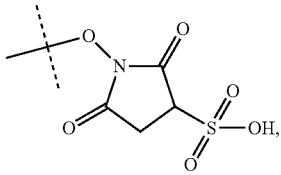

wherein the dashed lines indicate attachment to the rest of the molecule, b is 1, 2, 3 or 4

X$^H$ is Cl, Br, I, or F.

It is understood that the moieties

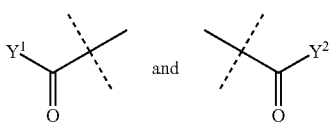

represent the at least two activated functional end groups.

Preferably, Y$^1$ and Y$^2$ of formula (V-I) or (V-II) have a structure of formula (f-i), (f-ii) or (f-v). More preferably, Y$^1$ and Y$^2$ of formula (V-I) or (V-II) have a structure of formula (f-i) or (f-ii) and most preferably, Y$^1$ and Y$^2$ have a structure of formula (f-i).

Preferably, both moieties Y$^1$ and Y$^2$ of formula (V-I) or (V-II) have the same structure. More preferably, both moieties Y$^1$ and Y$^2$ have the structure of formula (f-i).

Preferably, r1 of formula (V-I) or (V-II) is 0.

Preferably, r1 and s1 of formula (V-I) or (V-II) are both 0.

Preferably, one or more of the pair(s) R$^1$/R$^{1a}$, R$^2$/R$^{2a}$, R$^3$/R$^{3a}$, R$^4$/R$^{4a}$, R$^1$/R$^2$, R$^3$/R$^4$, R$^{1a}$/R$^{2a}$, and R$^{3a}$/R$^{4a}$ of formula (V-I) or (V-II) form a chemical bond or are joined together with the atom to which they are attached to form a C$_{3-8}$ cycloalkyl or form a ring A.

Preferably, one or more of the pair(s) R$^1$/R$^2$, R$^{1a}$/R$^{2a}$, R$^3$/R$^4$, R$^{3a}$/R$^{4a}$ of formula (V-I) or (V-II) are joined together with the atoms to which they are attached to form a 3- to 10-membered heterocyclyl or 8- to 11-membered heterobicyclyl.

Preferably, the crosslinker reagent of formula (V-I) and (V-II) is symmetric, i.e. the moiety
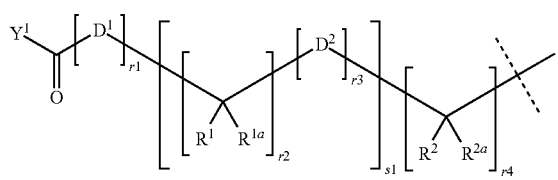
has the same structure as the moiety
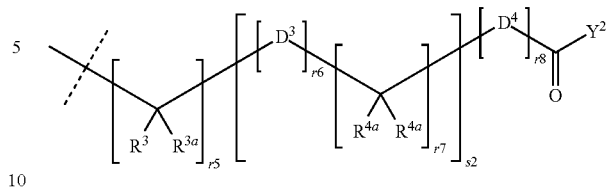
In one preferred embodiment s1, s2, r1 and r8 of formula (V-I) and (V-II) are 0.
In another preferred embodiment s1, s2, r1 and r8 of formula (V-I) and (V-II) are 0 and r4 of formula (V-I) and (V-II) and r5 are 1.
Preferred crosslinker reagents are of formula (V-1) to (V-54):
(V-1)
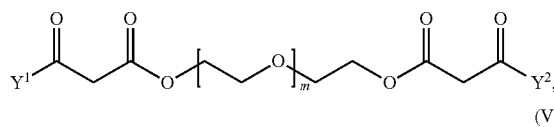
(V-2)
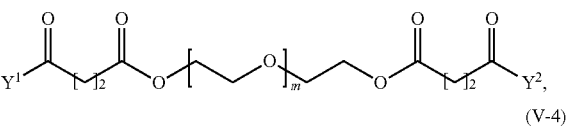
(V-3)
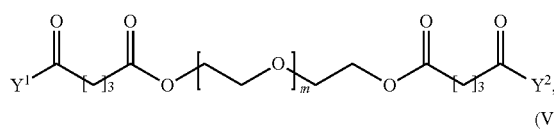
(V-4)
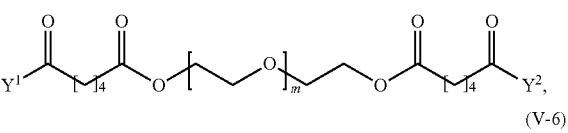
(V-5)
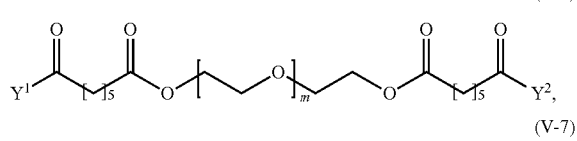
(V-6)
(V-7)
(V-8)
(V-9)
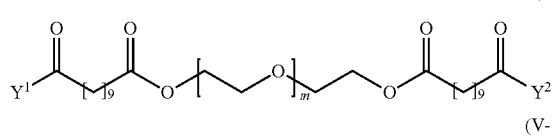
(V-10)
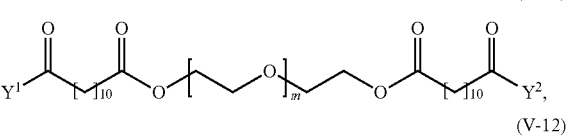
(V-11)
(V-12)
(V-13)
(V-14)
(V-15)
(V-16)

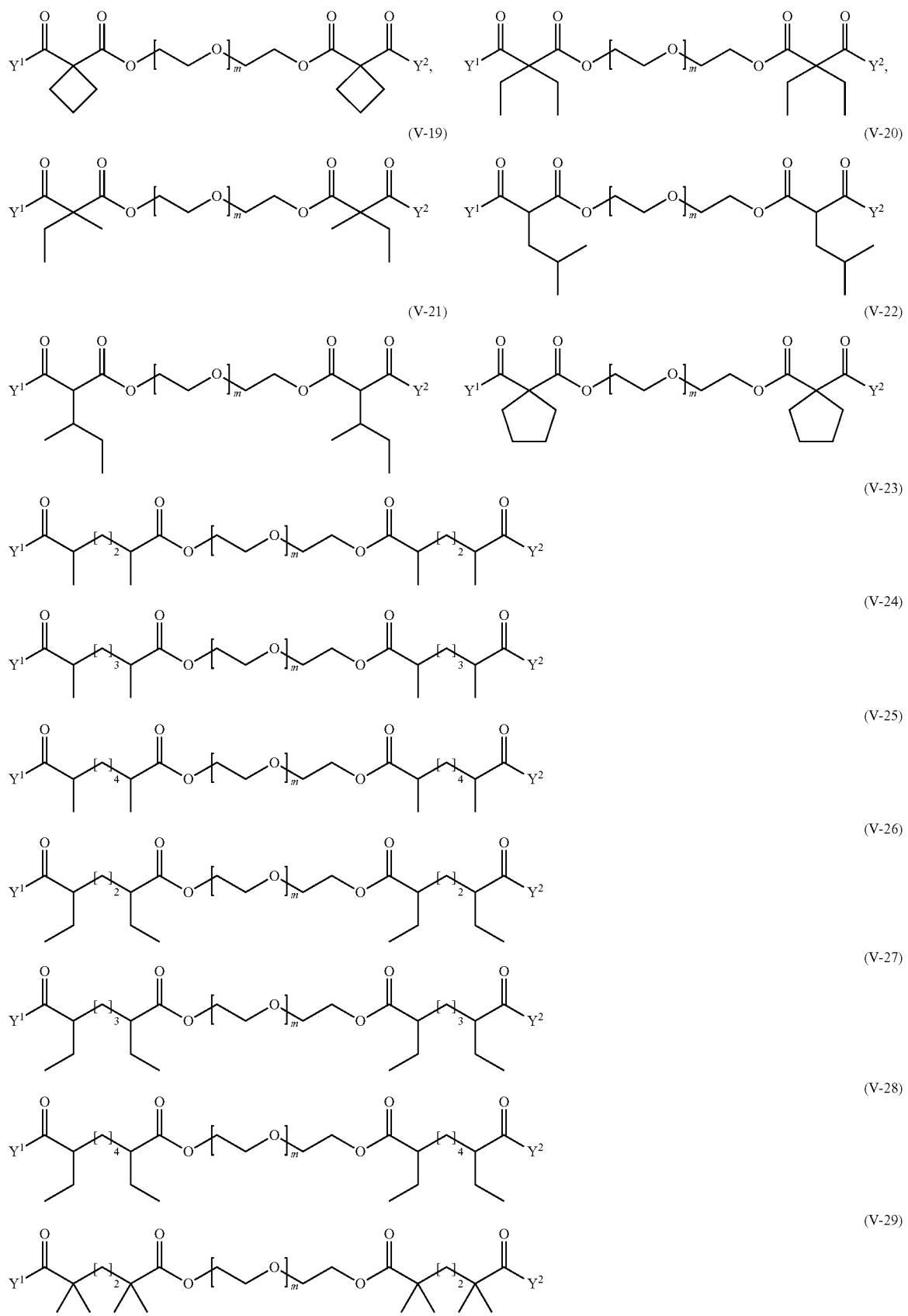

-continued
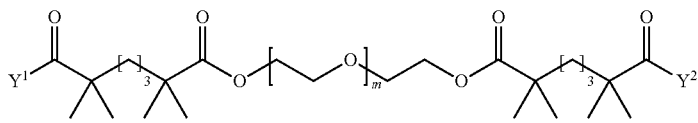
(V-30)
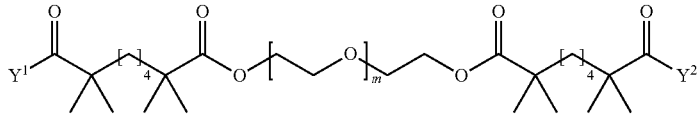
(V-31)
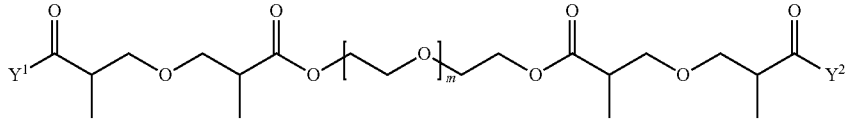
(V-32)
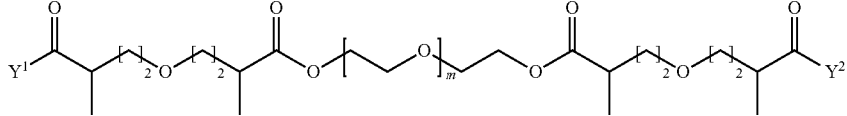
(V-33)
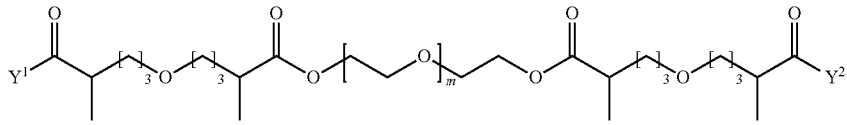
(V-34)
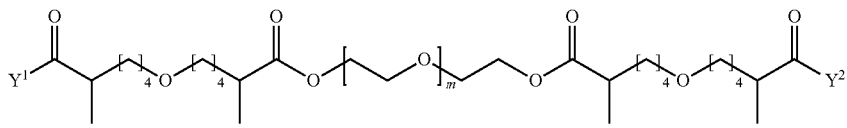
(V-35)
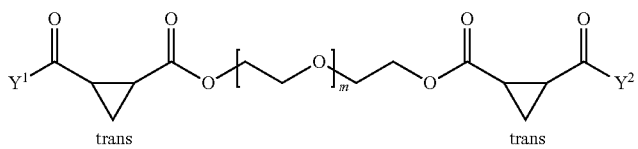
(V-36)
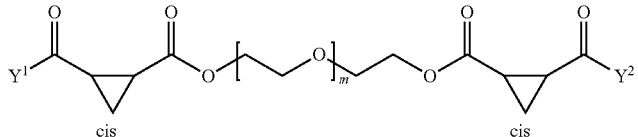
(V-37)
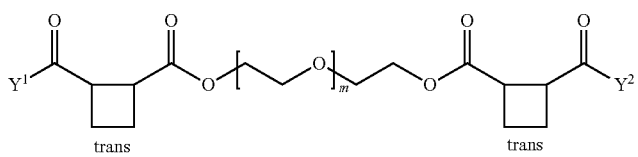
(V-38)
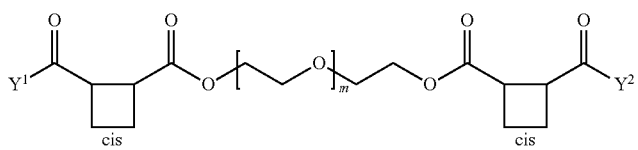
(V-39)
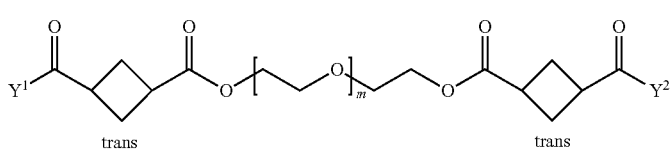
(V-40)

-continued
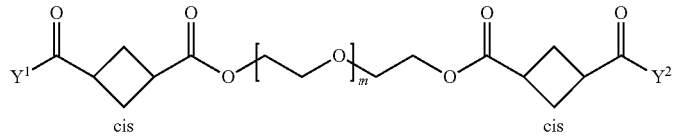
(V-41)
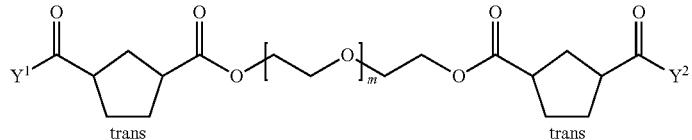
(V-42)
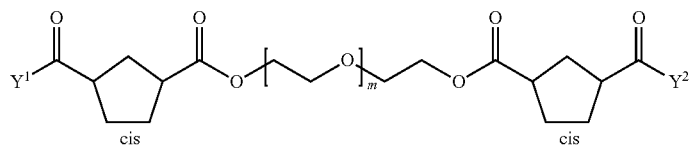
(V-43)
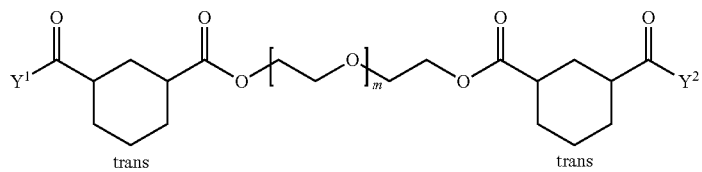
(V-44)
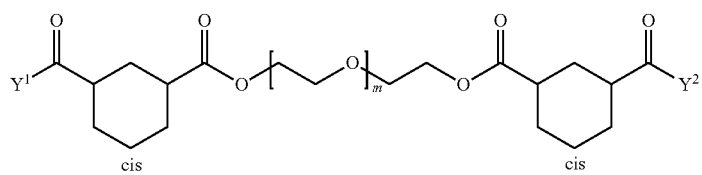
(V-45)
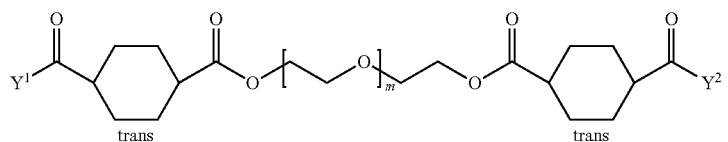
(V-46)
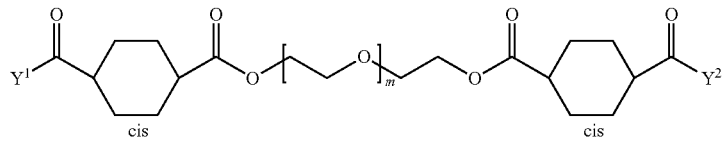
(V-47)
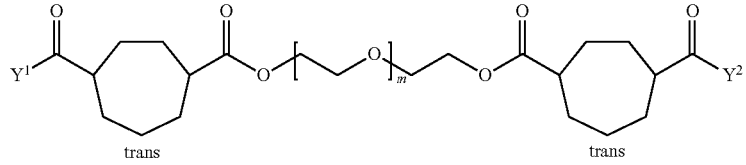
(V-48)
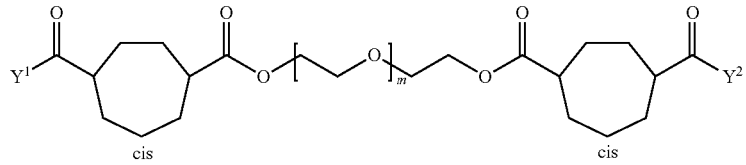
(V-49)

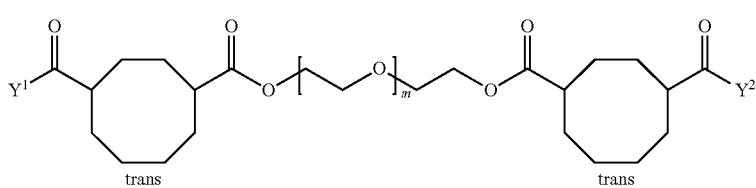

(V-50)

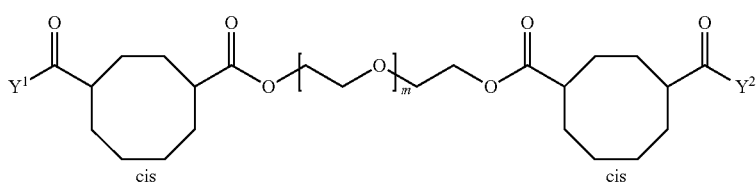

(V-51)

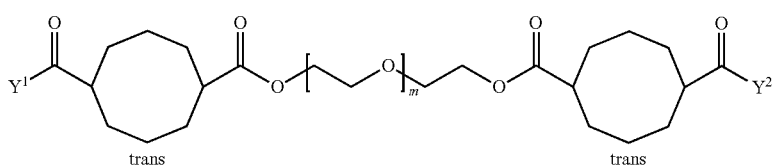

(V-52)

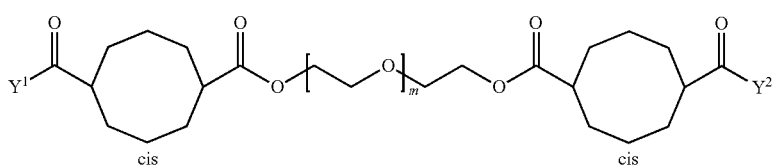

(V-53)

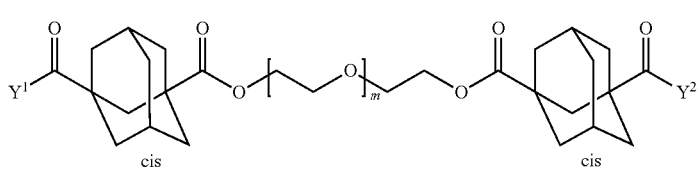

(V-54)

wherein
each crosslinker reagent may be in the form of its racemic mixture, where applicable; and m, $Y^1$ and $Y^2$ are defined as above.

Crosslinker reagents V-11 to V-54, V-1 and V-2 are preferred crosslinker reagents. Crosslinker reagents Va-11 to Va-54, Va-1 and Va-2 are most preferred crosslinker reagents. Most preferred is crosslinker reagent Va-14.

In another embodiment, crosslinker reagents V-1, V-2, V-5, V-6, V-7, V-8, V-9, V-10, V-11, V-12, V-13, V-14, V-15, V-16, V-17, V-18, V-19, V-20, V-21, V-22, V-23, V-24, V-25, V-26, V-27, V-28, V-29, V-30, V-31, V-32, V-33, V-34, V-35, V-36, V-37, V-38, V-39, V-40, V-41, V-42, V-43, V-44, V-45, V-46, V-47, V-48, V-49, V-50, V-51, V-52, V-53 an V-54 are preferred crosslinker reagents. More preferably, the at least one crosslinker reagent is of formula V-5, V-6, V-7, V-8, V-9, V-10, V-14, V-22, V-23, V-43, V-44, V-45 or V-46, and most preferably, the at least one crosslinker reagent is of formula V-5, V-6, V-9 or V-14.

The preferred embodiments of the compound of formula (V-I) and (V-II) as mentioned above apply accordingly to the preferred compounds of formulas (V-1) to (V-53).

In a preferred embodiment, the hydrogel comprises $A^{x0}$ in the form of primary or secondary amine functional groups. Preferably, such hydrogel contains from 0.01 to 1 mmol/g primary amine groups (—$NH_2$), more preferably, from 0.02 to 0.5 mmol/g primary amine groups and most preferably from 0.05 to 0.3 mmol/g primary amine groups. The term "X mmol/g primary amine groups" means that 1 g of dry hydrogel comprises X mmol primary amine groups. Measurement of the amine content of the hydrogel is carried out according to Gude et al. (Letters in Peptide Science, 2002, 9(4): 203-206, which is incorporated by reference in its entirety).

Preferably, the term "dry" as used herein means having a residual water content of a maximum of 10%, preferably less than 5% and more preferably less than 2% (determined according to Karl Fischer). The preferred method of drying is lyophilization.

It is understood that the hydrogel may be modified by conjugating certain moieties other than $L^1$ to remaining functional groups $A^{x0}$, such as for example spacer moieties and/or polymers and that also such modified hydrogel may be one embodiment of Z.

In a preferred embodiment Z is a hydrogel obtainable from the process for the preparation of a hydrogel as detailed above which is modified by conjugating a spacer moiety to remaining functional groups $A^{x0}$.

Such spacer moiety is preferably selected from the group consisting of -T-, —C(O)O—, —O—, —C(O)—, —C(O)N($R^{z1}$)—, —S(O)$_2$N($R^{z1}$)—, —S(O)N($R^{z1}$)—, —S(O)$_2$—, —S(O)—, —N($R^{z1}$)S(O)$_2$N($R^{z1a}$)—, —S—, —N($R^{z1}$)—, —OC(O$R^{z1}$)($R^{z1a}$)—, —N($R^{z1}$)C(O)N($R^{z1a}$)—, —OC(O)N ($R^{z1}$)—, $C_{1-50}$ alkyl, $C_{2-50}$ alkenyl, and $C_{2-50}$ alkynyl;

wherein -T-, $C_{1-50}$ alkyl, $C_{2-50}$ alkenyl, and $C_{2-50}$ alkynyl are optionally substituted with one or more $R^{z2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{z3}$)—, —S(O)$_2$N ($R^{z3}$)—, —S(O)N($R^{z3}$)—, —S(O)$_2$—, —S(O)—, —N($R^{z3}$) S(O)$_2$N($R^{3a}$)—, —S—, —N($R^{z3}$)—, —OC(O$R^{z3}$)($R^{z3a}$)—, —N($R^{z3}$)C(O)N($R^{z3a}$)—, and —OC(O)N($R^{z3}$)—;

$R^{z1}$ and $R^{z1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more $R^{z2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{z4}$)—, —S(O)$_2$N($R^{z4}$)—, —S(O)N($R^{z4}$)—, —S(O)$_2$—, —S(O)—, —N($R^{z4}$)S(O)$_2$N($R^{z4a}$)—, —S—, —N($R^{z4}$)—, —OC(O$R^{z4}$)($R^{z4a}$)—, —N($R^{z4}$)C(O)N ($R^{z4a}$)—, and —OC(O)N($R^{z4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8-to 30-membered carbopolycyclyl, and 8- to 30-membered heteropolycyclyl; wherein each T is independently optionally substituted with one or more $R^{z2}$, which are the same or different;

each $R^{z2}$ is independently selected from the group consisting of halogen, —CN, oxo (=O), —COO$R^{z5}$, —O$R^{z5}$, —C(O)$R^{z5}$, —C(O)N($R^{z5}R^{z5a}$), —S(O)$_2$N($R^{z5}R^{z5a}$), —S(O)N($R^{z5}R^{z5a}$), —S(O)$_2R^{z5}$, —S(O)$R^{z5}$, —N($R^{z5}$) S(O)$_2$N($R^{z5a}R^{z5b}$), —S$R^{z5}$, —N($R^{z5}R^{z5a}$), —NO$_2$, —OC (O)$R^{z5}$, —N($R^{z5}$)C(O)$R^{z5a}$, —N($R^{z5}$)S(O)$_2R^{z5a}$, —N($R^{z5}$)S (O)$R^{z5a}$, —N($R^{z5}$)C(O)O$R^{z5a}$, —N($R^{z5}$)C(O)N($R^{z5a}R^{z5b}$), —OC(O)N($R^{z5}R^{z5a}$), and $C_{1-6}$ alkyl; wherein $C_{1-6}$ alkyl is optionally substituted with one or more halogen, which are the same or different;

each $R^{z3}$, $R^{z3a}$, $R^{z4}$, $R^{z4a}$, $R^{z5}$, $R^{z5a}$ and $R^{z5b}$ is independently selected from the group consisting of —H, and $C_{1-6}$ alkyl; wherein $C_{1-6}$ alkyl is optionally substituted with one or more halogen, which are the same or different.

In the prodrugs, their pharmaceutically acceptable salts and the prodrug reagents of the present invention -L$^2$- and -L$^{2'}$- of formula (I), (I'), (Ia), (Ib), (I'a), (I'b), (IIa) and (IIa') are independently of each other a chemical bond or a spacer moiety.

When -L$^2$- and -L$^{2'}$- are other than a single chemical bond, -L$^2$- and -L$^{2'}$- are preferably independently of each other selected from the group consisting of -T-, —C(O)O—, —O—, —C(O)—, —C(O)N($R^{y1}$)—, —S(O)$_2$N($R^{y1}$)—, —S(O)N($R^{y1}$)—, —S(O)$_2$—, —S(O)—, —N($R^{y1}$)S(O)$_2$N ($R^{y1a}$)—, —S—, —N($R^{y1}$)—, —OC(O$R^{y1}$)($R^{y1a}$)—, —N($R^{y1}$)C(O)N($R^{y1a}$)—, —OC(O)N($R^{y1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more $R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y3}$)—, —S(O)$_2$N($R^{y3}$)—, —S(O)N($R^{y3}$)—, —S(O)$_2$—, —S(O)—, —N($R^{y3}$)S(O)$_2$N($R^{y3a}$)—, —S—, —N($R^{y3}$)—, —OC(O$R^{y3}$)($R^{y3a}$)—, —N($R^{y3}$)C(O)N($R^{y3a}$)—, and —OC(O)N($R^{y3}$)—;

$R^{y1}$ and $R^{y1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more $R^{y2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y4}$)—, —S(O)$_2$N($R^{y4}$)—, —S(O)N($R^{y4}$)—, —S(O)$_2$—, —S(O)—, —N($R^{y4}$)S(O)$_2$N($R^{y4a}$)—, —S—, —N($R^{y4}$)—, —OC(O$R^{y4}$)($R^{y4a}$)—, —N($R^{y4}$)C(O)N ($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8-to 30-membered carbopolycyclyl, and 8- to 30-membered heteropolycyclyl; wherein each T is independently optionally substituted with one or more $R^{y2}$, which are the same or different;

each $R^{y2}$ is independently selected from the group consisting of halogen, —CN, oxo (=O), —COO$R^{y5}$, —O$R^{y5}$, —C(O)$R^{y5}$, —C(O)N($R^{y5}R^{y5a}$), —S(O)$_2$N($R^{y5}R^{y5a}$), —S(O)N($R^{y5}R^{y5a}$), —S(O)$_2R^{y5}$, —S(O)$R^{y5}$, —N($R^{y5}$) S(O)$_2$N($R^{y5a}R^{y5b}$), —S$R^{y5}$, —N($R^{y5}R^{y5a}$), —NO$_2$, —OC (O)$R^{y5}$, —N($R^{y5}$)C(O)$R^{y5a}$, —N($R^{y5}$)S(O)$_2R^{y5a}$, —N($R^{y5}$) S(O)$R^{y5a}$, —N($R^{y5}$)C(O)O$R^{y5a}$, —N($R^{y5}$)C(O)N ($R^{y5a}R^{y5b}$), —OC(O)N($R^{y5}R^{y5a}$), and $C_{1-6}$ alkyl; wherein $C_{1-6}$ alkyl is optionally substituted with one or more halogen, which are the same or different; and each $R^{y3}$, $R^{y3a}$, $R^{y4}$, $R^{y4a}$, $R^{y5}$, $R^{y5a}$ and $R^{y5b}$ is independently selected from the group consisting of —H, and $C_{1-6}$ alkyl, wherein $C_{1-6}$ alkyl is optionally substituted with one or more halogen, which are the same or different.

When -L$^2$- and -L$^{2'}$- are other than a single chemical bond, -L$^2$- and -L$^{2'}$- are even more preferably independently of each selected from -T-, —C(O)O—, —O—, —C(O)—, —C(O)N($R^{y1}$)—, —S(O)$_2$N($R^{y1}$)—, —S(O)N($R^{y1}$)—, —S(O)$_2$—, —S(O)—, —N($R^{y1}$)S(O)$_2$N($R^{y1a}$)—, —S—, —N($R^{y1}$)—, —OC(O$R^{y1}$)($R^{y1a}$)—, —N($R^{y1}$)C(O)N ($R^{y1a}$)—, —OC(O)N($R^{y1}$)—, $C_{1-50}$ alkyl, $C_{2-50}$ alkenyl, and $C_{2-50}$ alkynyl; wherein -T-, $C_{1-20}$ alkyl, $C_{2-20}$ alkenyl, and $C_{2-20}$ alkynyl are optionally substituted with one or more $R^{y2}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{y3}$)—, —S(O)$_2$N($R^{y3}$)—, —S(O)N($R^{y3}$)—, —S(O)$_2$—, —S(O)—, —N($R^{y3}$)S(O)$_2$N($R^{y3a}$)—, —S—, —N($R^{y3}$)—, —OC (O$R^{y3}$)($R^{y3a}$)—, —N($R^{y3}$)C(O)N($R^{y3a}$)—, and —OC(O)N ($R^{y3}$)—;

$R^{y1}$ and $R^{y1a}$ are independently of each other selected from the group consisting of —H, -T, $C_{1-10}$ alkyl, $C_{2-10}$ alkenyl, and $C_{2-10}$ alkynyl; wherein -T, $C_{1-10}$ alkyl, $C_{2-10}$ alkenyl, and $C_{2-10}$ alkynyl are optionally substituted with one or more $R^{y2}$, which are the same or different, and wherein $C_{1-10}$ alkyl, $C_{2-10}$ alkenyl, and $C_{2-10}$ alkynyl are optionally interrupted by one or more groups selected from the group consisting of -T-, —C(O)O—, —O—, —C(O)—, —C(O)N($R^{y4}$)—, —S(O)$_2$N($R^{y4}$)—, —S(O)N($R^{y4}$)—, —S(O)$_2$—, —S(O)—, —N($R^{y4}$)S(O)$_2$N($R^{y4a}$)—, —S—, —N($R^{y4}$)—, —OC(O$R^{y4}$)($R^{y4a}$)—, —N($R^{y4}$)C(O)N ($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8-to 30-membered carbopolycyclyl, and 8- to 30-membered heteropolycyclyl; wherein each T is independently optionally substituted with one or more $R^{y2}$, which are the same or different;

$R^{y2}$ is selected from the group consisting of halogen, —CN, oxo (=O), —COOR$^{y5}$, —OR$^{y5}$, —C(O)R$^{y5}$, —C(O)N(R$^{y5}$R$^{y5a}$), —S(O)$_2$N(R$^{y5}$R$^{y5a}$), —S(O)N(R$^{y5}$R$^{y5a}$), —S(O)$_2$R$^{y5}$, —S(O)R$^{y5}$, —N(R$^{y5}$)S(O)$_2$N(R$^{y5a}$R$^{y5b}$), —SR$^{y5}$, —N(R$^{y5}$R$^{y5a}$), —NO$_2$, —OC(O)R$^{y5}$, —N(R$^{y5}$)C(O)R$^{y5a}$, —N(R$^{y5}$)S(O)$_2$R$^{y5a}$, —N(R$^{y5}$)S(O)R$^{y5a}$, —N(R$^{y5}$)C(O)OR$^{y5a}$, —N(R$^{y5}$)C(O)N(R$^{y5a}$R$^{y5b}$), —OC(O)N(R$^{y5}$R$^{y5a}$), and $C_{1-6}$ alkyl; wherein $C_{1-6}$ alkyl is optionally substituted with one or more halogen, which are the same or different; and each $R^{y3}$, $R^{y3a}$, $R^{y4}$, $R^{y4a}$, $R^{y5}$, $R^{y5a}$ and $R^{y5b}$ is independently of each other selected from the group consisting of —H, and $C_{1-6}$ alkyl; wherein $C_{1-6}$ alkyl is optionally substituted with one or more halogen, which are the same or different.

When -L$^2$- and -L$^{2'}$- are other than a single chemical bond, -L$^2$- and -L$^{2'}$- are even more preferably independently of each other selected from the group consisting of -T-, —C(O)O—, —O—, —C(O)—, —C(O)N(R$^{y1}$)—, —S(O)$_2$N(R$^{y1}$)—, —S(O)N(R$^{y1}$)—, —S(O)$_2$—, —S(O)—, —N(R$^{y1}$)S(O)$_2$N(R$^{y1a}$)—, —S—, —N(R$^{y1}$)—, —OC(OR$^{y1}$)(R$^{y1a}$)—, —N(R$^{y1}$)C(O)N(R$^{y1a}$)—, —OC(O)N(R$^{y1}$)—, $C_{1-50}$ alkyl, $C_{2-50}$ alkenyl, and $C_{2-50}$ alkynyl; wherein -T-, $C_{1-20}$ alkyl, $C_{2-20}$ alkenyl, and $C_{2-20}$ alkynyl are optionally substituted with one or more R$^{y2}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{y3a}$)—, —S—, —N(R$^{y3}$)—, —OC(OR$^{y3}$)(R$^{y3a}$)—, —N(R$^{y3}$)C(O)N(R$^{y3a}$)—, and —OC(O)N(R$^{y3}$)—;

$R^{y1}$ and $R^{y1a}$ are independently selected from the group consisting of —H, -T, $C_{1-10}$ alkyl, $C_{2-10}$ alkenyl, and $C_{2-10}$ alkynyl;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8-to 30-membered carbopolycyclyl, and 8- to 30-membered heteropolycyclyl;

each R$^{y2}$ is independently selected from the group consisting of halogen, and $C_{1-6}$ alkyl; and each $R^{y3}$, $R^{y3a}$, $R^{y4}$, $R^{y4a}$, $R^{y5}$, $R^{y5a}$ and $R^{y5b}$ is independently of each other selected from the group consisting of —H, and $C_{1-6}$ alkyl; wherein $C_{1-6}$ alkyl is optionally substituted with one or more halogen, which are the same or different.

Even more preferably, -L$^2$- and -L$^{2'}$- are a $C_{1-20}$ alkyl chain, which is optionally interrupted by one or more groups independently selected from —O—, -T- and —C(O)N(R$^{1aa}$)—; and which $C_{1-20}$ alkyl chain is optionally substituted with one or more groups independently selected from —OH, -T and —C(O)N(R$^{y6}$R$^{y6a}$); wherein R$^{y6}$, R$^{y6a}$ are independently selected from the group consisting of H and $C_{1-4}$ alkyl and wherein T is selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8-to 30-membered carbopolycyclyl, and 8- to 30-membered heteropolycyclyl.

Preferably, -L$^2$- and -L$^{2'}$- have a molecular weight in the range of from 14 g/mol to 750 g/mol.

Preferably, -L$^2$- comprises a moiety selected from

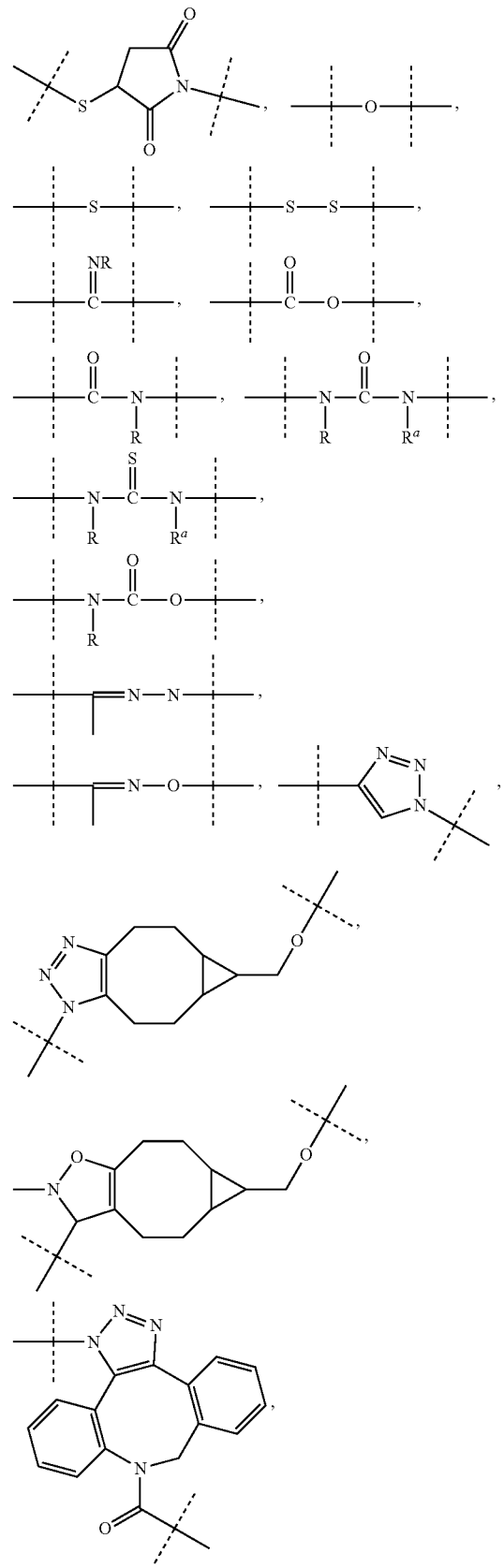

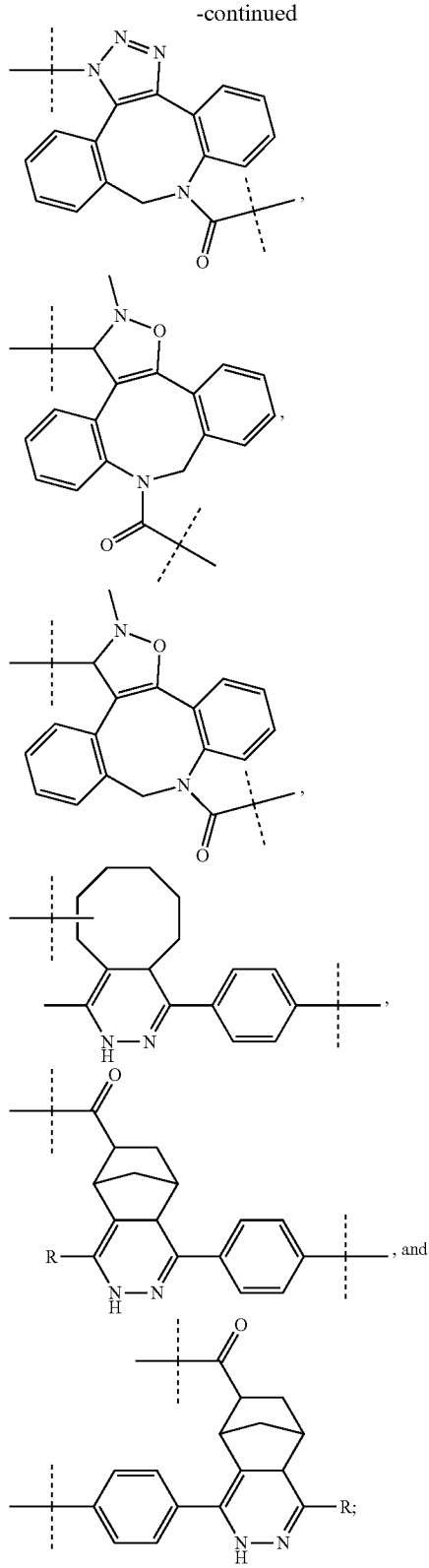

wherein
dashed lines indicate attachment to the rest of -L²-; and
R and Rᵃ are independently of each other selected from the group consisting of —H, methyl, ethyl, propyl, butyl, pentyl and hexyl.

-L²-Z and -L²-Y can be attached to -L¹- of formula (I) or (I') by replacing any —H present. Preferably, one to five of the hydrogen given by $R^1$, $R^{1a}$, $R^2$, $R^{2a}$, $R^3$, $R^{3a}$, $R^4$, $R^5$, $R^6$, $R^{6a}$, $R^7$ and $R^{7a}$ are replaced by -L²-Z and/or -L²'-Y. More preferably, only one hydrogen of -L¹- of formula (I) or (I') is replaced by -L²-Z or -L²'-Y. In other words, it is preferred that -L¹- of formula (I) is substituted with one moiety -L²-Z and that -L¹- of formula (I') is substituted with one moiety -L²-Z or -L²'-Y.

In a preferred embodiment $R^4$ of formula (I) is substituted with -L²-Z, i.e. any one of the —H present in $R^4$ is replaced by -L²-Z.

In a preferred embodiment $R^4$ of formula (I') is substituted with -L²-Z or -L²'-Y, i.e. any one of the —H present in $R^4$ is replaced by -L²-Z or -L²'-Y.

In another preferred embodiment $R^5$ of formula (I) is substituted with -L²-Z, i.e. any one of the —H present in $R^5$ is replaced by -L²-Z.

In another preferred embodiment $R^5$ of formula (I') is substituted with -L²-Z or -L²'-Y, i.e. any one of the —H present in $R^5$ is replaced by -L²-Z or -L²'-Y.

Another aspect of the present invention is a method of synthesis of a prodrug or pharmaceutical salt thereof of the present invention.

Preferably, the method of synthesis of a prodrug of the present invention comprises the steps of
(a) Providing a reagent comprising a moiety Y-L²'-L¹-Q, wherein
—Y is a functional group,
-L²'- is a chemical bond or a spacer,
-L¹- is of formula (I') which optionally comprises functional groups protected with protecting groups,
-Q is —OH or a leaving group;
(b) Reacting -Q of the reagent of step (a) with a primary or secondary amine or hydroxyl functional group of a drug D-H by forming an amide or ester linkage between -L¹- and -D, respectively; wherein the drug optionally comprises further functional groups which may optionally be protected with protecting groups;
(c) Reacting a reagent comprising Z having at least one functional group —Y' with —Y of the intermediate of step (b) by forming a linkage between Z and -L²'-, resulting in Z being conjugated to at least one moiety -L²-L¹-D;
(d) Optionally removing the protecting groups present.

It is understood that one or more functional groups —Y' of Z react with a functional group —Y, i.e. that one or more reagents of step (a) are conjugated to Z.

Preferred embodiments for —Y, -L¹-, -L²'-, -L²-, -D and -Q are as described above.

In an equally preferred embodiment the method of synthesis of a prodrug of the present invention comprises the steps of
(a) Providing a reagent comprising a moiety Y-L²'-L¹-Q, wherein
—Y is a functional group,
-L²'- is a chemical bond or a spacer,
-L¹- is of formula (I') which optionally comprises functional groups protected with protecting groups,
-Q is —OH or a leaving group;
(b) Reacting a reagent comprising Z having at least one functional group —Y' with —Y of the reagent of step (a) by forming a linkage between Z and -L²'-, resulting in Z being conjugated to at least one moiety -L²-L¹-Q;
(c) Reacting -Q of the intermediate of step (b) with a primary or secondary amine or hydroxyl functional group of a drug D-H by forming an amide or ester linkage between $L^1$ and D, respectively; wherein the drug optionally comprises further functional groups which may optionally be protected with protecting groups;

(d) Optionally removing the protecting groups present.

It is understood that one or more functional groups —Y' of Z react with a functional group —Y, i.e. that one or more reagents of step (a) are conjugated to Z.

Preferred embodiments for —Y, -$L^1$-, -$L^{2'}$-, -$L^2$-, -D and -Q are as described above.

Preferred embodiments of —Y' correspond to the preferred embodiments of —Y as described above.

The person skilled in the art is aware that not every Y can be used in combination with any Y' and will have no problem identifying suitable pairs. Preferred pairs Y/Y' are the following:
- Y is maleimide, Y' is selected from thiol, amine and selenide;
- Y' is maleimide, Y is selected from thiol, amine and selenide;
- Y is selected from formulas (z'vi), (z'iii) and (z'iv), Y' is of formula (z'x);
- Y' is selected from formulas (z'vi), (z'iii) and (z'iv), Y is of formula (z'x);
- Y is selected from formulas (z'ii), (z'v), (z'vii) and a terminal alkynyl, Y' is azide;
- Y' is selected from formulas (z'ii), (z'v), (z'vii) and a terminal alkynyl, Y is azide;
- Y is of formula (z'xx), Y' is azide;
- Y' is of formula (z'xx), Y is azide;
- Y is of formula (z'viii), Y' is of formula (z'i);
- Y' is of formula (z'viii), Y is of formula (z'i);
- Y is of formula (z'ix), Y' is of formula (z'iv);

It is understood that the above listed pairs Y/Y' are preferred examples and do not represent a comprehensive list of all possible pairs.

Another aspect of the present invention is a pharmaceutical composition comprising the prodrug of the present invention and one or more excipients.

A further aspect of the present invention is the prodrug of the present invention or the pharmaceutical composition comprising the prodrug of the present invention for use as a medicament.

Materials and Methods

Materials:

Compound PEG 12 (example 7) was synthesized following the procedure described in patent WO29095479A2, example 1.

H$_2$N-PEG(12)-COOH (example 27, CAS 1415408-69-3) was purchased from Biomatrik Inc., Jiaxing, China.

Human Insulin (rDNA Origin) was acquired from Biocon, Bangalore, India.

HFIP was obtained from ABCR GmbH & Co. KG, Karlsruhe, Germany.

N-Boc-N-methylethylenediamine and Bis(pentafluorophenyl) carbonate were purchased from Iris Biotech GmbH, Marktredwitz, Germany.

PyBOP, HOSu and N-cyclohexylcarbodiimide-N-methyl polystyrene were purchased from Novabiochem, Merck KGaA, Darmstadt, Germany.

N-(6-Bromohexyl)phthalimide was obtained from Alfa Aesar, Ward Hill, USA.

m-dPEG 37-NHS ester (example 23) was obtained from Celares GmbH, Berlin, Germany.

TFA, Et$_2$O, MTBE, MeCN, boric acid and MgSO$_4$ were purchased from Carl Roth GmbH & Co. KG, Karlsruhe, Germany.

Lipase B from *Candida antarctica* was purchased from Hampton Research, Aliso Viejo, USA.

All other chemicals were obtained from Sigma-Aldrich Chemie GmbH, Taufkirchen, Germany.

Methods:

Reactions were performed with dry solvents (CH$_2$Cl$_2$, MeCN, DMF, MeOH) stored over molecular sieves purchased from Sigma-Aldrich Chemie GmbH, Taufkirchen, Germany or in absolute ethanol purchased from VWR International GmbH, Darmstadt, Germany. Generally, reactions were stirred at room temperature and monitored by LCMS or TLC.

Preparative HPLC was done on a reverse phase column (XBridge BEH300 C18 OBD Prep 10 μm 30×150 mm) connected to a Waters 600 or 2535 HPLC system and Waters 2489 absorbance detector. Gradients of solution A (0.1% TFA in H$_2$O) and solution B (0.1% TFA in acetonitrile) were used. HPLC fractions containing product were combined and lyophilized.

Flash chromatography purifications were performed on an Isolera One system from Biotage AB, Sweden, using Biotage KP-Sil silica cartridges and n-heptane, and ethyl acetate as eluents. Products were detected at 254 nm.

Analytical UPLC-MS was performed on a Waters Acquity UPLC with an Acquity PDA detector coupled to a Waters Micromass ZQ equipped with a Waters ACQUITY UPLC BEH300 C18 reverse phase column (2.1×50 mm, 300 Å, 1.7 μm, flow: 0.25 ml/min; solvent A: H$_2$O+0.05% TFA, solvent B: acetonitrile+0.04% TFA).

EXAMPLES

Example 1

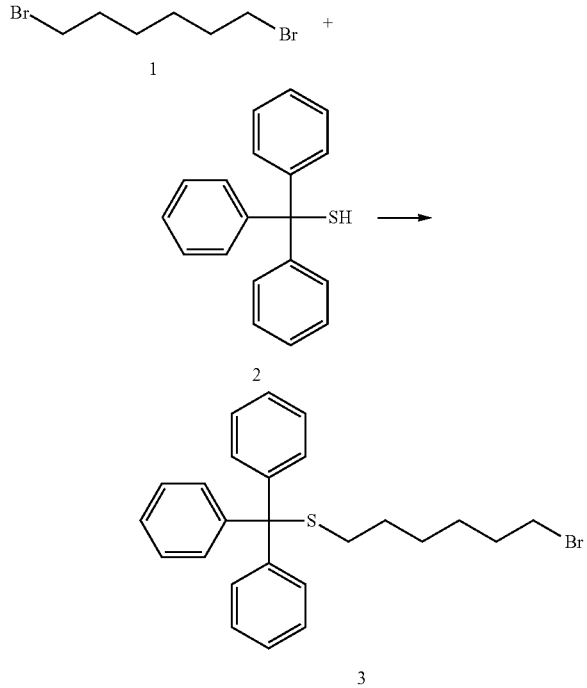

Triphenylmethanethiol (2) (5.00 g; 18.09 mmol; 1.00 eq.) was stirred in ethanol (36.25 ml), yielding a slightly turbid, yellow solution. A solution of sodium hydroxide, NaOH (795.90 mg; 19.90 mmol; 1.10 eq.) in water (5.45 ml) was added. After 15 min of stirring at room temperature 1,6-dibromohexane (1) (4.17 ml; 27.14 mmol; 1.50 eq.) in ethanol (7.25 ml) was added dropwise. A slightly yellowish solid precipitated from the solution. The reaction mixture was stirred at room temperature overnight.

The ethanol was evaporated and the residue was taken up in CH$_2$Cl$_2$ (36 ml). The solution was washed with water (15 ml) and brine (15 ml). The organic layer was dried over MgSO$_4$, filtered and the solvent was evaporated. The residue was dried under high vacuum for 2 hours.

The yellow, oily residue was dissolved in CH$_2$Cl$_2$ (7 ml) and hexane (18 ml) was added. A yellowish precipitate was observed after the solution was kept at −20° C. for 40 h. The supernatant was decanted and the residue was washed with hexane and dried to yield a first product batch. The mother liquor and the hexane from the washing step were combined, evaporated and dried for 2 h at high vacuum. The residue was taken up in dichloromethane (2 ml) and hexane (15 ml). The solution was kept at −20° C. over the weekend. The formed yellowish precipitate was isolated and dried at high vacuum for 2 hours to yield a second batch. The batches were similar in purity and therefore combined.

Yield: 4.57 g, 57%

Example 2

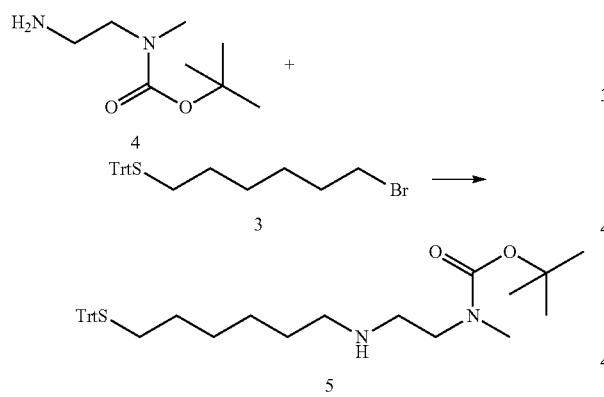

[6-bromohexylsulfanyl(diphenyl)methyl]benzene (3) (500.00 mg; 1.14 mmol; 1.00 eq.) was dissolved in anhydrous acetonitrile (10.00 ml) and N-Boc-N-methylethylenediamine (4) (1.02 ml; 5.69 mmol; 5.00 eq.) was added.

The reaction mixture was stirred at room temperature overnight. A white precipitate was observed. An UPLC chromatogram showed full conversion to the product. The crude material was purified by preparative HPLC and the product containing fractions were lyophilized.

Et$_2$O (20 ml) and sat. NaHCO$_3$ (20 ml) were added to the isolated TFA-salt (227 mg). The mixture was stirred under evolution of gas until all solids were dissolved. The phases were separated and the aqueous phase was extracted two additional times with Et$_2$O (20 ml each). The organic solutions were combined and dried over MgSO$_4$, filtered and concentrated.

Yield: 185.00 mg; 31%

MS: m/z=533.85 [M+H]$^+$ (calculated: 533.32)

Example 3

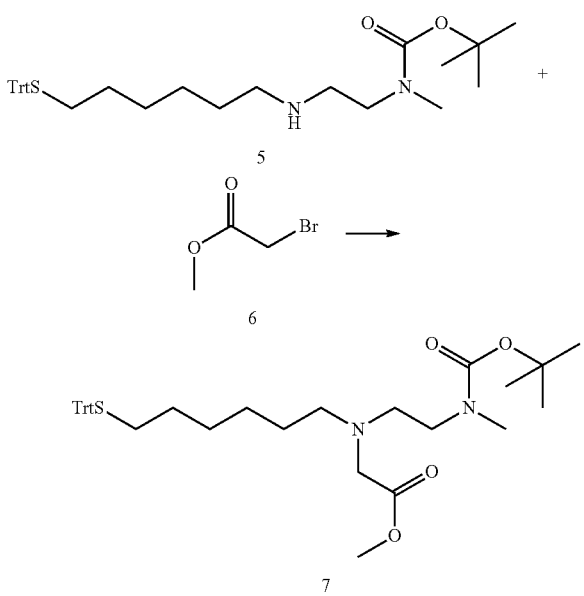

tert-butyl N-methyl-N-[2-(6-tritylsulfanylhexylamino)ethyl]carbamate (5) (185.00 mg; 0.35 mmol; 1.00 eq.) was dissolved in anhydrous acetonitrile (3.70 ml). Methyl bromoacetate (6) (65.74 µl; 0.69 mmol; 2.00 eq.) and N,N-diisopropylethylamine (604.82 µl; 3.47 mmol; 10.00 eq.) were added.

After an UPLC chromatogram showed full conversion to the product, the reaction mixture was filtered and the filter cake was washed with acetonitrile (2 ml). The solvent was evaporated and the residue was dissolved in 2 ml of dichloromethane. The crude material was purified by column chromatography.

Yield: 97.00 mg; 46%

MS: m/z=605.99 [M+H]$^+$ (calculated: 605.34)

Example 4

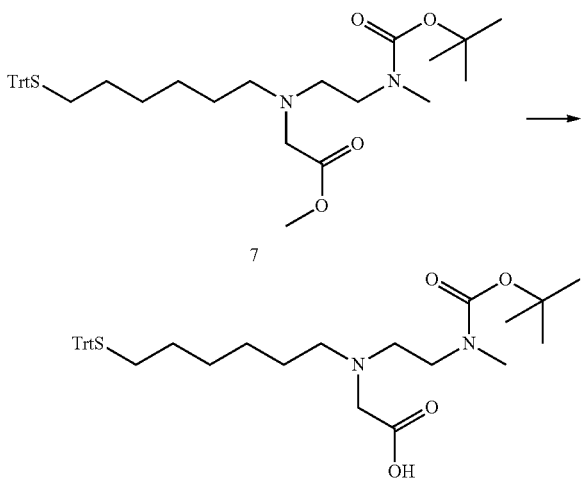

Methyl 2-[2-[tert-butoxycarbonyl(methyl)amino]ethyl-(6-tritylsulfanylhexyl)amino]acetate (7) (97.00 mg; 0.16 mmol; 1.00 eq.) was dissolved in methanol (7.62 ml). A 1 N solution of sodium hydroxide in water (5.08 ml; 1.00 mol/l; 5.08 mmol; 31.67 eq.) and water (4 ml) were added and the reaction mixture was stirred until full conversion was observed by UPLC-MS.

The reaction was quenched by the addition of 1 N hydrochloric acid (5.08 ml; 1.00 mol/l; 5.08 mol; 31.67 eq.). The reaction mixture was stored at 4° C. overnight whereupon an emulsion was formed. The supernatant was carefully removed and the second phase was diluted with water, frozen and lyophilized. The residue was triturated with 3 ml of dichloromethane. The solution was filtered and the solvent evaporated. The residue was dried under high vacuum for 1 hour.

Yield: 94.00 mg; 99%
MS: m/z=591.84 [M+H]$^+$ (calculated: 591.33)

Example 5

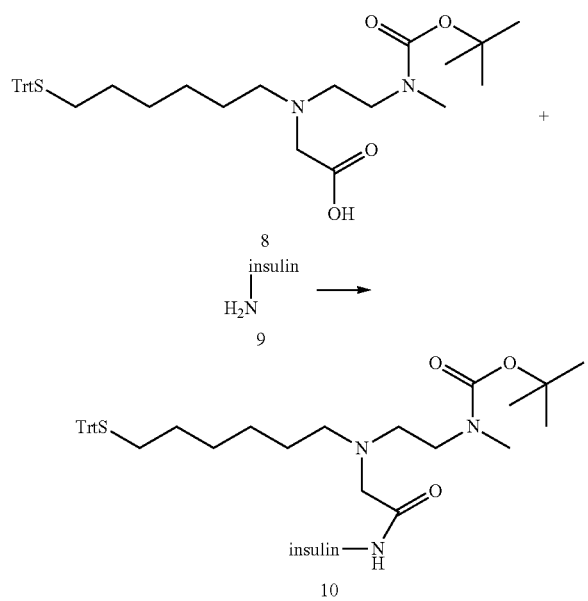

2-[2-[Boc(methyl)amino]ethyl-(6-tritylsulfanylhexyl) amino]acetic acid (8) (21.50 mg; 0.04 mmol; 1.20 eq.) and TSTU (12.78 mg; 0.04 mmol; 1.40 eq.) were dissolved in DMF (1 ml) and DIPEA (11.76 mg; 0.09 mmol; 3.00 eq.) was added. The reaction mixture was stirred for 15 min at room temperature.

Insulin (9) (176.13 mg; 0.03 mmol; 1.00 eq.) was dissolved in reaction buffer (2.5 ml, 4:6$_{(v/v)}$ borate buffer (0.375 M sodium borate, pH 8.50): DMF). The activated linker solution was added and the reaction mixture was stirred at room temperature for 45 min. A mixture of unmodified insulin, two different mono-adducts and a bis-adduct was observed by UPLC-MS. The two mono-adducts were separated by preparative HPLC. The fractions containing the major mono-adduct isomer were pooled and lyophilized.

Yield: 39.60 mg; 17%
MS: m/z=1597.22 [M+4H]$^{4+}$ (calculated: 1594.99)

Example 6

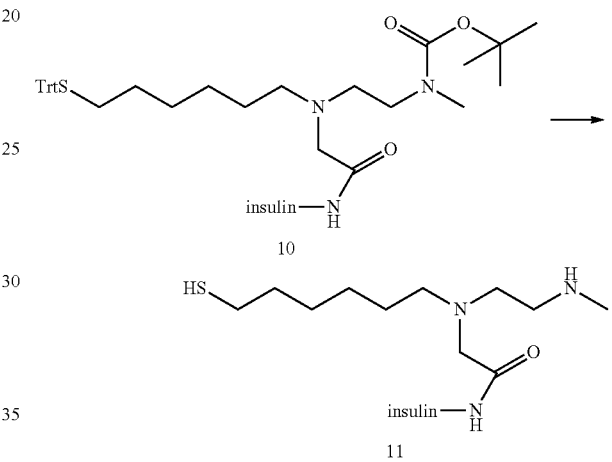

The protected insulin-linker conjugate 10 (39.60 mg; 0.01 mmol; 1.00 eq.) was dissolved in HFIP (2 ml) to yield a yellow solution. TFA (200 µl) and TES (50 µl) were added (solution turns colorless) and the solution was stirred at room temperature for 3 h. Full conversion was observed and the crude reaction mixture was concentrated. The resulting crude product was used without further purification in the next step.

MS: m/z=1511.28 [M+4H]$^{4+}$ (calculated: 1509.45)

Example 7

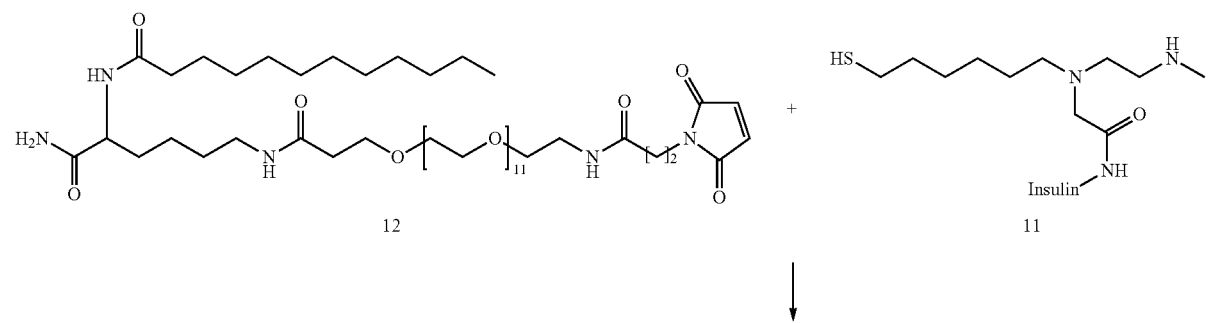

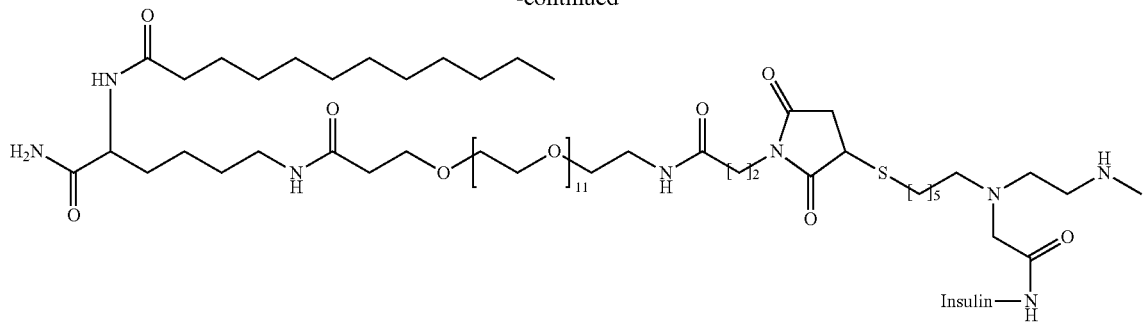

13

A stock solution of 20 mg/ml maleimide functionalized PEG 12 in 1:1 MeCN/H$_2$O (18.5 μmol/ml) was prepared.

The deprotected insulin-linker conjugate 11 (ca. 5.7 μmol, 1.00 eq., crude) was dissolved in 2.5 ml of 1:1 MeCN/H$_2$O and 616 μl of the PEG stock solution (2 eq, 11.4 μmol) were added. The reaction was started by the addition of buffer (600 μl, 0.5 M phosphate, pH 7.5). The pH was checked with pH paper (ca. pH 7.5) and stirred for 15 min. The reaction was quenched by the addition of 10% AcOH$_{aq}$ (200 μl). The pH was checked with pH paper (ca. pH 4.0).

The resulting solution was purified by preparative HPLC. The product containing fractions were pooled and lyophilized.

Yield: 35 mg; 79% over 2 steps
MS: m/z=1780.07 [M+4H]$^{4+}$ (calculated: 1780.81)

Example 8

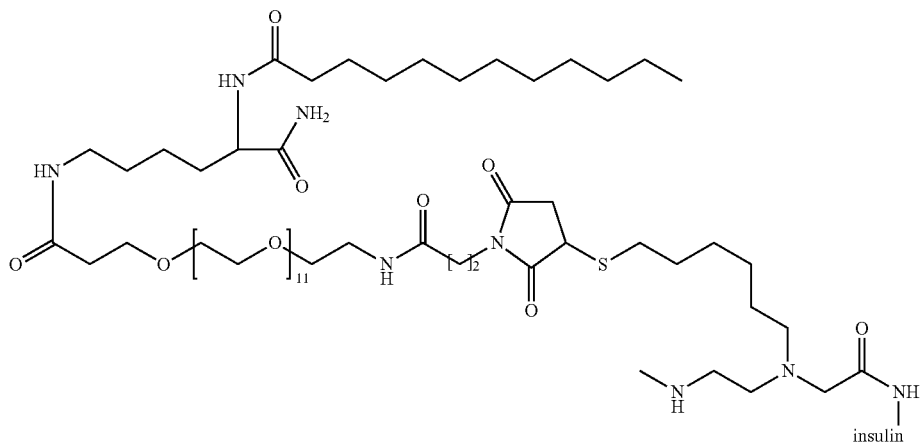

13

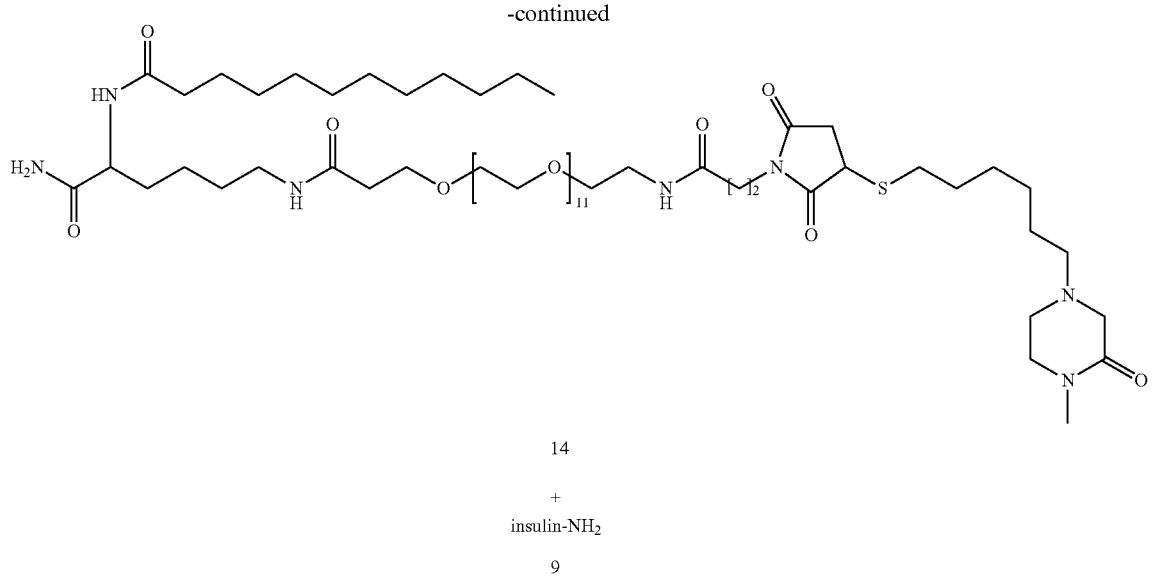

14

+ insulin-NH$_2$

9

The hydrolysis kinetics of PEGylated linker-insulin conjugate 13 were studied in buffer at 37° C. Therefore, the starting material was dissolved in buffer (60 mM phosphate, 3 mM EDTA, pH 7.4) and mixed for 15 min. The resulting solution was incubated in a water bath at 37° C. At given points in time samples were withdrawn, quenched and analyzed by UPLC-MS.

Insulin was released with a half-life of 28 d.

Example 9

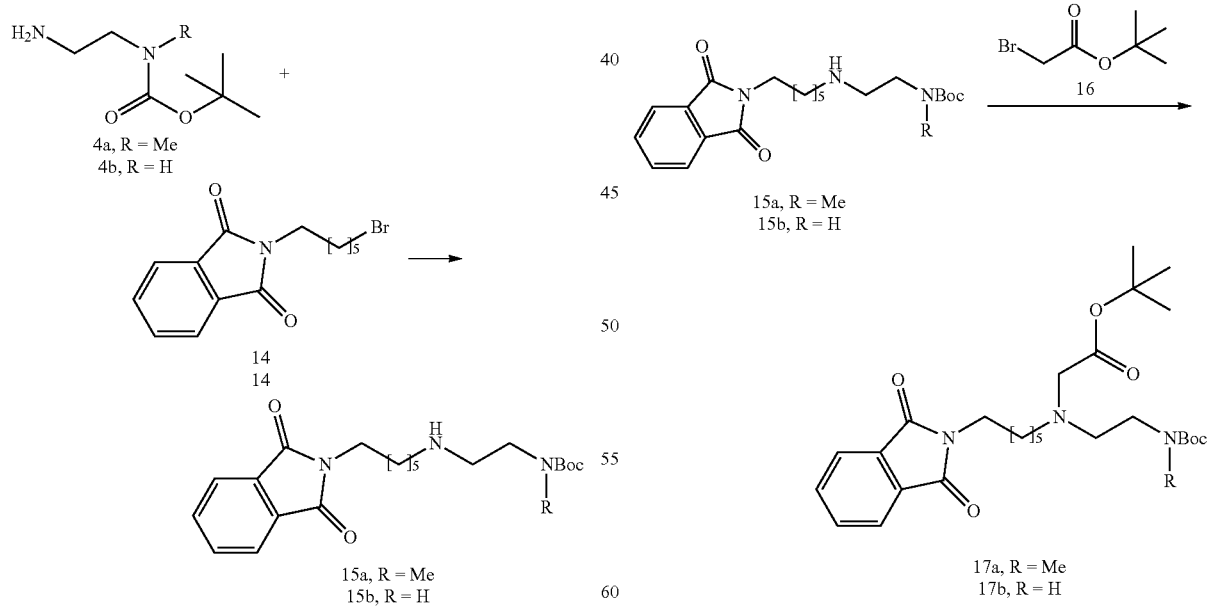

N-Boc-N-methylethylenediamine (4a, 576.13 μl; 3.22 mmol; 5.00 eq.) and N-(6-bromohexyl)-phthalimide (14, 200.00 mg; 0.64 mmol; 1.00 eq.) were dissolved in acetonitrile and stirred at room temperature overnight. The reaction mixture was diluted with water and purified by preparative HPLC. Product containing fractions were pooled and lyophilized to yield amine 15a.

Yield: 139 mg; 42%

MS: m/z=404.20 [M+H]$^+$

Phthalimide 15b was synthesized accordingly, starting from amine 4b.

Example 10

Amine 15a (139.00 mg; 0.27 mmol; 1.00 eq.) was dissolved in acetonitrile (2.50 ml) and DIPEA (93.56 μl; 0.54 mmol; 2.00 eq.) was added. Bromide 16 (51.55 μl; 0.35 mmol; 1.30 eq.) was added and the reaction mixture was stirred at room temperature for 2 h.

The solvent was evaporated and the residue was dissolved in 1 ml of heptane/ethyl acetate, filtered and purified by flash chromatography to yield 17a.

Yield: 116 mg; 83%

MS: m/z=518.33 [M+H]$^+$

Amine 17b was synthesized accordingly, starting from amine 15b.

Example 11

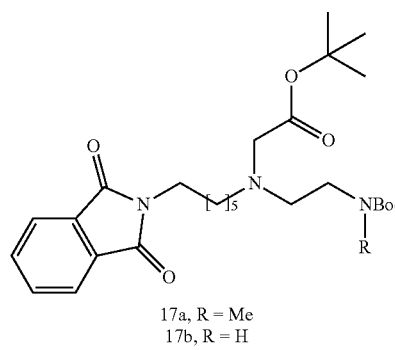

17a, R = Me
17b, R = H

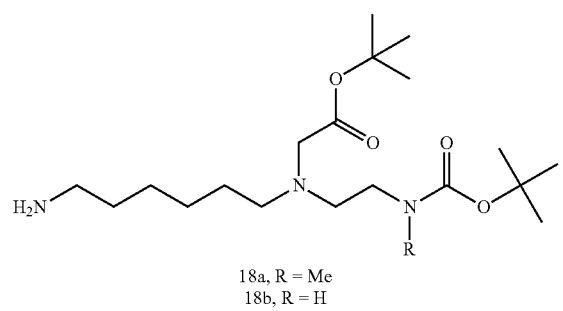

18a, R = Me
18b, R = H

Hydrazine hydrate (33.00 μl; 0.68 mmol; 3.04 eq.) was added to a solution of phthalimide 17a (115.70 mg; 0.22 mmol; 1.00 eq.) in ethanol (2.00 ml). The reaction mixture was heated under reflux (oil bath 93° C.) for 2 h. A white precipitate formed.

The reaction mixture was cooled to room temperature. The precipitate was filtered off and washed with cold EtOH (2×1 ml). The filtrate was concentrated to yield a white residue (63 mg). It was redissolved in chloroform (1.3 ml) and stirred for 1 h. The precipitate was filtered off through a small bed of Celite, washed with chloroform (0.5 ml) and the organic phase was concentrated and dried under vacuum to yield amine 18a.

Yield: 63 mg; 72%

MS: m/z=388.31 [M+H]$^+$

Amine 18b was synthesized accordingly, starting from amine 17b.

Example 12

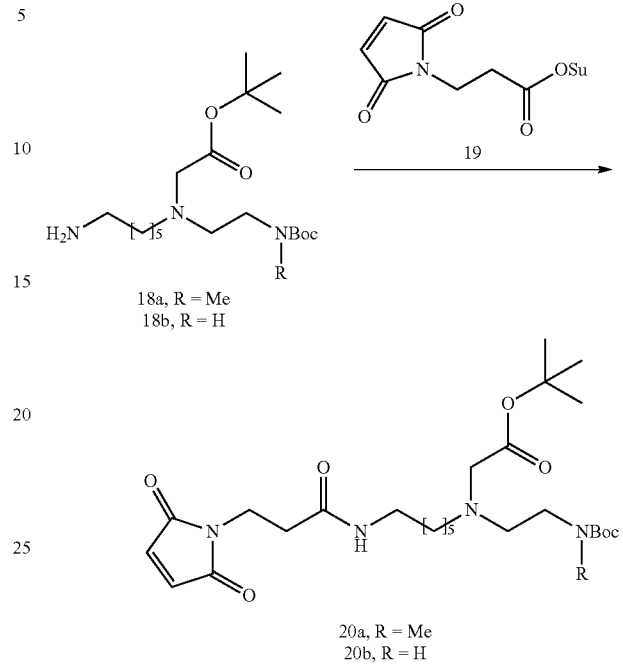

18a, R = Me
18b, R = H

20a, R = Me
20b, R = H

Amine 18a (62.50 mg; 0.16 mmol; 1.00 eq.) and DIPEA (84.27 μl; 0.48 mmol; 3.00 eq.) were dissolved in acetonitrile (1.00 ml). NHS ester 19 (51.52 mg; 0.19 mmol; 1.20 eq.) was added and the reaction mixture was stirred at room temperature for 15 min. Analysis by LCMS showed full conversion of the starting material. The reaction mixture was stored at −20° C. overnight.

The reaction was brought to room temperature and quenched by the addition of TFA (36 μl). A drop of water was added to dissolve the DIPEA salts. The crude mixture was purified by preparative HPLC. Product containing fractions were pooled and lyophilized to yield maleimide 20a.

Yield: 84 mg; 80%

MS: m/z=539.31 [M+H]$^+$

Maleimide 20b was synthesized accordingly, starting from amine 18b.

Example 13

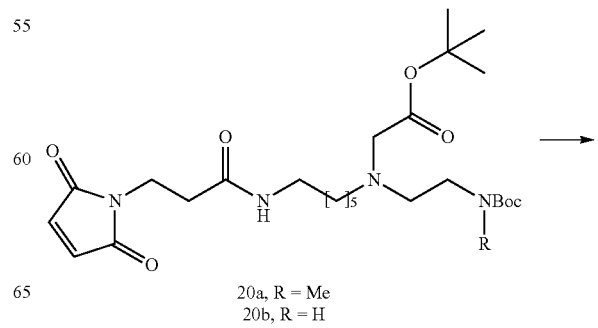

20a, R = Me
20b, R = H

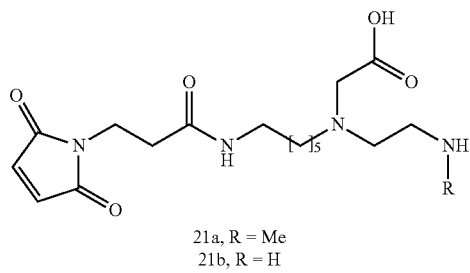

21a, R = Me
21b, R = H

Maleimide 20a (83.90 mg; 0.13 mmol; 1.00 eq.) was dissolved in dichloromethane (1.00 ml) and TFA (1.00 ml; 13.07 mmol; 101.66 eq.) was added. The reaction mixture was stirred at room temperature for 3.5 h. The volatiles were removed in a stream of nitrogen and the residue was dried carefully under vacuum.

Product 21a was used immediately (without further purification) in the next step.

Yield: 78 mg; 100%

MS: m/z=383.21 [M+H]$^+$

Product 21b was synthesized accordingly, starting from amine 20b.

Example 14

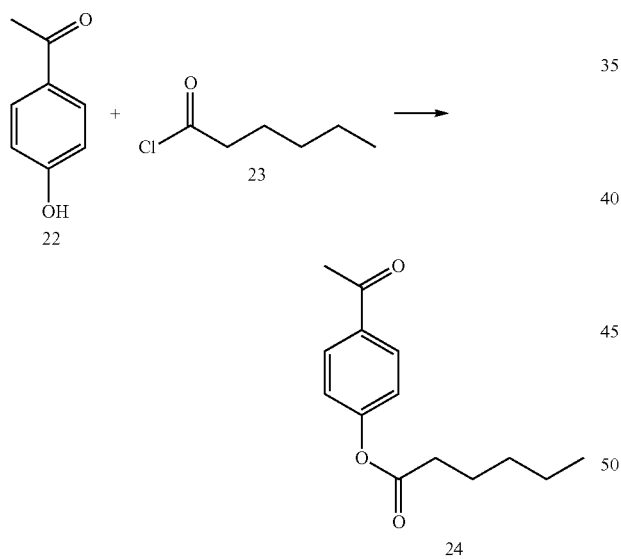

p-Hydroxyacetophenone (22, 680.74 mg; 5.00 mmol; 1.00 eq.) was dissolved in THF (27 ml). DIPEA (1.75 ml; 10.00 mmol; 2.00 eq.) and 2 min later hexanoyl chloride (23, 908.54 µl; 6.50 mmol; 1.30 eq.) were added dropwise under stirring. After 15 min the reaction mixture was analyzed by LCMS and showed complete conversion to the product.

The solution was filtered and the filtrate was diluted with diethyl ether (100 ml) and washed once with saturated NaHCO$_3$-solution (100 ml). The aqueous phase was extracted with diethyl ether (50 ml) and the combined organic phases were washed twice with 100 ml of a 0.1 M HCl-solution. The organic phase was dried over Na$_2$SO$_4$, filtered and the solvents were removed under reduced pressure.

Yield: 1.2 g; 100%

MS: m/z=235.03 [M+H]$^+$

Example 15

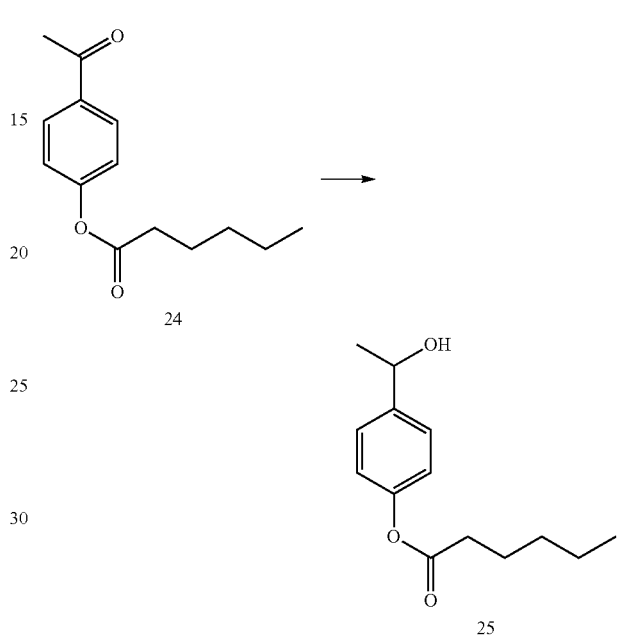

Ketone 24 (1.29 g; 5.00 mmol; 1.00 eq.) was dissolved in acetonitrile (16 ml). Sodium borohydride (378.32 mg; 10.00 mmol; 2.00 eq.) was added in portions. At the end ethanol (820.01 µl) was added. The reaction mixture was stirred overnight at room temperature. An LCMS chromatogram after 19 hours showed full conversion to the product.

The reaction mixture was diluted with 150 ml of diethyl ether. The organic layer was washed twice with 100 ml of water. The organic layer was dried over MgSO$_4$, filtered and concentrated under reduced pressure.

Yield: 951 mg; 80%

MS: m/z=237.02 [M+H]$^+$

Example 16

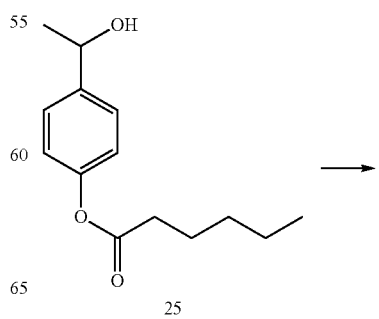

-continued

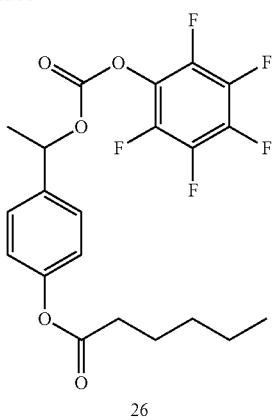

26

Benzyl alcohol 25 (951.00 mg; 4.02 mmol; 1.00 eq.) was dissolved in acetonitrile (20 ml) and cooled to 0° C. in an ice bath. Bis(pentafluorophenyl) carbonate (3.97 g; 10.06 mmol; 2.50 eq.), DMAP (122.91 mg; 1.01 mmol; 0.25 eq.) and DIPEA (3.50 ml; 20.12 mmol; 5.00 eq.) were added. The reaction mixture was stirred at room temperature for 1 hour.

An LCMS chromatogram showed complete conversion of the starting material.

The reaction mixture was diluted with 75 ml of diethyl ether. The organic layer was washed twice with 80 ml of water. The organic layer was dried over MgSO₄, filtered and concentrated under reduced pressure. The crude material was purified by flash chromatography.

Yield: 1.13 g; 63%

Example 17

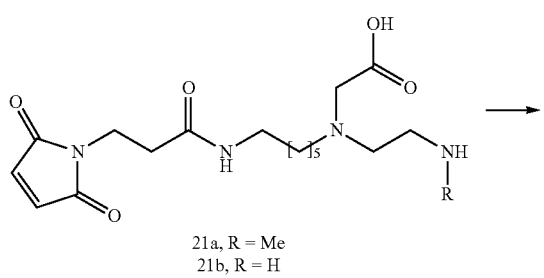

21a, R = Me
21b, R = H

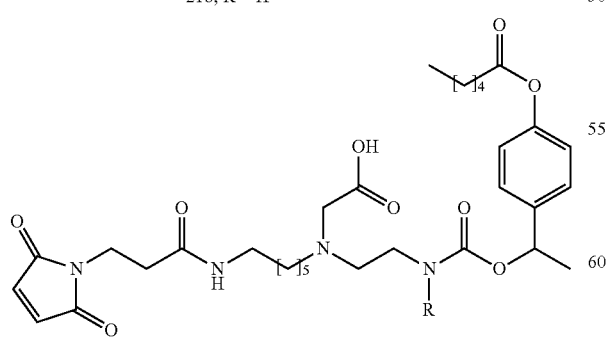

27a, R = Me
27b, R = H

Building block 21a (78.50 mg; 0.13 mmol; 1.00 eq.) was dissolved in acetonitrile (1.00 ml) and DIPEA (134.38 µl; 0.77 mmol; 6.00 eq.) was added. PFP-carbonate 26 (68.87 mg; 0.15 mmol; 1.20 eq.) and DMAP (3.14 mg; 0.03 mmol; 0.20 eq.) were added and the reaction mixture was stirred at room temperature. The reaction was quenched with TFA (77 µl) after 40 min and purified by preparative HPLC to yield carbamate 27a.

Yield: 56 mg; 59%

MS: m/z=645.42 $[M+H]^+$

Product 27b was synthesized accordingly, starting from amine 21b.

Example 18

27a, R = Me
27b, R = H

28a, R = Me
28b, R = H

Carboxylic acid 27a (10.00 mg; 0.01 mmol; 1.10 eq.), DIPEA (5.40 µl; 0.03 mmol; 2.59 eq.), HOSu (1.38 mg; 0.01 mmol; 1.00 eq.) and N-cyclohexylcarbodiimide-N-methyl polystyrene (18.92 mg; 0.04 mmol; 3.00 eq.) were shaken with anhydrous dichloromethane (0.40 ml) and 40 µl of THF in a syringe reactor overnight.

The resin was filtered off and washed with dry DCM (2×0.5 ml). The solvent was evaporated in a stream of argon and dried under vacuum for 2 h to yield 14.6 mg of product 28a as oil. The residue was dissolved in dry DMSO (600 µl) and filtered through a syringe filter (22 µm) to yield a 20 mM solution. LCMS analysis after derivatization of a sample with Boc-ethylenediamine in DMSO showed a ratio of 6:94 carboxylic acid/NHS ester. The solution was stored at −20° C.

Product 28b was synthesized accordingly, starting from amine 27b.

Example 19

27b + H₂N—insulin →

9

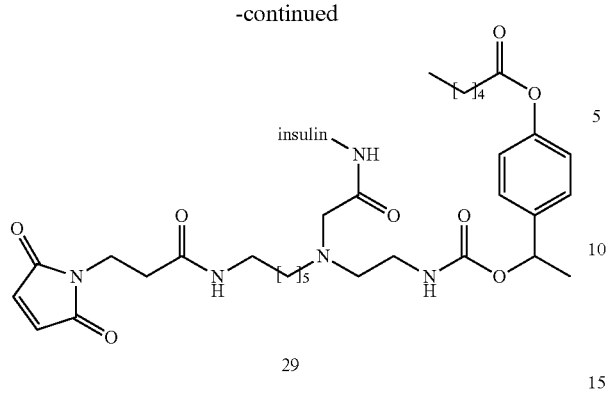

29

400 µL of an insulin solution in DMSO (50 mg/mL; 3.44 µmol; 1.00 eq) were mixed with 400 µL DMSO and 400 µL borate buffer (0.375 M boric acid, adjusted to pH 8.1 with tetrabutylammoniumhydroxide). A solution of 27b in DMSO was added (68.8 µL; 0.05 mol/L; 3.44 µmol; 1.00 eq). The mixture was agitated for 15 min at ambient temperature and diluted under cooling on an ice bath with 2 mL 10 vol % AcOH and 6 mL water. The solution was purified by preparative HPLC. The pure fractions were combined, frozen and lyophilized to yield protected insulin-linker conjugate 29.

Yield: 0.8 mg; 4%
MS: m/z=1605.01 [M+4H]$^{4+}$

Example 20

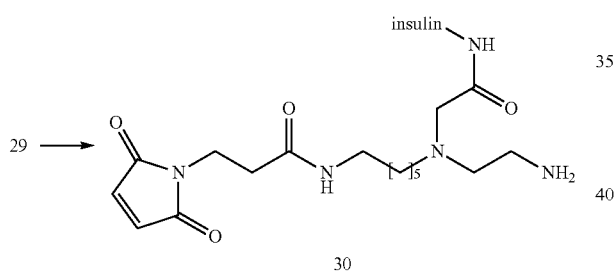

30

0.8 mg (0.125 µmol, 1.00 eq) of protected insulin-linker conjugate 29 were dissolved in 0.5 mL 20 mM succinate buffer, pH 5.0. Lipase B was added (0.1 mg) and the suspension was incubated at ambient temperature for 1 h. The solution was filtered through a 0.22 µm PVDF filter, diluted with 0.5 mL water and purified by preparative HPLC. The pure fractions were combined, frozen and lyophilized to yield deprotected insulin-linker conjugate 30.

Yield: 0.5 mg; 65%
MS: m/z=1231.79 [M+5H]$^{5+}$

Example 21

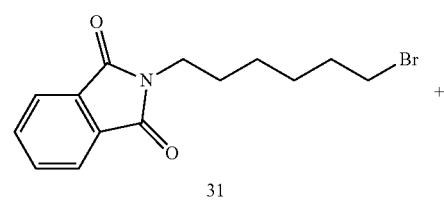

31

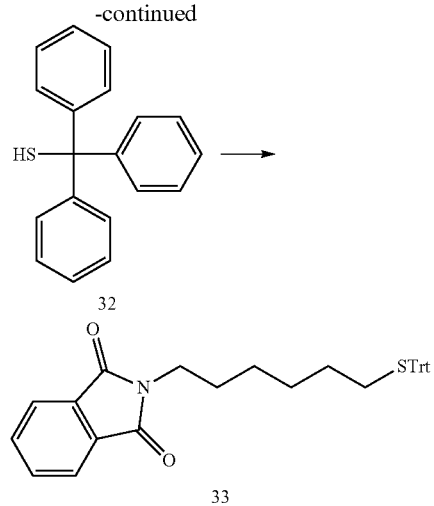

11.9 g tritylsulfide 32 (43.1 mmol, 1.02 eq) were dissolved in 50 mL DMSO. 7.30 mL DBU (48.8 mmol; 1.14 eq) and 13.3 g phthalimide 31 followed by 15 mL DMSO were added. The mixture was stirred for 12 min at ambient temperature. 700 mL ethyl acetate and 200 mL 0.1 N HCl were added. The mixture was stirred until both solvent layers were clear. The layers were separated. The aqueous phase was extracted with ethyl acetate (3×, 50 mL each). The organic solutions were combined, washed with 80 mL sat. NaHCO$_3$ and 80 mL brine, dried over Na$_2$SO$_4$ and filtered. The solvent was removed in vacuo. The residue was recrystallized from 240 mL ethanol under heating. The suspension was stored for 1 h at −18° C. The trityl protected product 33 was filtered off, washed 2× with ethanol and dried under high vacuum.

Yield: 19.6 g; 90%
MS: m/z=528.07 [M+Na]$^+$

Example 22

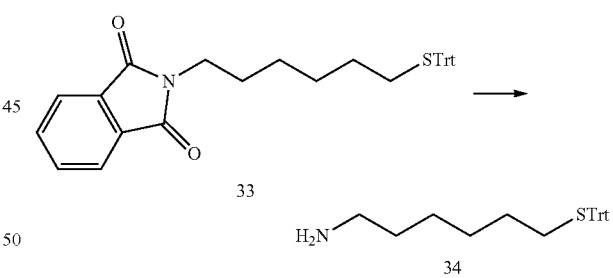

19.5 g phthalimide 33 (38.6 mmol; 1.00 eq) was suspended in 300 mL abs. ethanol and 5.74 mL hydrazine hydrate (116.8 mmol; 3.03 eq) were added. The mixture was heated under reflux for 2 h and subsequently cooled to −18° C., the precipitate was filtered off and washed 2× with cold ethanol. The filtrate was concentrated in vacuo and stored for 2 days at −18° C. 234 mL CHCl$_3$ was added, stirred for 2 h at ambient temperature, and stored at −18° C. for 2 days. The precipitate was filtered off and washed 2× with cold CHCl$_3$. The filtrate was washed with 250 mL H$_2$O, 250 mL brine, dried over anhydrous MgSO$_4$, and filtered. The solvent was removed in vacuo. Amine 34 was dried under high vacuum.

Yield: 13.1 g; 91%
MS: m/z=376.26 [M+H]$^+$

Example 23

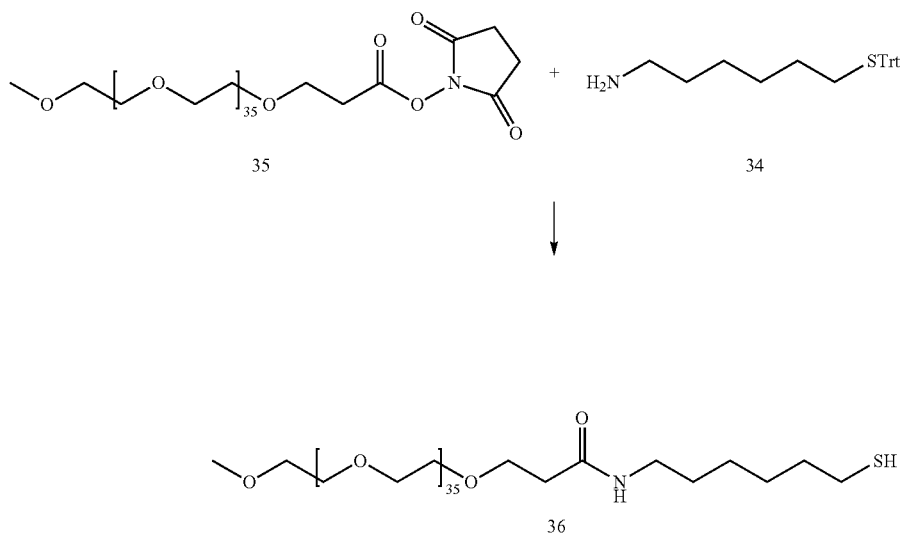

114 mg m-dPEG 37-NHS ester 35 (0.06 mmol; 1.00 eq) were dissolved in 1.00 mL anhydrous DCM. 35.9 mg 6-tritylmercaptohexylamine 34 (0.10 mmol; 1.50 eq) and 22.2 µL N,N-diisopropylethylamine (0.13 mmol; 2.00 eq) were added. The mixture was stirred for 1 h at ambient temperature. The solvent was evaporated in a stream of nitrogen. The residue was dissolved in a mixture of 2.00 ml 9:1 MeCN/H$_2$O+0.1% TFA, 1.00 ml H$_2$O+0.05% TFA and 0.80 mL MeCN and purified by preparative HPLC (eluents: MeCN+0.1% TFA, H$_2$O+0.1% TFA). MeCN was removed from the product fractions in vacuo. The aqueous layer was extracted 6 times with DCM. The combined organic fractions were dried over anhydrous MgSO$_4$ and concentrated in vacuo. 0.2 mL TES and 0.75 mL TFA were added. The mixture was stirred for 1 h at ambient temperature. 500 mL diethyl ether containing 10 vol % n-pentane were added and the mixture was left standing at −20° C. over night. The precipitated thiol 36 was filtered off and dried under high vacuum.

Yield: 32.5 mg; 28%

Example 24

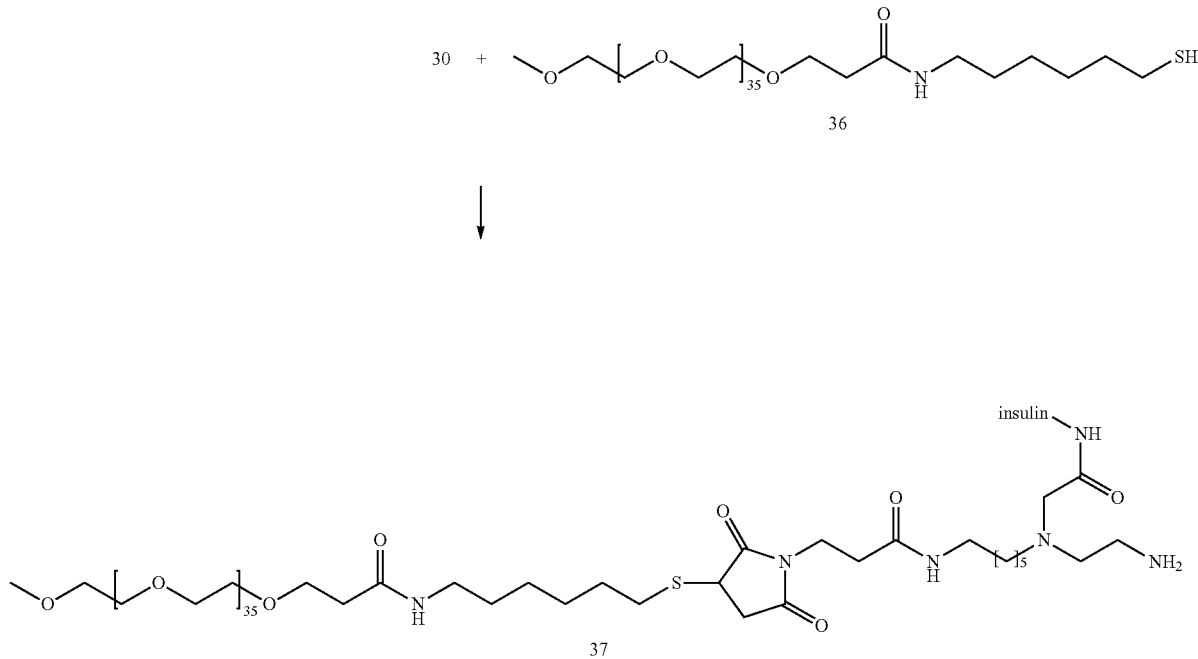

Deprotected insulin-linker conjugate 30 (0.50 mg; 0.08 μmol; 1.00 eq) was dissolved in 0.5 mL 1:1 MeCN/H$_2$O+ 0.1% TFA. 100 μL of a solution of PEG thiol 36 (2.2 mg/mL; 0.22 mg; 0.12 μmol; 1.50 eq) in 1:1 MeCN/H$_2$O+0.1% TFA and 100 μL of citrate buffer (0.5 M citric acid, pH 5.0) were added. The mixture was agitated for 1 h at ambient temperature. 100 μL PEG thiol 36 (2.2 mg/mL; 0.22 mg; 0.12 μmol; 1.50 eq) in 1:1 MeCN/H$_2$O+0.1% TFA and 100 μL phosphate buffer (0.5 M sodium phosphate, pH 6.1) were added. The mixture was agitated for 1.5 h at ambient temperature. 10 μL TFA were added and the product was isolated by preparative HPLC. The pure fractions were combined, frozen and lyophilized to yield PEG conjugate 37.

Yield: 0.2 mg; 31%

MS: m/z=1327.33 [M+6H]$^{6+}$

Example 25

Two samples of 0.1 mg insulin-linker PEG conjugate 37 each were dissolved in 0.5 mL pH 7.4 buffer (60 mM NaH$_2$PO$_4$, 3 mM EDTA, 0.03% (w/v) Tween20, 0.06 mg/mL pentafluorophenol) and 0.5 mL pH 5.5 buffer (60 mM succinic acid, 3 mM EDTA, 0.03% (w/v) Tween 20, 0.01 mg/mL pentafluorophenol) respectively. The samples were incubated at 37° C. in a temperature controlled water bath. At different time points samples were withdrawn and analyzed by RP-HPLC/ESI MS. The amount of released insulin for each time point was calculated from the peak areas of the PEG-conjugate and the peak areas of released insulin. Curve-fitting software was applied to estimate the corresponding halftime of release. Halftimes of 2.9 days (pH 7.4) and 9.3 days (pH 5.5) for the insulin release were determined.

Example 26

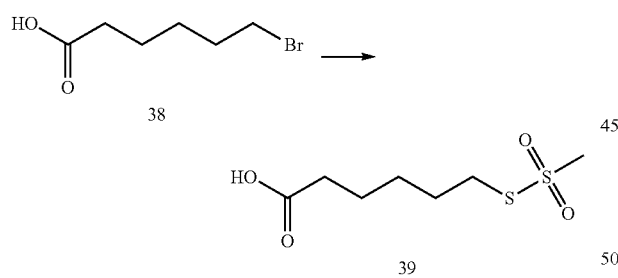

Sodium methanethiosulfonate (688 mg, 5.13 mmol, 1.00 eq.) was added to a solution of 6-bromohexanoic acid (38, 1.00 g, 5.13 mmol, 1.00 eq.) in DMF (8 ml) at room temperature and under argon atmosphere. The mixture was heated to 80° C. and stirred at this temperature for 3 hours under argon atmosphere. The oil bath was removed and the reaction mixture was cooled to room temperature. An IPC by LCMS confirmed full conversion of the starting materials.

Water (20 ml) was added to the reaction mixture and the product was extracted with diethyl ether (3×40 ml). The combined organic solutions were washed with brine (1×60 ml), dried over MgSO$_4$, filtered and concentrated. The crude product (988 mg) was dried under high vacuum over the weekend. The crude material was dissolved in diethyl ether (30 ml) and precipitated by adding the solution to 400 ml of heptane. Product 39 was filtered (pore 3 filter) and the colorless solid was dried under high vacuum for 2 h.

Yield: 944 mg; 81%

MS: m/z=249.06 [M+Na]$^+$

Example 27

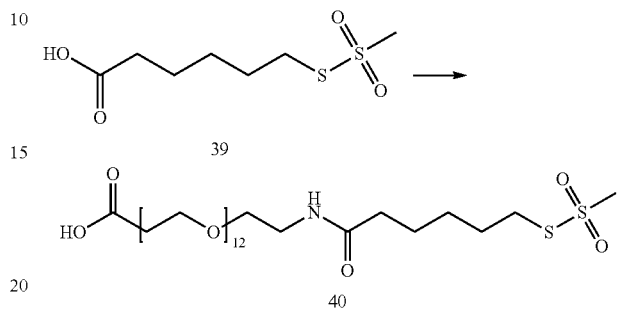

6-MTS-hexanoic acid (39; 1.04 g; 4.59 mmol; 1.05 eq.) and PyBOP (2.39 g; 4.59 mmol; 1.05 eq.) were dissolved in dichloromethane (50 ml) and N,N-diisopropylethylamine (2.50 ml; 14.35 mmol; 3.28 eq.) was added. The reaction mixture was stirred at room temperature for 30 min. H$_2$N-PEG(12)-COOH (2.70 g; 4.37 mmol; 1.00 eq.) was added and the solution was stirred at room temperature for additional 30 min. An IPC LCMS confirmed full conversion of the amino acid.

The reaction was quenched by addition of TFA (1.1 ml) and concentrated to a total volume of about 10 ml. 50 ml of cold MTBE were added to the slightly yellow solution, which turned turbid. The mixture was stored at −20° C. overnight. A white precipitate formed. The suspension was decanted and the solids were washed with 50 ml of cold MTBE. The white, solid residue was dried, whereupon it melted to yield a yellowish oil. The crude product was taken up in 1:1 MeCN/H$_2$O+0.1% TFA and purified by preparative HPLC. The pure fractions were combined, frozen and lyophilized to yield carboxylic acid 40.

Yield: 2.59 g; 72%

MS: m/z=826.45 [M+Na]$^+$

Example 28

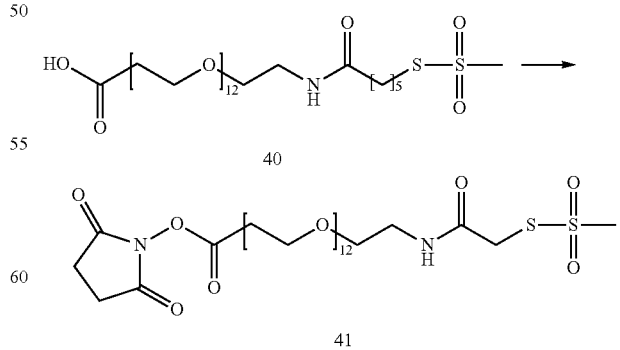

Carboxylic acid 40 (3.16 g; 3.83 mmol; 1.00 eq.), HOSu (528 mg; 4.59 mmol; 1.20 eq.), DMAP (46.7 mg; 0.38 mmol; 0.10 eq.) and DCC (947 mg; 4.59 mmol; 1.20 eq.)

were dissolved in dichloromethane (37 ml). The reaction mixture was stirred at room temperature for 30 min. The urea was filtered off with a syringe reactor and DCM was evaporated. The residue was dissolved in 1:1 MeCN/H$_2$O+0.1% TFA and purified by preparative HPLC. The pure fractions were combined, frozen and lyophilized to yield MTS-PEG(12)-NHS handle 41.

Yield: 2.88 g; 81%

MS: m/z=923.27 [M+H]$^+$

Example 29

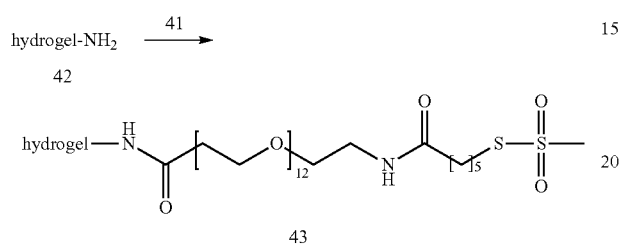

Dry amino functionalized hydrogel 42 (100 mg, 13.8 µmol amino groups) as described in WO2015/067791 (example 3a) is filled into a syringe equipped with a filter frit. The hydrogel is suspended in 5 mL NMP/2% DIPEA. The solvent is discarded and the hydrogel is washed five times with 5 mL NMP/2% DIPEA, the solvent is discarded. 31.8 mg (2.5 eq in respect to the amine content of the hydrogel, 34.5 µmol) of MTS-PEG(12)-NHS handle 41 is dissolved in 1.5 mL NMP and drawn into the syringe. The suspension is allowed to incubate for 2 hours at ambient temperature under gentle agitation. The solvent is discarded and the hydrogel is washed five times with each time 5 mL NMP, the solvent is each time discarded. The hydrogel is washed five times with each time 5 mL 0.1% HOAc, 0.01% Tween 20, the solvent is each time discarded. An aqueous solution containing 0.1% HOAc, 0.01% Tween 20 is added to obtain suspension 43 containing 10 mg/mL hydrogel based on initial weight.

Example 30

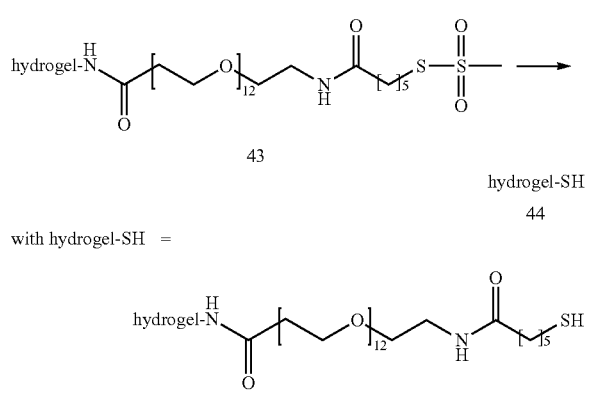

5 mL (50 mg hydrogel based on initial weight; 6.9 µmol) of hydrogel suspension 43 are transferred to a syringe equipped with a filter frit. The solvent is discarded and 10 mL of a 50 mM TCEP solution in water is drawn into the syringe. The resulting hydrogel suspension is incubated at ambient temperature for 15 min. The solvent is discarded and the hydrogel is washed twice with each time 10 mL of the TCEP solution. The solvent is each time discarded. The hydrogel is washed ten times with each time 10 mL of an aqueous solution of 20 mM succinate, 0.01% Tween 20, pH 4.0, the solvent is each time discarded. 20 mM succinate, 0.01% Tween 20, pH 4.0 is added to obtain suspension 44 containing 10 mg/mL hydrogel based on initial weight.

Example 31

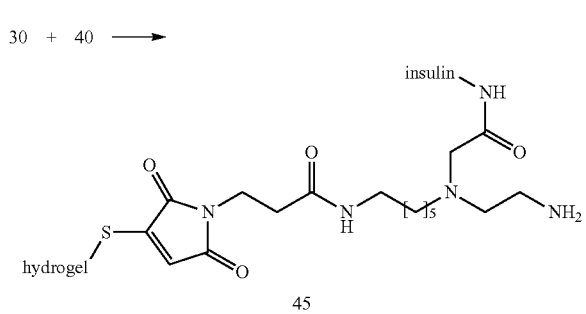

5 mL (50 mg hydrogel based on initial weight; 6.9 µmol; 1.00 eq) of hydrogel suspension 44 are transferred to a syringe equipped with a filter frit. The solvent is discarded. The hydrogel is washed ten times with sodium succinate buffer (pH 3.0, 20 mM; 1 mM EDTA, 0.01% Tween 20). The solvent is each time discarded. Deprotected insulin-linker conjugate 30 (55 mg; 8.3 µmol; 1.20 eq) is dissolved in 3.0 mL 1:1 MeCN/H$_2$O+0.1% TFA. The solution is drawn into the syringe. 1.00 mL phosphate buffer (0.5 M sodium phosphate, pH 6.1) is drawn into the syringe. The suspension is incubated at ambient temperature for 1 hour. The solvent is discarded and the hydrogel is washed ten times with sodium succinate buffer (pH 3.0, 20 mM; 1 mM EDTA, 0.01% Tween 20) and ten times with sodium acetate buffer (pH 5.0, 10 mM; 130 mM NaCl, 0.01% Tween 20). The insulin content of hydrogel suspension 45 is determined by quantitative amino acid analysis after total hydrolysis under acidic conditions.

Example 32

Hydrogel 45 (containing approx. 1 mg insulin) is suspended in 2 ml 60 mM sodium phosphate, 3 mM EDTA, 0.01% Tween 20, pH 7.4, and incubated at 37° C. The suspension is centrifuged at time intervals and the supernatant is analyzed by RP-HPLC at 280 nm and ESI-MS. UV-signals correlating to liberated insulin are integrated and plotted against incubation time.

Curve-fitting software is applied to estimate the corresponding halftime of release.

Abbreviations abs. absolute
AcOH acetic acid
aq. aqueous
Boc tert-butyloxycarbonyl
DCC N,N'-dicyclohexylcarbodiimide
DCM dichloromethane
DIPEA diisopropylethylamine DMAP 4-(dimethylamino)-pyridin
DMF dimethylformamide
DMSO dimethylsulfoxide
EDTA ethylendiaminetetraacetic acid
eq stoichiometric equivalent
ESI Elektrospray ionization
Et$_2$O diethyl ether
HFIP hexafluoroisopropanol
HOSu N-hydroxysuccinimide
HPLC high performance liquid chromatography
IPC in process control
LCMS liquid chromatography with mass spectroscopy
MeCN acetonitrile
MS mass spectrum/mass spectrometry
MTBE methyl tert-butyl ether
MTS methanethiosulfonate
NHS N-hydroxysuccinimide
NMP N-methyl-2-pyrrolidone
PEG poly(ethylene glycol)
PFP pentafluorophenol
PVDF polyvinylidene fluoride
SEC size exclusion chromatography
Su succinimide
TCEP tris-(2-carboxyethyl)-phosphine
TES triethylsilane
TFA trifluoroacetic acid
THF tetrahydrofurane
TLC thin layer chromatography
TSTU O—(N-succinimidyl)-N,N,N',N'-tetramethyluronium tetrafluoroborate
Trt trityl
UPLC ultra performance liquid chromatography

The invention claimed is:

1. A prodrug or a pharmaceutically acceptable salt thereof comprising:
   a conjugate D-L;
   wherein:
   D is a primary or secondary amine- or hydroxyl-comprising biologically active moiety; and
   L comprises a linker moiety -L$^1$ represented by formula (I):

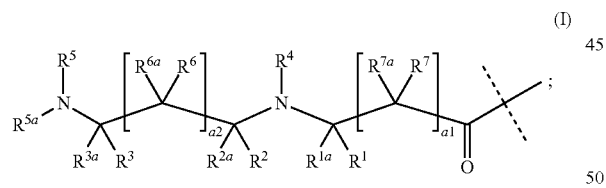

(I)

wherein:
   the dashed line indicates attachment to the primary or secondary amine or hydroxyl of the biologically active moiety by forming an amide or ester linkage, respectively;
   $R^1$, $R^{1a}$, $R^2$, $R^{2a}$, $R^3$, and $R^{3a}$ are independently of each other selected from the group consisting of —H, —C(R$^8$R$^{8a}$R$^{8b}$), —C(=O)R$^8$, —C≡N, —C(=NR$^8$)R$^{8a}$, —CR$^8$(=CR$^{8a}$R$^{8b}$), —C≡CR$^8$, and -T;
   $R^4$, $R^5$, and $R^{5a}$ are independently of each other selected from the group consisting of —H, —C(R$^9$R$^{9a}$R$^{9b}$), and -T;
   a1 and a2 are independently of each other 0 or 1;
   each occurrence of $R^6$, $R^{6a}$, $R^7$, $R^{7a}$, $R^8$, $R^{8a}$, $R^{8b}$, $R^9$, $R^{9a}$, and $R^{9b}$ is independently selected from the group consisting of —H, halogen, —CN, —COOR$^{10}$, —OR$^{10}$, —C(O)R$^{10}$, —C(O)N(R$^{10}$R$^{10a}$), —S(O)$_2$N(R$^{10}$R$^{10a}$), —S(O)N (R$^{10}$R$^{10a}$), —S(O)$_2$R$^{10}$, —S(O)R$^{10}$, —N(R$^{10}$)S (O)$_2$N(R$^{10a}$R$^{10b}$), —SR$^{10}$, —N(R$^{10}$R$^{10a}$), —NO$_2$, —OC(O)R$^{10}$, —N(R$^{10}$)C(O)R$^{10a}$, —N(R$^{10}$) S(O)$_2$R$^{10a}$, —N(R$^{10}$)S(O)R$^{10a}$, —N(R$^{10}$)C(O) OR$^{10a}$, —N(R$^{10}$)C(O)N(R$^{10a}$R$^{10b}$), —OC(O)N (R$^{10}$R$^{10a}$), -T, C$_{1-20}$ alkyl, C$_{2-20}$ alkenyl, and C$_{2-20}$ alkynyl,
   wherein:
   -T, C$_{1-20}$ alkyl, C$_{2-20}$ alkenyl, and C$_{2-20}$ alkynyl are optionally substituted with one or more R$^{11}$, which are the same or different; and
   C$_{1-20}$ alkyl, C$_{2-20}$ alkenyl, and C$_{2-20}$ alkynyl are further optionally interrupted by one or more groups selected from the group consisting of -T-, —C(O)O—, —O—, —C(O)—, —C(O)N(R$^{12}$), —S(O)$_2$N(R$^{12}$)—, —S(O)N(R$^{12}$)—, —S(O)$_2$—, —S(O)—, —N(R$^{12}$)S(O)$_2$N(R$^{12a}$)—, —S—, —N(R$^{12}$)—, —OC(OR$^{12}$)(R$^{12a}$)—, —N(R$^{12}$)C (O)N(R$^{12a}$)—, and —OC(O)N(R$^{12}$)—;
   each occurrence of R$^{10}$, R$^{10a}$, and R$^{10b}$ is independently selected from the group consisting of —H, -T, C$_{1-20}$ alkyl, C$_{2-20}$ alkenyl, and C$_{2-20}$ alkynyl,
   wherein:
   -T, C$_{1-20}$ alkyl, C$_{2-20}$ alkenyl, and C$_{2-20}$ alkynyl are optionally substituted with one or more R$^{11}$, which are the same or different; and
   C$_{1-20}$ alkyl, C$_{2-20}$ alkenyl, and C$_{2-20}$ alkynyl are further optionally interrupted by one or more groups selected from the group consisting of -T-, —C(O)O—, —O—, —C(O)—, —C(O)N (R$^{12}$)—, —S(O)$_2$N(R$^{12}$)—, —S(O)N(R$^{12}$)—S (O)$_2$—, —S(O)—, —N(R$^{12}$)S(O)$_2$N(R$^{12a}$)—, —S—, —N(R$^{12}$)—, —OC(OR$^{12}$)(R$^{12a}$)—, —N(R$^{12}$)C(O)N(R$^{12a}$)—, and —OC(O)N (R$^{12}$)—;
   each occurrence of T is independently selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl, each occurrence of T being further independently optionally substituted with one or more R$^{11}$, which are the same or different;
   each occurrence of R$^{11}$ is independently selected from the group consisting of halogen, —CN, oxo (=O), —COOR$^{13}$, —OR$^{13}$, —C(O)R$^{13}$, —C(O) N(R$^{13}$R$^{13a}$), —S(O)$_2$N(R$^{13}$R$^{13a}$), —S(O)N (R$^{13}$R$^{13a}$), —S(O)$_2$R$^{13}$, —S(O)R$^{13}$, —N(R$^{13}$)S (O)$_2$N(R$^{13a}$R$^{13b}$), —SR$^{13}$, —N(R$^{13}$R$^{13a}$), —NO$_2$, —OC(O)R$^{13}$, —N(R$^{13}$)C(O)R$^{13a}$, —N(R$^{13}$) S(O)$_2$R$^{13a}$, —N(R$^{13}$)S(O)R$^{13a}$, —N(R$^{13}$)C(O) OR$^{13a}$, —N(R$^{13}$)C(O)N(R$^{13a}$R$^{13b}$), —OC(O)N (R$^{13}$R$^{13a}$), and C$_{1-6}$ alkyl, which C$_{1-6}$ alkyl is optionally substituted with one or more halogen, which are the same or different;
   each occurrence of R$^{12}$, R$^{12a}$, R$^{13}$, R$^{13a}$, R$^{13b}$, and R$^{9b}$ is independently selected from the group consisting of —H and C$_{1-6}$ alkyl, which C$_{1-6}$ alkyl is optionally substituted with one or more halogen, which are the same or different;
   optionally, one or more of the pairs R$^1$/R$^{1a}$, R$^2$/R$^{2a}$, R$^3$/R$^{3a}$, R$^6$/R$^{6a}$ and R$^7$/R$^{7a}$ are joined together with the atom to which they are attached to form a C$_{3-10}$ cycloalkyl or a 3- to 10-membered heterocyclyl; and optionally, one or more of the pairs R¹/R², R¹/R³, R¹/R⁴, R¹/R⁵, R¹/R⁶, R¹/R⁷, R²/R³, R²/R⁴, R²/R⁵, R²/R⁶, R²/R⁷, R³/R⁴, R³/R⁵, R³/R⁶, R³/R⁷, R⁴/R⁵, R⁴/R⁶, R⁴/R⁷, R⁵/R⁶, R⁵/R⁷, and R⁶/R⁷ are joined together with the atoms to which they are attached to form a ring A, where:
each ring A is independently selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; and
wherein -L¹ is substituted with one to five -L²-Z moieties,
where:
each -L²- is independently a single chemical bond or a spacer moiety; and
each —Z is independently a carrier moiety which comprises a polymer with a molecular weight of at least 5 kDa.

2. The prodrug of claim 1;
wherein D is a small molecule biologically active moiety, oligonucleotide moiety, peptide nucleic acid moiety, peptide moiety, or protein moiety.

3. The prodrug of claim 1;
wherein D is a primary or secondary amine-containing biologically active moiety.

4. The prodrug of claim 1;
wherein R¹, R¹ᵃ, R⁷, and R⁷ᵃ are independently of each other selected from the group consisting of —H, methyl, ethyl, propyl, iso-propyl, n-butyl, sec-butyl, iso-butyl, tert-butyl, n-pentyl, 1,1-dimethylpropyl, 2,2-dimethylpropyl, 3-methybutyl, 1-methylbutyl, 1-ethylpropyl,

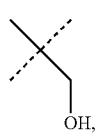
(II-i)

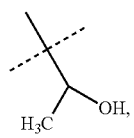
(II-ii)

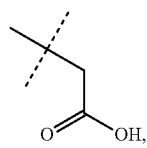
(II-iv)

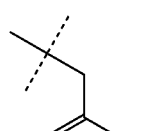
(II-v)

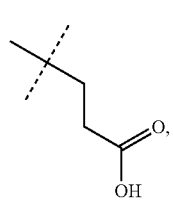
(II-vi)

-continued

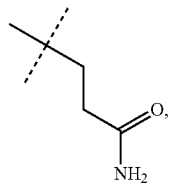
(II-vii)

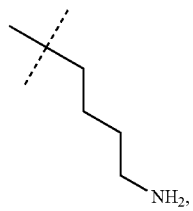
(II-viii)

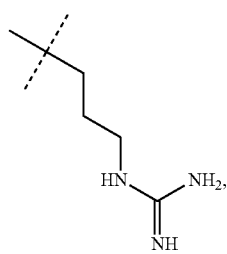
(II-ix)

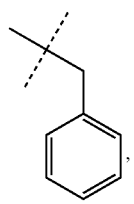
(II-x)

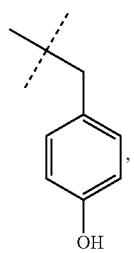
(II-xi)

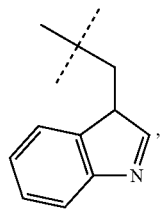
(II-xii)

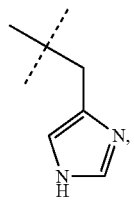
(II-xiii)

-continued

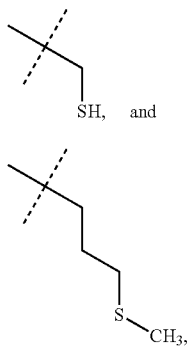

(II-xiv)

(II-xv)

wherein:
dashed lines indicate attachment to the remainder of -L$^1$.

5. The prodrug of claim 1;
wherein a1 is 0.
6. The prodrug of claim 1;
wherein R$^2$, R$^{2a}$, R$^6$, and R$^{6a}$ are independently of each other selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methybutyl, 1-methylbutyl, and 1-ethylpropyl.
7. The prodrug of claim 1;
wherein a2 is 0.
8. The prodrug of claim 1;
wherein R$^3$ and R$^{3a}$ are independently of each other selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methybutyl, 1-methylbutyl, and 1-ethylpropyl.
9. The prodrug of claim 1;
wherein R$^4$ is selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methybutyl, 1-methylbutyl, and 1-ethylpropyl.
10. The prodrug of claim 1;
wherein R$^5$ is selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methybutyl, 1-methylbutyl, and 1-ethylpropyl.
11. The prodrug of claim 1;
wherein R$^{5a}$ is H.
12. The prodrug of claim 1;
wherein Z comprises a PEG-based hydrogel comprising at least 10% w/w PEG.
13. The prodrug of claim 1;
wherein each occurrence of -L$^2$- is independently selected from the group consisting of -T'-, —C(O)O—, —O—, —C(O)—, —C(O)N(R$^{y1}$)—, —S(O)$_2$N(R$^{y1}$)—, —S(O)N(R$^{y1}$)—, —S(O)$_2$—, —S(O)—, —N(R$^{y1}$)S(O)$_2$N(R$^{y1a}$)—, —S—, —N(R$^{y1}$)—, —OC(OR$^{y1}$)(R$^{y1a}$)—, —N(R$^{y1}$)C(O)N(R$^{y1a}$)—, —OC(O)N(R$^{y1}$)—, C$_{1-50}$ alkyl, C$_{2-50}$ alkenyl, and C$_{2-50}$ alkynyl, wherein:
-T'-, C$_{1-50}$ alkyl, C$_{2-50}$ alkenyl, and C$_{2-50}$ alkynyl are optionally substituted with one or more R$^{y2}$, which are the same or different; and
C$_{1-50}$ alkyl, C$_{2-50}$ alkenyl, and C$_{2-50}$ alkynyl are further optionally interrupted by one or more groups selected from the group consisting of -T'-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{y3a}$)—, —S—, —N(R$^{y3}$)—, —OC(OR$^{y3}$)(R$^{y3a}$)—, —N(R$^{y3}$)C(O)N(R$^{y3a}$)—, and —OC(O)N(R$^{y3}$)—;
wherein:
R$^{y1}$ and R$^{y1a}$ are independently of each other selected from the group consisting of —H, -T', C$_{1-50}$ alkyl, C$_{2-50}$ alkenyl, and C$_{2-50}$ alkynyl; wherein:
-T', C$_{1-50}$ alkyl, C$_{2-50}$ alkenyl, and C$_{2-50}$ alkynyl are optionally substituted with one or more R$^{y2}$, which are the same or different; and
C$_{1-50}$ alkyl, C$_{2-50}$ alkenyl, and C$_{2-50}$ alkynyl are further optionally interrupted by one or more groups selected from the group consisting of -T'-, —C(O)O—, —O—, —C(O)—, —C(O)N(R$^{y4}$)—, —S(O)$_2$N(R$^{y4}$)—, —S(O)N(R$^{y4}$)—, —S(O)$_2$—, —S(O)—, —N(R$^{y4}$)S(O)$_2$N(R$^{y4a}$)—, —S—, —N(R$^{y4}$)—, —OC(OR$^{y4}$)(R$^{y4a}$)—, —N(R$^{y4}$)C(O)N(R$^{y4a}$)—, and —OC(O)N(R$^{y4}$)—;
each occurrence of T' is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8-to 30-membered carbopolycyclyl, and 8- to 30-membered heteropolycyclyl, each occurrence of T being further independently optionally substituted with one or more R$^{y2}$, which are the same or different;
each occurrence of R$^{y2}$ is independently selected from the group consisting of halogen, —CN, oxo (=O), —CO-OR$^{y5}$, —OR$^{y5}$, —C(O)R$^{y5}$, —C(O)N(R$^{y5}$R$^{y5a}$), —S(O)$_2$N(R$^{y5}$R$^{y5a}$), —S(O)N(R$^{y5}$R$^{y5a}$), —S(O)$_2$R$^{y5}$, —S(O)R$^{y5}$, —N(R$^{y5}$)S(O)$_2$N(R$^{y5a}$R$^{y5b}$), —SR$^{y5}$, —N(R$^{y5}$R$^{y5a}$), —NO$_2$, —OC(O)R$^{y5}$, —N(R$^{y5}$)C(O)R$^{y5a}$, —N(R$^{y5}$)S(O)$_2$R$^{y5a}$, —N(R$^{y5}$)S(O)R$^{y5a}$, —N(R$^{y5}$)C(O)OR$^{y5a}$, —N(R$^{y5}$)C(O)N(R$^{y5a}$R$^{y5b}$), —OC(O)N(R$^{y5}$R$^{y5a}$), and C$_{1-6}$ alkyl, which C$_{1-6}$ alkyl is optionally substituted with one or more halogen, which are the same or different; and
each occurrence of R$^{y3}$, R$^{y3a}$, R$^{y4}$, R$^{y4a}$, R$^{y5}$, R$^{y5a}$, and R$^{y5b}$ is independently selected from the group consisting of —H and C$_{1-6}$ alkyl, which C$_{1-6}$ alkyl is optionally substituted with one or more halogen, which are the same or different.
14. The prodrug of claim 1;
wherein L$^1$ is substituted with one -L$^2$-Z moiety.
15. The prodrug of claim 1;
wherein the prodrug is of formula (Ia) or (Ib):

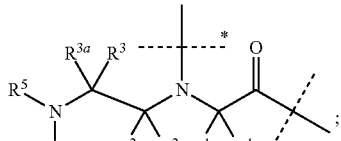

(Ia)

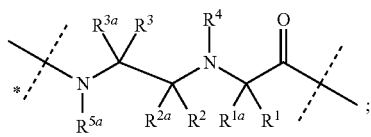

(Ib)

wherein:
  the unmarked dashed line indicates attachment to -D;
  the dashed line marked with the asterisk indicates attachment to -L²-Z; and
  -D, $R^1$, $R^{1a}$, $R^2$, $R^{2a}$, $R^3$, $R^{3a}$, $R^4$, $R^5$, $R^{5a}$, -L²-, and —Z are as defined in claim 1.

16. A pharmaceutical composition comprising:
the prodrug of claim 1; and
one or more excipients.

17. A medicament comprising:
the prodrug of claim 1.

18. A medicament comprising:
the pharmaceutical composition of claim 16.

19. The prodrug of claim 1;
wherein Z comprises a polymer with a molecular weight of at least 7.5 kDa.

* * * * *

UNITED STATES PATENT AND TRADEMARK OFFICE
CERTIFICATE OF CORRECTION

PATENT NO. : 11,633,487 B2
APPLICATION NO. : 15/502084
DATED : April 25, 2023
INVENTOR(S) : Bisek et al.

Page 1 of 1

It is certified that error appears in the above-identified patent and that said Letters Patent is hereby corrected as shown below:

In the Specification

At Column 31, between Line numbers 35 to 40, please replace formula (II-v) structure 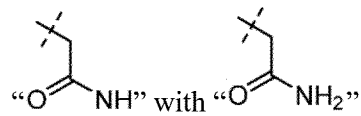 with In the Claims At Column 106, Claim number 1, Line numbers 58 and 59, please replace "$R^{13a}$, $R^{13b}$, and $R^{9b}$" with "$R^{13a}$ and $R^{13b}$"

At Column 107, Claim number 1, Line number 14, please replace "where" with "wherein"

At Column 107, Claim number 4, between Line numbers 55 to 60, please replace formula (II-v) structure 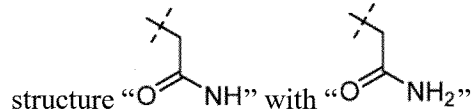

At Column 110, Claim number 13, Line number 27, please insert a space between "8-" and "to" at the end of the line Signed and Sealed this
Eighteenth Day of July, 2023

Katherine Kelly Vidal
*Director of the United States Patent and Trademark Office*